(12) United States Patent
Blackwell et al.

(10) Patent No.: US 8,269,024 B2
(45) Date of Patent: *Sep. 18, 2012

(54) COMPOUNDS AND METHODS FOR MODULATING COMMUNICATION AND VIRULENCE IN QUORUM SENSING BACTERIA

(75) Inventors: Helen E. Blackwell, Middleton, WI (US); Grant D. Geske, Madison, WI (US); Rachel Wezeman, Middleton, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/641,056

(22) Filed: Dec. 17, 2009

(65) Prior Publication Data

US 2010/0305182 A1 Dec. 2, 2010

Related U.S. Application Data

(63) Continuation of application No. 11/275,896, filed on Feb. 2, 2006, now Pat. No. 7,642,285.

(60) Provisional application No. 60/710,620, filed on Aug. 23, 2005, provisional application No. 60/593,681, filed on Feb. 4, 2005.

(51) Int. Cl.
*C07D 309/30* (2006.01)
*A01N 43/08* (2006.01)

(52) U.S. Cl. ........................... 549/291; 514/471

(58) Field of Classification Search .................. 549/291; 514/471
See application file for complete search history.

(56) References Cited

U.S. PATENT DOCUMENTS

| | | | |
|---|---|---|---|
| 5,593,827 A | 1/1997 | Bycroft et al. |
| 5,776,974 A | 7/1998 | Bycroft et al. |
| 6,555,356 B2 | 4/2003 | Kjelleberg et al. |
| 6,559,176 B1 | 5/2003 | Bassler et al. |
| 6,756,404 B2 | 6/2004 | Livinghouse |
| 6,780,890 B2 | 8/2004 | Bassler et al. |
| 6,958,145 B2 | 10/2005 | Kumar et al. |
| 7,026,353 B2 | 4/2006 | Kjelleberg et al. |
| 7,078,435 B2 | 7/2006 | Livinghouse |
| 7,094,394 B2 | 8/2006 | Davies et al. |
| 7,332,509 B2 | 2/2008 | Schaper et al. |
| 7,335,779 B2 | 2/2008 | Ammendola |
| 7,338,969 B2 | 3/2008 | Ammendola |
| 7,910,622 B2 | 3/2011 | Blackwell et al. |
| 2002/0177715 A1 | 11/2002 | Pesci et al. |
| 2003/0105143 A1 | 6/2003 | Ammendola et al. |
| 2003/0125381 A1 | 7/2003 | England et al. |
| 2003/0198692 A1 | 10/2003 | Holmstrom et al. |
| 2003/0224032 A1 | 12/2003 | Read et al. |
| 2004/0115732 A1 | 6/2004 | Suga et al. |
| 2004/0147595 A1 | 7/2004 | Kjelleberg et al. |
| 2004/0180829 A1 | 9/2004 | Bassler et al. |
| 2005/0215772 A1 | 9/2005 | Kumar |
| 2006/0052425 A1 | 3/2006 | Handelsman et al. |
| 2008/0027115 A1 | 1/2008 | Suga et al. |
| 2008/0312899 A1 | 12/2008 | Blackwell et al. |
| 2011/0046195 A1 | 2/2011 | Blackwell et al. |
| 2011/0212860 A1 | 9/2011 | Blackwell et al. |

FOREIGN PATENT DOCUMENTS

| | | |
|---|---|---|
| JP | 49020492 | 5/1974 |
| JP | 2235850 | 9/1990 |
| JP | 3031245 | 2/1991 |
| JP | H06-506588 A | 7/1994 |
| WO | WO 92/18614 | 10/1992 |
| WO | WO 92/18614 A | 10/1992 |
| WO | WO 96/29392 | 9/1996 |
| WO | WO 99/27786 | 6/1999 |
| WO | WO 99/53915 | 10/1999 |
| WO | WO 01/43739 | 6/2001 |
| WO | WO 01/68091 | 9/2001 |
| WO | WO 01/76594 | 10/2001 |
| WO | WO 01/85664 | 11/2001 |
| WO | WO 02/00639 | 1/2002 |
| WO | WO 02/18342 | 3/2002 |
| WO | WO 02/47681 | 6/2002 |
| WO | WO 02/102370 | 12/2002 |
| WO | WO 03/039529 | 5/2003 |
| WO | WO 03/106445 | 12/2003 |
| WO | WO 2006/079015 | 7/2006 |
| WO | WO 2008/116029 | 9/2008 |

OTHER PUBLICATIONS

McClean et al, Microbiology (Reading, United Kingdom), 1997, 143(12), 3703-3711.*
Schaefer et al. Journal of Bacteriology (1996), 178(10), 2897-2901.*
Persson, T., Givskov M., Nielsen, J (Dec. 2005) "Quorum sensing inhibition: targeting chemical communication in gram-negative bacteria," Curr Med Chem 12(26) 3103-3115.
Bassler et al. (Aug. 1993) "Intercellular Signaling in *Vibrio harveyi*: Sequence and Function of Genes Regulating Expression of Luminescence," *Mol. Microbiol.* 9(4):773-786.
Bassler et al. (Jul. 1994) "Multiple Signaling Systems Controlling Expression of Luminescence in *Vibrio harveyi*: Sequence and Function of Genes Encoding a Second Sensory Pathway," *Mol. Microbiol.* 13(2):273-286.

(Continued)

*Primary Examiner* — Nizal Chandrakumar

(74) *Attorney, Agent, or Firm* — Greenlee Sullivan P.C.

(57) ABSTRACT

The present invention provides compositions and methods for modulating the communication and virulence of quorum sensing bacteria. In various exemplary embodiments, the invention provides a combinatorial library of quorum sensing compounds including synthetic analogs of naturally occurring and non-naturally occurring acyl-homoserine lactone (AHL) analogs, and methods of synthesizing and using these compounds.

21 Claims, 76 Drawing Sheets

OTHER PUBLICATIONS

Bassler et al. (Jun. 1997) "Cross-Species Induction of Luminescence in the Quorum-Sensing Bacterium *Vibrio harveyi*," *J. Bacteriol.* 179(12):4043-4045.

Bassler et al. (Apr. 21, 2006) "Bacterially Speaking," *Cell* 125(2):237-246.

Bassler et al. (1995) *Two Component Signal Transduction*, Hoch et al. eds., Am. Soc. Microbiol., Washington D.C., pp. 431-435.

Blackwell, H.E. (2003) "Out of the Oil Bath and into the Oven—Microwave-Assisted Combinatorial Chemistry Heats up," *Org. Biomol. Chem.* 1:1251-1255.

Blackwell, H.E. (2006) "Hitting the SPOT: Small-Molecule Macroarrays Advance Combinatorial Synthesis," *Curr. Opin. Chem. Biol.* 10:203-212.

Bottomley et al. (May 4, 2007) "Molecular Insights into Quorum Sensing in the Human Pathogen *Pseudomonas aeruginosa* from the Structure of the Virulence Regulator LasR Bound to its Autoinducer," *J. Biol. Chem.* 282(18):13592-13600.

Castang et al. (Oct. 18, 2004) "N-Sulfonyl Homoserine Lactone as Antagonists of Bacterial Quorum Sensing," *Bioorg. Med. Chem. Lett.* 14(20):5145-5149.

Davies et al. (Apr. 10, 1998) "The Involvement of Cell-to-Cell Signals in the Development of a Bacterial Biofilm," *Science* 280:295-298.

de Kievit et al. (Sep. 2000) "Bacterial Quorum Sensing in Pathogenic Relationships," *Infect. Immun.* 68(9):4839-4849.

de Kievit et al. (Apr. 2001) "Quorum-Sensing in *Pseudomonas aeruginosa* Biofilms: Their Role and Expression Patterns," *Appl. Environ. Microbiol.* 67(4):1865-1873.

Eberhard et al. (1986) "Analogs of the Autoinducer of Bioluminescence in *Vibrio fischeri*," *Arch. Microbiol.* 146:35-40.

Eberhard et al. (2000) "Chemical Synthesis of Bacterial Autoinducers and Analogs," *Methods Enzymol.* 305:301-315.

Frezza et al. (2006) "Synthesis and Biological Evaluation of Homoserine Lactone Derived Ureas as Antagonists of Bacterial Quorum Sensing," *Bioorg. Med. Chem.* 14:4781-4791.

Fuqua et al. (Sep. 2002) "Listening in on Bacteria: Acyl-Homoserine Lactone Signaling," *Nat. Rev. Mol. Cell Biol.* 3:685-695.

Fuqua et al. (2001) "Regulation of Gene Expression by Cell-To-Cell Communication: Acyl-Homoserine Lactone Quorum Sensing," *Ann. Rv. Genet.* 35:439-468.

Gasperi et al. STN Abstract of Tetrahedron Letters (2003), 44(27), 4953-4956.

Geske et al. (Jun. 2008) "Expanding Dialogues: From Natural Autoinducers to Non-Natural Analogues that Modulate Quorum Sensing in Gram-Negative Bacteria" *Chem. Soc. Rev.* 37:1432-1447.

Geske et al. (Jan. 2008) "Comparative Analyses of N-Acylated Homoserine Lactones Reveal Unique Structural Features that Dictate Their Ability to Activate or Inhibit Quorum Sensing," *ChemBioChem* 9: 389-400.

Geske et al. (May 4, 2007) "N-Phenylacetanoyl-L-homoserine Lactones can Strongly Antagonize or Superagonize Quorum Sensing in *Vibrio fischeri*" *ACS Chem. Biol.* 2(5):315-320.

Geske et al. (Oct. 2007)"Modulation of Bacterial Quorum Sensing with Synthetic Ligands: Systematic Evaluation of N-Acylated Homoserine Lactones in Multiple Species and New Insights into Their Mechanisms of Action," *J. Am. Chem. Soc.* 129:13613-13625.

Geske et al. (Aug. 26, 2005) "Small Molecule Inhibitors of Bacterial Quorum Sensing and Biofilm Formation," *J. Am. Chem. Soc.* 127:12762-12763.

Glansdorp et al. (2004) "Synthesis and Stability of Small Molecule Probes for *Pseudomonas aeruginosa* quorum Sensing Modulation," *Org. Biomol. Chem.* 2:3329-3336.

Gonzalez et al. (Dec. 2006) "Messing with Bacterial Quorum Sensing," *Microbiol. Mol. Biol. Rev.* 70(4):859-875.

Greenberg et al. (1999) "Quorum Sensing in Gram-Negative Bacteria: An Important Signaling Mechanism in Symbiosis and Disease," In; *Microbial Ecology and Infectious Disease*, Rosenberg, E. Ed., American Society for Microbiology: Washington, D.C. pp. 112-122.

Hentzer et al. (2003) "Attenuation of *Pseudomonas aeruginosa* Virulence by Quorum Sensing Inhibitors," *EMBO J.* 22(15):3803-3815.

Ikeda et al. (2001) "The Synthesis of Optically Pure Enantiomers of N-Acyl- Homoserine Lactone Autoinducers and Their Analogues," *Chem. Lett.* 30(4):314-315.

International Search Report, Corresponding to International Application No. PCT/US2006/003715, Mailed Apr. 17, 2007.

Izawa et al. STN Abstract of JP 02235850, Sep. 19, 1990.

Izawa et al. STN Abstract of JP03031245, Feb. 12, 1991.

Janssens et al. (Jan. 2007) "Synthesis of N-Acyl Homoserine Lactone Analogues Reveals Strong Activators of SdiA, the *Salmonella enterica* Serovar Typhimurium LuxR Homologue," *Appl. Environ. Microbiol.* 73(2):535-544.

Jog et al. (Feb. 2006) "Stereoisomers of *P. aeruginosa* Autoinducer Analog to probe the Regulator Binding Site," *Chem. Biol.* 13:123-128.

Kline et al. (Dec. 20, 1999) "Novel Synthetic Analogs of the *Pseudomonas* Autoinducer," *Bioorg. Med. Chem. Lett.* 9(24):3447-3452.

Ko et al. (Jan. 15, 1998) "New Cleavage Approached to Combinatorial Synthesis of Homoserine Lactones," *Tetrahedron Lett.* 39(3-4):297-300.

Lyon et al. (Nov. 2003) "Chemical Signaling Among Bacteria and its Inhibition," *Chem. Biol.* 10(11):1007-1021.

Marketon et al. STN Abstracts of Journal of Bacteriology (2003), 185(1), 325-331.

Martinelli et al. BMS Microbiology 2004 4:25, 1-10.

Mattmann et al. (Nov. 28, 2007) "Synthetic Ligands that Activate and Inhibit a Quorum-Sensing Regulator in *Pseudomonas aeruginosa*" *Biorg. Med. Chem. Lett.* 18: 3072-3075.

Misato et al. STN Abstract of JP49020492, May 25, 1974.

Müh et al. (Nov. 2006) "Novel *Pseudomonas aeruginosa* Quorum-Sensing Inhibitors Identifies in an Ultra-High-Throughput Screen," *Antimicrob. Agents Chemother.* 50(11):3674-3679.

Müh et al. (Nov. 7, 2006) "A Structurally Unrelated Mimic of a *Pseudomonas aeruginosa* Acyl-Homoserine Lactone Quorum-Sensing Signal," *Proc. Nat. Acad. Sci. USA* 103(45):16948-16952.

Passador et al. (Oct. 1996) "Functional Analysis of the *Pseudomonas aeruginosa* Autoinducer PAI," *J. Bacteriol.* 178(20):5995-6000.

Pearson et al. (Jan. 1994) "Structure of the Autoinducer Required for Expression of *Pseudomonas aeruginosa* Virulence Genes," *Proc. Natl. Acad. Sci. USA* 91:197-201.

Persson et al. (2005) "Rational Design and Synthesis of New Quorum-Sensing Inhibitors Derived from Acylated Homoserine Lactones and Natural Products from Garlic," *Org. Biomol. Chem.* 3:253-262.

Ramussen et al. (2006) "Quorum Sensing Inhibitors: A Bargain of Effects," *Microbiology* 152:895-904.

Reverchon et al. Biorganic and Medicinal Chemistry Letters 12 (2002) 1153-1157.

Schaefer et al. (May 1996) "Quorum Sensing in *Vibrio fischeri*: Probing Autoinducer-LuxR Interactions with Autoinducer Analogs," *J. Bacteriol.* 178:2897-2901.

Smith et al. (Jun. 2003) "Library Screening for Synthetic Agonists and Antagonists of a *Pseudomonas aeruginosa* Autoinducer," *Chem. Biol.* 10(6):563-571.

Smith et al. (Jan. 2003) "Induction and Inhibition of *Pseudomonas aerinosa* Quorum Sensing by Synthetic Autoinducer Analogs," *Chem. Biol.* 10(1):81-89.

Smith et al. (Feb. 2003) "*P. aeruginosa* Quorum-Sensing Systems and Virulence," *Cur. Opin. Microbiol.* 6(1):56-60.

Taha et al. (Nov. 2006) "Discovery of Potent Inhibitor of *Pseudomonal* Quorum Sensing via Pharmacophore Modeling and in Silico Screening," *Bioorg. Med. Chem. Lett.* 16(22):5902-5906.

Teplitski et al. (2000) "Plants Secrete Substances That Mimic Bacterial N-Acyl Homoserine Lactone Signal Activities and Affect Population Density-Dependent Behaviors in Associated Bacteria," *Mol. Plant Microbe. Interact.* 13(6):637-648.

von Bodman (Jun. 1998) "A Negative Regulator Mediates Quorum-Sensing Control of Exopolysaccharide Production in *Pantoea stewartii* subsp. *Stewartii*," *Proc. Nat. Acad. Sci. USA* 95:7687-7692.

Waters et al. (2005) "Quorum Sensing: Cell-to-Cell Communication in Bacteria," *Ann. Rev. Cell. Dev. Biol.* 21:319-346.

Welch et al. (2005) "Cell-Cell Communication in Gram-Negative Bacteria," *Molecular Biosystems* 1:196-202.

Whitehead et al. (Aug. 2001) "Quorum-Sensing Gram-Negative Bacteria," *FEMS Microbiol. Rev.* 25(4):365-404.

Written Opinion, Corresponding to International Application No. PCT/US/2006/003715, Mailed Apr. 17, 2007.

Zhang et al. (Jun. 27, 2002) Structure of a Bacterial Quorum-Sensing Transcription Factor Complexed with Pheromone and DNA *Nature* 417:971-974.

Zhu et al. (Oct. 1998) "Analogs of the Autoinducer 3-Oxooctanoyl-Homoserine Lactone Strongly Inhibit Activity of the TraR Protein of *Agrobacterium tumefaciens*," *J. Bacteriol.* 180(20):5398-5405.

Schaefer, Amy L. et al "Long-Chain Acyl-Homoserine Lactone Quorum-Sensing Regulation of *Rhodobacter capsulatus* Gene Transfer Agent Production" J. of Bacteriology (Dec. 2002, p. 6515-6521).

Zhu, Jun et al. "Agrobacterium Bioassay Strain for Ultrasensitive Detection of N-Acylhomoserine Lactone-Type Quorum-Sensing Molecules: Detection of Autoinducers in *Mesorhizobium huakuii*" App. Environ. Microbiol. Nov. 2003, 69(11):6949.

Chhabra, Siri Ram et al. "Synthetic Analogues of the Bacterial Signal (Quorum Sensing) Molecule N-(3-Oxododecanoyl)-L-homoserine Lactone as Immune Modulators" J. Med. Chem. 2003, 46, 97-104 (published on the web Nov. 2002).

Yates, Edwin A. et al. "N-Acylhomoserine Lactones Undergo Lactonolysis in a pH-, Temperature-, and Acyl Chain Length-Dependent Manner during Growth of *Yersinia pseudotuberculosis* and *Pseudomonas aeruginosa*" Infect. Immun. Oct. 2002, 70(10):5635.

English translation of an Office Action issued in Japanese application 2007-554210 on Apr. 24, 2012.

\* cited by examiner

COMPOUNDS AND METHODS FOR MODULATING COMMUNICATION AND VIRULENCE IN QUORUM SENSING BACTERIA

CROSS-REFERENCE TO RELATED APPLICATIONS

This application is a continuation of U.S. application Ser. No. 11/275,896, filed Feb. 2, 2006 now allowed which claims the benefit of U.S. provisional application 60/593,681, filed Feb. 4, 2005 and U.S. provisional application 60/710,620, filed Aug. 23, 2005, all of which are incorporated by reference herein for all purposes.

FIELD OF THE INVENTION

This invention relates generally to molecules and methods for modulating quorum sensing in bacteria.

BACKGROUND OF THE INVENTION

Many microbial pathogens cause tremendous damage worldwide, in humans as well as in animals and crop plants. The continuing emergence of multiple-drug-resistant pathogen strains has necessitated finding new compounds that can be used in antimicrobial treatment. In general, two strategies exist for controlling pathogens, either kill the pathogen or attenuate its virulence such that it does not damage the host.

The strategy of attenuating bacterial virulence has the advantage of not creating selective pressure in favor of drug resistant strains. Antimicrobial compounds having 20 virulence-attenuating but not cell-killing effects are expected to remain effective for longer periods of time than conventional antibiotics because of the lack of development of drug resistance. This approach has, however, suffered from a lack of specific targets for rational drug design.

Many bacteria use autoinducer ligands to monitor their population densities in a phenomenon called quorum sensing. At high cell densities, bacteria use this chemical signaling process to switch from a nomadic existence to that of multicellular community. This lifestyle switch is significant, as numerous pathogenic bacteria use quorum sensing to turn on virulence pathways and form drug-impervious communities called biofilms that are the basis of myriad chronic infections. Over 80% of bacterial infections in humans involve the formation of biofilms, as exemplified in lung infections by *Pseudomonas aeruginosa*, which is the primary cause of morbidity in cystic fibrosis patients. The treatment of infections by pathogens that form biofilms costs over $1 billion/year in the US alone.

The control of gene expression in response to cell density was first described in the marine luminous bacteria *Vibrio fischeri* and *Vibrio harueyi*. Quorum sensing bacteria synthesize, release, and respond to specific acyl-homoserine lactone ("AHL" or "HSL") signaling molecules called autoinducers ("AI") to control gene expression as a function of cell density. The classical quorum-sensing pathway comprises at least three components: a membrane associated receptor/transcription factor; a diffusible signal, the autoinducer; and a recognition site in the promoter region of the target gene. The autoinducer binds to the receptor causing the receptor/AI complex to be internalized. This, in turn, allows the receptor or receptor/AI complex to bind to the promoter region of the target gene or genes altering transcription and down-regulating or up-regulating gene expression. In most cases, this includes increased AI expression, thereby resulting in a cascade effect.

In recent years it has become apparent that many Gram-negative bacteria employ one or more quorum sensing systems. The quorum-sensing system is an attractive antibacterial target because it is not found in humans and is critical for high level bacterial virulence. Bacterial quorum sensing systems comprise AHL derivatives with different acyl side chains to regulate, in a cell-density dependent manner, a wide variety of physiological processes unique to the life-cycle of each microbe. These processes include: swarming, motility, biofilm formation, conjugation, bioluminescence and/or production of pigments, antibiotics and enzymes. For example, in *P. aerugniosa* quorum sensing pathways affect the expression of various exoenzymes, biofilm formation and cell-cell spacing. Other bacteria react to quorum sensing stimulation by expressing proteases and pectinases, expressing pili, entering stationary phase, emerging from lag phase and initiating cell division.

Biofilms are dense extracellular polymeric matrices in which the bacteria embed themselves. Biofilms allow bacteria to create a microenviroment that attaches the bacteria to the host surface and contains excreted enzymes and other factors allowing the bacteria to evade host immune responses including antibodies and cellular immune responses. Such biofilms can also exclude antibiotics. Further, biofilms can be extremely resistant to removal and disinfectant. For individuals suffering from cystic fibrosis, the formation of biofilms by *P. aerugniosa* is eventually fatal. Other bacteria also respond to quorum sensing signals by producing biofilms. Biofilms are inherent in dental plaques, and are found on surgical instruments, food processing and agriculture equipment and water treatment and power generating machinery and equipment.

Because of the virulence factors it triggers, the bacterial quorum-sensing system offers a novel target for use in modulating the virulence of pathogenic bacteria. All acyl-homoserine lactone quorum-sensing systems described to date, except that of *V. harueyi*, utilize AI synthases encoded by a gene homologous to luxI of *V. fischeri*. The response to the autoinducer is mediated by a transcriptional activator protein encoded by a gene homologous to luxR of *V. fischeri* (Bassler and Silverman, in Two Component Signal Transduction, Hoch et al., eds., Am. Soc. Microbiol. Washington D.C., pp. 431-435, 1995). Thus, the AHL quorum sensing system is present in a broad spectrum of pathogenic bacteria.

Gram-negative bacteria represent numerous relevant pathogens using quorum-sensing pathways. Besides *P. aeruginosa*, other quorum sensing bacteria include: *Aeromonas hydrophila, A. salmonicida, Agrobacterium tumefaciens, Burkholderia cepacia, Chromobacterium violaceum, Enterobacter agglomeran, Erwinia carotovora, E. chrysanthemi, Escherichia coli, Nitrosomas europaea, Obesumbacterium proteus, Pantoea stewartii, Pseudomonas aureofaciens, P. syringae, Ralstonia solanacearum, Rhisobium etli, R. leguminosarum, Rhodobacter sphaeroides, Serratia liguefaciens, S. marcescens, Vibrio anguillarum, V. fischeri, V. cholerae, Xenorhabdus nematophilus, Yersinia enterocolitica, Y. pestis, Y. pseudotuberculosis, Y. medievalis,* and *Y. ruckeri*. Studies on the above listed bacteria indicate that, while the AI is generally an AHL compound, the genes affected as well as the phenotypes resulting from induction of the promoter differs according to the particular life cycle of each bacterium. Further, quorum sensing stimulation typically results in altered expression of multiple genes.

In addition to affecting multiple genes, some bacteria have multiple stages of quorum sensing response. In these bacteria, the different stages of quorum sensing may be induced by different ligand/receptor pairs and result the expression of different sets of genes with similarly distinct phenotypes. For example, *V. harueyi* has two independent density sensing systems (Signaling Systems 1 and 2), and each is composed of a sensor-autoinducer pair. Signaling System 1 is composed of Sensor 1 and autoinducer 1 (AI-1), which is N43-hydroxybutanoyl)-L-homoserine lactone (see Bassler et al., Mol. Microbiol. 9: 773-786, 1993). Signaling System 2 is composed of Sensor 2 and autoinducer 2 (AI-2) (Bassler et al., Mol. Microbiol. 13: 273-286, 1994). The structure of AI-2 heretofore has not been determined, nor have the gene(s) involved in biosynthesis of AI-2 been identified. Signaling System 1 is a highly specific system proposed to be used for intra-species communication and Signaling System 2 appears to be less species-selective, and is hypothesized to be for inter-species communication (Bassler et al., J. Bacteriol. 179: 4043-4045, 1997). Other research indicates that *V. cholerae* also has two stages of quorum-sensing response. The first, limits biofilm production, so that the microbe can escape the biofilm once it has passed through harsh environments such as hosts stomach. The second stage initiates swarming once the bacterium have escaped the biofilm and multiplied in the gut; allowing the bacteria to leave the host and start the cycle again.

Because of the diversity of quorum sensing ligands and phenotypes, having a large number of quorum sensing compounds with which to probe diverse quorum sensing responses will allow clinicians to identify ways to modulate or attenuate such responses. Further, if synthetic quorum sensing analogs were used, a greater diversity of responses may be identified other than those resulting from the native ligand. In addition, developing a synthetic route to quorum sensing compounds would provide a quick, more efficient way of producing analogs that would not rely on time-consuming techniques of molecular biology and would not per se be based on backbone of a native ligand. In addition, this strategy of attacking pathogenic bacteria via their quorum-sensing pathways provides methods of controlling bacterial virulence without resorting to antibiotics. This will allow treatment of bacterial infections without inducing antibiotic resistance and the concomitant breeding of "superbugs".

Recent studies in vivo have shown that the virulence of *P. aeruginosa* lacking one or more genes responsible for quorum sensing is attenuated in its ability to colonize and spread within the host. Similarly, elimination of the AHL synthase in several plant pathogenic bacteria has led to complete loss of infectivity (Beck von Bodman, 1998, Proc. Natl. Acad. Sci. USA 95:7687-7692; Whitehead et al., 2001, Microbiol. Rev. 25:365-404). Transgenic plant systems engineered to express of AHL synthases ectopically, to produce inducing levels of AHLs, have shifted the balance of host-microbe interactions in favor of disease resistance (Fray et al., 1999, Nat. Biotechnol. 171:1017-1020; Mae et al., 2001, Mol. Plant Microbe Interact. 14:1035-1042). It is thought that the production of endogenous AHL compounds by plants is the basis of varying degrees of disease resistance and susceptibility (Teplitski et al., 2000, Mol. Plant-Microbe Interact. 13:637-648). The halogenated furanones produced by some marine algae are known to have a pronounced effect on suppressing marine biofouling. Some furanones have also been shown to effect on *V. cholerae* by eliminating its ability to express genes associated with their virulence phase.

The current understanding is that, at some threshold AHL concentration (and related cell density), the AHL ligand (AI) will bind its cognate receptor, a LuxR-type protein, and activate the transcription of target genes involved in group behavior. Fuqua, C.; Greenberg, E. P. *Nat. Rev. Mol. Cell Biol.* 2002, 3, 685-695. Blocking the binding of the endogenous AHL to its receptor with a non-native AHL is an attractive strategy for quorum sensing control.

In addition to their pathogenic costs, quorum sensing bacteria also have significant economic impact in industries other than health care. For example, in agriculture, various species of the genera *Rhisobium*, *Bradyrhizobium* and *Sinorhizobium* are important plant symbionts helping legumes to fix nitrogen, while, species of the genera *Erwinia*, *Xanthomonas* and *Pseudomonas* are responsible for significant food-spoilage of. Other industries, such as power generation, paper making and water treatment are subject to biofouling by many types of slime forming bacteria such as *Deinococcus geothermalis*.

Nevertheless, the pace of AHL analog discovery has been slow as the majority of AHLs synthesized to date have been generated in poor yields and low purities and screened on an ad hoc basis (Eberhard, A.; Schineller, J. B. *Methods Enzymol.* 2000, 305, 301-315; Reverchon, S.; Chantegrel, B.; Deshayes, C.; Doutheau, A.; Cotte-Pattat, N. *Bioorg. Med. Chem. Lett.* 2002, 12, 1153-1157; Zhu, J.; Beaber, J. W.; More, M. I.; Fuqua, C.; Eberhard, A.; Winans, S. C. *J. Bacteriol.* 1998, 180, 5398-5405). Currently there are no antibacterial compounds that target the bacterial quorum sensing system to reduce bacterial virulence and increase susceptibility to bactericidal antibiotics. Therefore, new synthetic approaches are required for the generation of AHL analogs and the systematic evaluation of the effects of AHL ligand structure on quorum sensing. In addition, non-native AHL-analogs may provide significant benefits in their ability to stimulate quorum pathways without resulting increased virulence and pathogenicity.

SUMMARY OF THE INVENTION

The invention disclosed herein provides newly identified novel compounds that are autoinducer analogs. In addition, the novel compounds disclosed may act as either antagonists or agonists in various quorum sensing pathways. In various embodiments the invention also provides novel methods of synthesis to produce autoinducer analogs that include both natural and non-natural AHL analogs. Various AHL analogs produced as described herein can be used to modulate and/or regulate the infectivity and pathogenicity of quorum sensing bacteria and allow treatment of bacterial infections or blooms without resort to or in addition to antibiotics.

In various exemplary embodiments this invention discloses novel quorum sensing AHL analogs. In these exemplary embodiments the novel quorum sensing analogs disclosed herein are both AHL agonists and antagonists.

In various other exemplary embodiments the AHL analogs disclosed herein can be synthesized in high purity and with excellent yields.

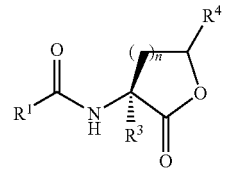

(I)

In various exemplary embodiments, the present invention provides compounds of Formula I where n is 1, 2 or 3, wherein if n=1, the ring C bound to the substituted amino can be a chiral center, $R^1$ is selected from —H, —$(CH_2)_aCH_3$, —$(CH_2)_aCOR^2$, —$(CH_2)_aCHOHR^2$, —$(CH_2)_aR^6$, —O—$(CH_2)_aCH_3$, —$(CH_2)_aHC$=$CH$, —$HC$=$CH(CH_2)_aCH_3$, —$(CH_2)_aHC$=$CH(CH_2)_bCH_3$, —$R^6HC$=$CHR^7$, —$R^6C$=$CR^7$, substituted and unsubstituted $C_3$-$C_8$ cycloalkyl, substituted and unsubstituted $C_3$-$C_8$ aryl, three to eight member substituted and unsubstituted heterocyclic rings, where the heteroatom is at least one of O, S or N, $R^2$ is selected from —H, —$(CH_2)_aCH_3$, substituted and unsubstituted $C_3$-$C_8$ cycloalkyl, substituted and unsubstituted $C_3$-$C_8$ aryl, three to eight member substituted and unsubstituted heterocyclic rings, where the heteroatom is at least one of O, S or N, $R^3$ is selected from —H, —$CH_2CH_3$, —$CH_3$, $R^4$ is selected from —H, —$CH_2$—, $R^5$ is —H, $R^6$ and $R^7$ are the same or different, selected from —H, substituted and unsubstituted $C_3$-$C_8$ cycloalkyl, substituted and unsubstituted $C_3$-$C_8$ aryl, three to eight member substituted and unsubstituted heterocyclic rings, where the heteroatom is at least one of O, S or N, and a and b are independently integers from 0 to 15.

In certain preferred embodiments, compounds are selected from the compounds of Table 1.

TABLE 1

Compounds of Formula I

| Cmpd | $R^1$ | $R^2$ | $R^3$ | $R^4$ | $R^5$ | n |
|------|-------|-------|-------|-------|-------|---|
| 7a | —$(CH_2)_2CH_3$ | — | H | H | — | 1 |
| 7b | —$(CH_2)_4CH_3$ | — | H | H | — | 1 |
| 7c | —$(CH_2)_6CH_3$ | — | H | H | — | 1 |
| 7d | —$(CH_2)_8CH_3$ | — | H | H | — | 1 |
| 7e | —$(CH_2)_{10}CH_3$ | — | H | H | — | 1 |
| 7f | —$(CH_2)_{12}CH_3$ | — | H | H | — | 1 |
| 8a | —$(CH_2)COR^2$ | —$(CH_2)_2CH_3$ | H | H | — | 1 |
| 8b | —$(CH_2)COR^2$ | —$(CH_2)_4CH_3$ | | | | |
| 8c | —$(CH_2)COR^2$ | —$(CH_2)_6CH_3$ | | | | |
| 8d | —$(CH_2)COR^2$ | —$(CH_2)_8CH_3$ | | | | |
| 8e | —$(CH_2)COR^2$ | —$(CH_2)_{10}CH_3$ | | | | |
| | —$(CH_2)_aCHOHR^2$ | —$(CH_2)_aCH_3$ | | | | |
| | —$(CH_2)_aR^6$ | | | | | |
| | —O—$(CH_2)_aCH_3$ | | | | | |
| | —$(CH_2)_aHC$=$CH$ | | | | | |
| | —$HC$=$CH(CH_2)_aCH_3$ | | | | | |
| | —$(CH_2)_aHC$=$CH(CH_2)_bCH_3$ | | | | | |
| 29 (L) | —$(CH_2)_5HC$=$CH(CH_2)_5CH_3$ | — | H | H | — | 1 |
| 22 (L) | —$(CH_2)_2HC$=$CH_2$ | — | H | H | — | 1 |
| | —$R^6HC$=$CHR^7$ | | | | | |
| | —$R^6C$=$CR^7$ | | | | | |
| 30 (L) | —$(CH_2)_aSH$ | | | | | |
| 7h (L) 7i (D) | (indole structure) | — | H | H | — | 1 |
| 7j (L) | (Boc-NH-benzyl structure) | — | H | H | — | 1 |
| 7k (L) 7l (D) | (cyclopentenyl-methyl structure) | — | H | H | — | 1 |

TABLE 1-continued

Compounds of Formula I

[Structure: R¹-C(=O)-NH-C(R³)(H)-[CH₂]ₙ-CH(R⁴)-O-C(=O) forming a lactone ring]

| Cmpd | R¹ | R² | R³ | R⁴ | R⁵ | n |
|---|---|---|---|---|---|---|
| 7m (L) | Boc-NH-(CH₂)₄-~ | — | H | H | — | 1 |
| 7n (L) | Ethyl (E)-but-2-enoate group (EtO-C(=O)-CH=CH-CH₂-~); A-substituted phenyl-(CH₂)q-~ where A = H, F, Cl, Br, I | — | H | H | — | 1 |
| 7o (L) | 4-Br-C₆H₄-CH₂-~ | — | H | H | — | 1 |
| 7p (L) | Ph-CH=CH-CH₂-~ | — | H | H | — | 1 |
| 7q (L) 7r (D) | Ph-(CH₂)₃-~ | — | H | H | — | 1 |
| 8f (L) 8g (D) | —(CH₂)COR² | | Ph-CH₂-~ | H | H | — | 1 |
| 14 (L) | N-Boc-pyrrolidin-2-yl-~ | — | H | H | — | 1 |
| 50 (L) | —CH(CH₃)₂CH₂CH₃ | — | —CH₂CH₃ | —CH₂— | I | 1 |
| 51 (D) | —(CH₂)₂C₆F₆ | — | H | H | — | 1 |

TABLE 1-continued

Compounds of Formula I

| Cmpd | R¹ | R² | R³ | R⁴ | R⁵ | n |
|---|---|---|---|---|---|---|
| 53 | 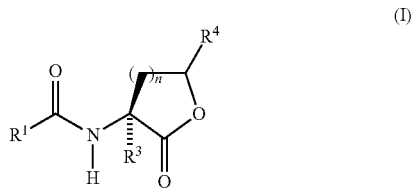 | — | H | —CH₂— | (N-piperazinyl) | 2 |
| 54 (L) | —(CH₂)₃CH₃ | — | —CH₃ | —CH₂— | I | 1 |
| 55 | —(CH₂)COR² | —(CH₂)₂CH₃ | H | —CH₂— | —N(CH₃)₂ | 2 |
| 56 | —(CH₂)₂HC=CH(CH₂)₃CH₃ | — | —CH₃ | —CH₂— | 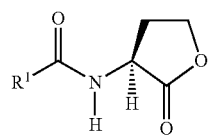 | 2 |
| 57 (L) | —CH₂CH(CH₃)₂ | — | H | —CH₂— | —N(CH₂HC=CH)₂ | 1 |
| 58 (L) | (cyclopropyl) | — | H | H | — | 1 |
| 59 (L) | —CH₂(CF₂)₄F₃ | — | H | H | — | 1 |

In other preferred embodiments, the present invention provides combinatorial libraries of autoinducer analogs. In certain embodiments, the invention provides a combinatorial library of two or more compounds of Formula (I).

(I)

where n is 1, 2 or 3, wherein if n=1, the ring C bound to the substituted amino can be a chiral center, R¹ is selected from —H, —(CH₂)$_a$CH₃, —(CH₂)$_a$COR², —(CH₂)$_a$CHOHR², —(CH₂)$_a$R⁶, —O—(CH₂)$_a$CH₃, —(CH₂)$_a$HC=CH, —HC=CH(CH₂)$_a$CH₃, —(CH₂)$_a$HC=CH(CH₂)$_b$CH₃, —R⁶HC=CHR⁷, —R⁶C≡CR⁷, substituted and unsubstituted C₃-C₈ cycloalkyl, substituted and unsubstituted C₃-C₈ aryl, three to eight member substituted and unsubstituted heterocyclic rings, where the heteroatom is at least one of O, S or N, R² is selected from —H, —(CH₂)$_a$CH₃, substituted and unsubstituted C₃-C₈ cycloalkyl, substituted and unsubstituted C₃-C₈ aryl, three to eight member substituted and unsubstituted heterocyclic rings, where the heteroatom is at least one of O, S or N, R³ is selected from —H, —CH₂CH₃, —CH₃, R⁴ is selected from —H, —CH₂—, R⁵ is —H, R⁶ and R⁷ are the same or different, selected from —H, substituted and unsubstituted C₃-C₈ cycloalkyl, substituted and unsubstituted C₃-C₈ aryl, three to eight member substituted and unsubstituted heterocyclic rings, where the heteroatom is at least one of O, S or N, and a and b are independently integers from 0 to 15.

In certain embodiments, the compound has the formula:

where R¹ is —CH₂COR², C₆H₁₃,

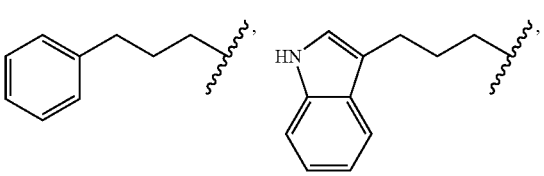

-continued

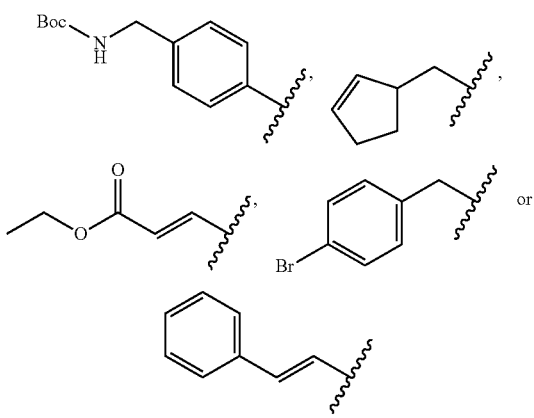

and
R² is

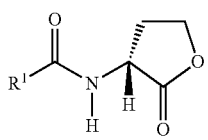

In other embodiments, the compound has the formula:

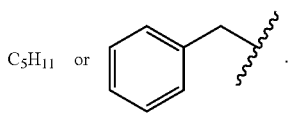

where R¹ is —CH₂COR² or

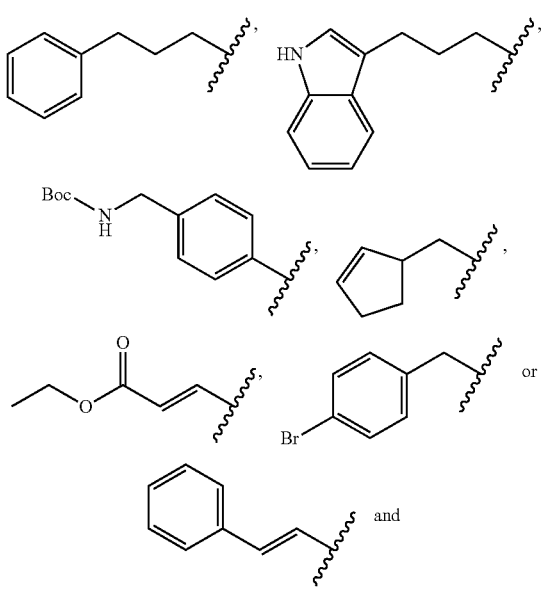

R² is

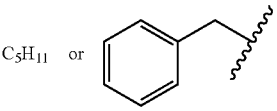

In various exemplary embodiments, this invention separately provides methods for the synthesis of AHL analogs that are solid phase syntheses as described in Schemes I-III.

In some other exemplary embodiments, this invention provides methods for the efficient synthesis of AHL analogs that are produced with high purity and yield. In various exemplary embodiments, AHL analogs synthesized by the methods described herein are synthesized in a short period of time.

This invention separately provides a method for the synthesis of both naturally occurring and non-naturally occurring AHL analogs. In various other exemplary embodiments, the invention provides methods for the efficient synthesis of AHL ligand libraries. In various exemplary embodiments, the AHL analog library is a combinatorial library. In still other exemplary embodiments, the AHL analogs produced by the methods disclosed herein can separately include both agonists and antagonists.

This invention separately provides methods for the efficient screening of AHL analogs. In various exemplary embodiments the screening methods described herein include reporter gene assays and biofilm production assays.

This invention separately provides compositions and methods for the manipulation and perturbation of the bacterial quorum-sensing pathway. In various exemplary embodiments AHL analogs described herein may compete with native AHL ligands inhibiting biofilm formation. In various other exemplary embodiments the AHL prematurely stimulate biofilm production.

In various exemplary embodiments, the invention provides methods for inhibiting and/or attenuating the virulence of quorum sensing bacteria by interfering with the quorum sensing pathway and reducing and/or inhibiting the production of biofilms, virulence factors and/or enzymes by quorum sensing bacteria.

In various other exemplary embodiments, this invention provides compounds and methods for use in agriculture to inhibit/modulate and/or encourage the growth and infectivity bacteria.

In yet other exemplary embodiments, this invention separately provides compounds and methods for their use where biofouling has an economic impact such as in paper making, water treatment and power generation.

Other objects, features and advantages of the present invention will become apparent from the following detailed description. It should be understood, however, that the detailed description and the specific examples, while indicating exemplary embodiments of the invention, are given by way of illustration only, since various changes and modifications within the spirit and scope of the invention will become apparent to those skilled in the art from this detailed description.

BRIEF DESCRIPTION OF THE DRAWINGS

(FIG. 34A) untreated, (FIG. 34B) compound 7h and (FIG. 34C) compound 7o.

FIG. 35A. untreated. FIG. 35B. Compound 7h. FIG. 35C. Compound 7o.

FIG. 36A. untreated. FIG. 36B. 50 μM compound 7o. FIG. 36C. 25 μM compound 7o. FIG. 36D. 12.5 μM compound 7o.

FIG. 37A. 50 μM compound 7h. FIG. 37B. 25 μM compound 7h. FIG. 37C. 12.5 μM compound 7h.

DESCRIPTION OF THE PREFERRED EMBODIMENTS

Figure 1A:
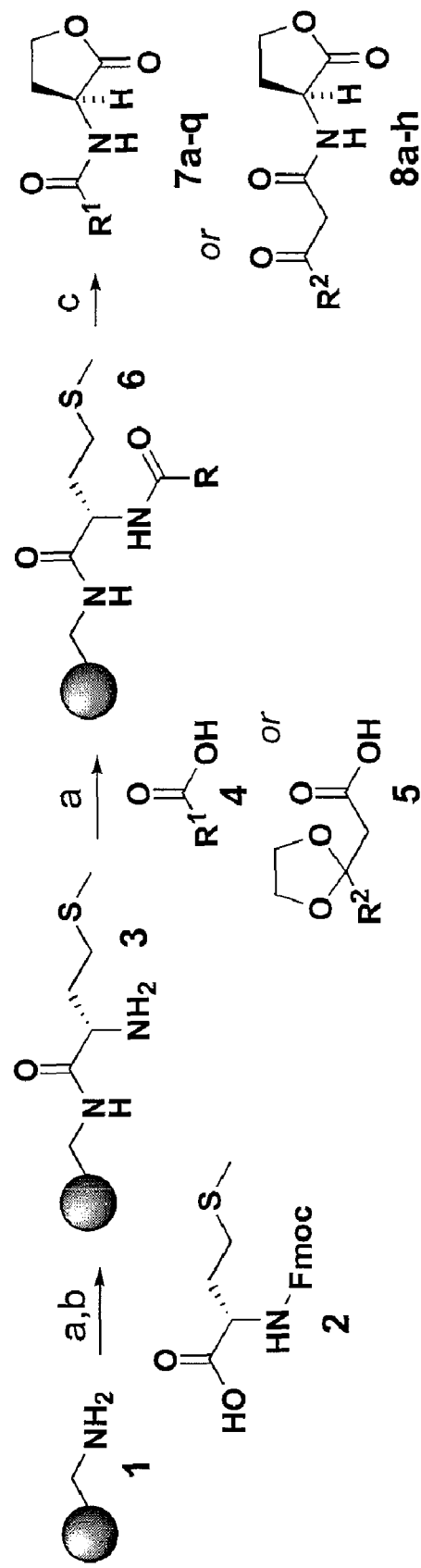
FIG. 1A is a schematic diagram illustrating Scheme I for the synthetic production of AHLs, where a=DIC, HOBT, CHCl₃/DMF, microwave 50° C. (2×10 minutes); b=DMF, microwave 150° C., 7 minutes; c=CNBr, TFA, CHCl₃/H₂O, microwave 60° C., 30 minutes.

Many bacterial phenotypic traits are modulated in response to bacterial density that is detected by quorum sensing. These phenotypes have important health consequences in pathogenic bacteria and include virulence, carbapenem antibiotic production, biofilm formation, enzyme synthesis and secondary metabolite synthesis. Modulation or interruption of these signaling pathways can alter the life-cycle of quorum-sensing bacteria and thereby alter their virulence. Other quorum sensing bacteria also have important economic impact in such industries as agriculture, water treatment and power generation.

The quorum sensing system can be manipulated at both the level of the autoinducer and its receptor. Studies have shown that both biofilm formation and expression of other virulence factors has been inhibited by mutating or deleting the receptor, as well as the AI. Therefore, by synthesizing non-native AIs, or AHL, analogs, a similar ability to delete or attenuate microbial virulence can be achieved. Moreover, an efficient method for producing such synthetic analogs provides the opportunity to create a library of autoinducers without using the time-consuming tools of molecular biology to mutate naturally occurring AHLs. Not only does such a method allow for a more rapid and efficient method to create such a library but it also allows the production of AHL analogs that are not per se based on a native model. Further, the use of non-naturally occurring AHL analogs may provide compounds that stimulate quorum sensing pathways in an attenuated manner, bind with different affinities and result in a steric hindrance for the receptor when binding to the promoter thereby eliciting different phenotypic responses.

Generally, there are at least three components to quorum sensing: (1) a receptor/transcription factor; (2) a diffusible signal, the autoinducer (AI); and (3) a recognition site in the promoter of the target gene. The general model for quorum sensing requires a membrane associated activator or transcription factor (LuxR), a cis-acting inverted repeat called the lux box in the promoter region of the gene and the AI, an N-acyl-homoserine lactone (AHL). In *V. fischeri*, the lux genes are responsible for bioluminescence and are transcribed at a low level. Small amounts of AHL diffuse out of the cell and collect in the environment. At high cell densities the AHL accumulates and binds to the receptor/activator presented on the cell membrane. This forms a complex that is internalized, allowing the activator/transcription factor to bind to the lux box, increasing and amplifying the production of the AI and resulting in a cascade effect and increased transcription of the AI.

The ability to modulate or disrupt the quorum sensing system presents novel opportunities to affect the metabolic pathways during the bacterial life cycle and thus, the pathogenesis of the quorum-sensing bacteria. By compiling a library of AHL ligands the binding affinities of naturally occurring and non-natural AHL ligands can be explored. Various strategies used to exploiting such compounds include using AHL analogs that inhibit binding of the native ligand without stimulating quorum-sensing pathways; utilizing ligands that prematurely initiate internalization triggering quorum sensing pathways; and using ligands that initiate internalization but inhibit binding of the receptor to the promoter.

The pathogenicity of quorum sensing bacteria can be attenuated or eliminated by inhibiting or reducing the microbe's ability to respond to quorum sensing signals with virulence factors such biofilms. Virulence factors can be inhibited by adding synthetic AHL analogs, to a suspected bacterial bloom. In various exemplary embodiments the analog can be administered in an aqueous solution. By preventing the formation of biofilm formation antibodies, cells of the immune response and antibiotics are allowed to access to bacteria thereby increasing the ability of a host to fight infections. Other strategies include initiating the production of biofilm matrices, before the bacteria are dense enough to produce an exclusionary biofilm allowing the host to mount a more effective immune response while the bacteria remain accessible. In addition, identification of synthetic ligands that bind the receptor with greater or less affinity than the native ligand presents opportunities to inhibit binding of the receptor to the target promoter.

In one exemplary embodiment, the present invention provides quorum sensing compounds comprising naturally occurring AHL ligands and non-natural AHL analogues synthesized by the methods described herein and include:

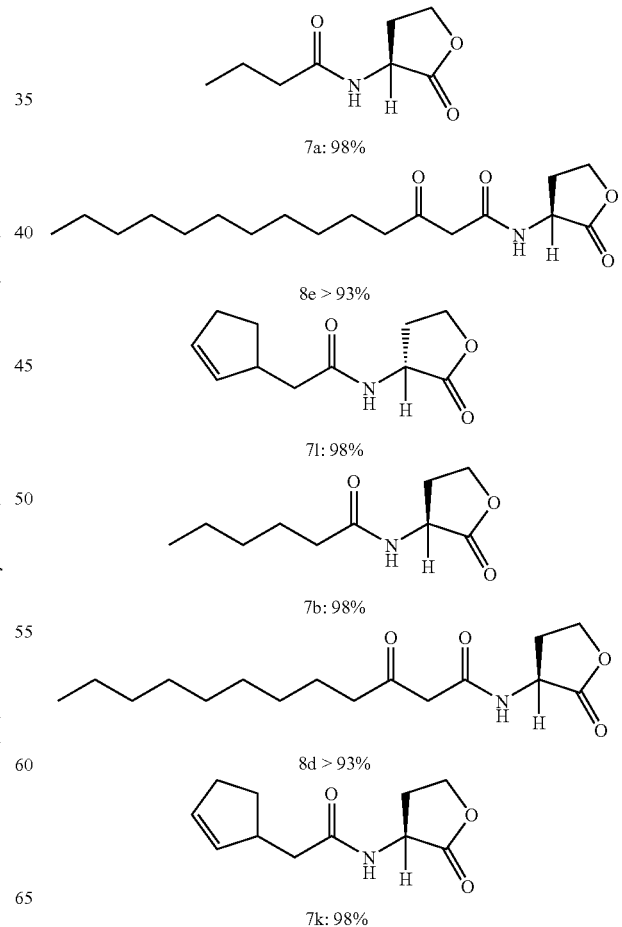

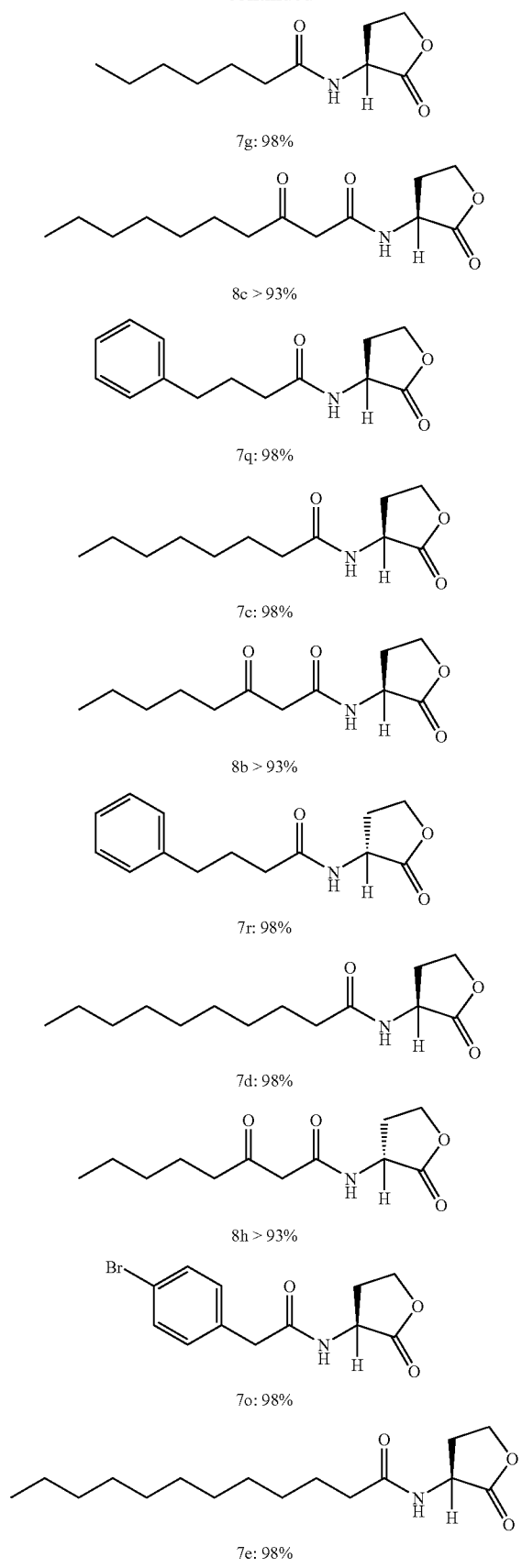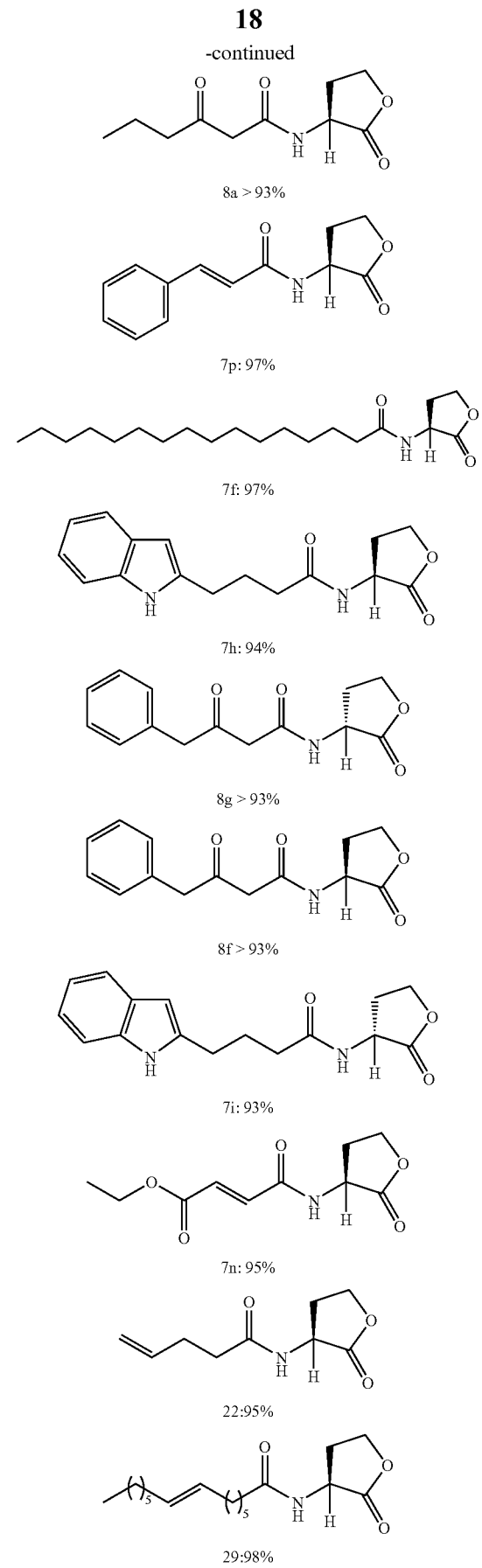

-continued
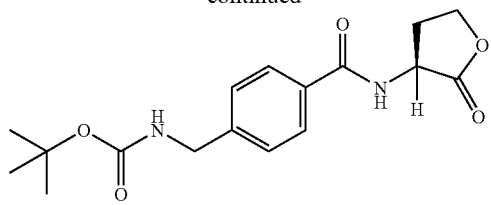
7j > 93%
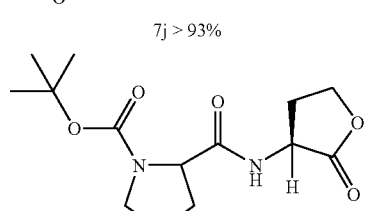
14 > 93%
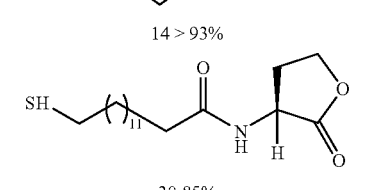
30:85%
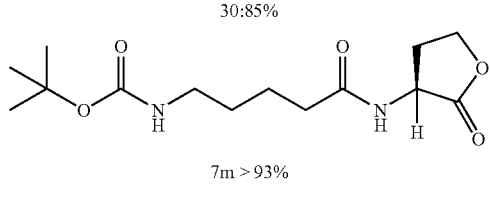
7m > 93%
These compounds are generally synthesized as shown in SCHEME 1 (FIG. 1A).
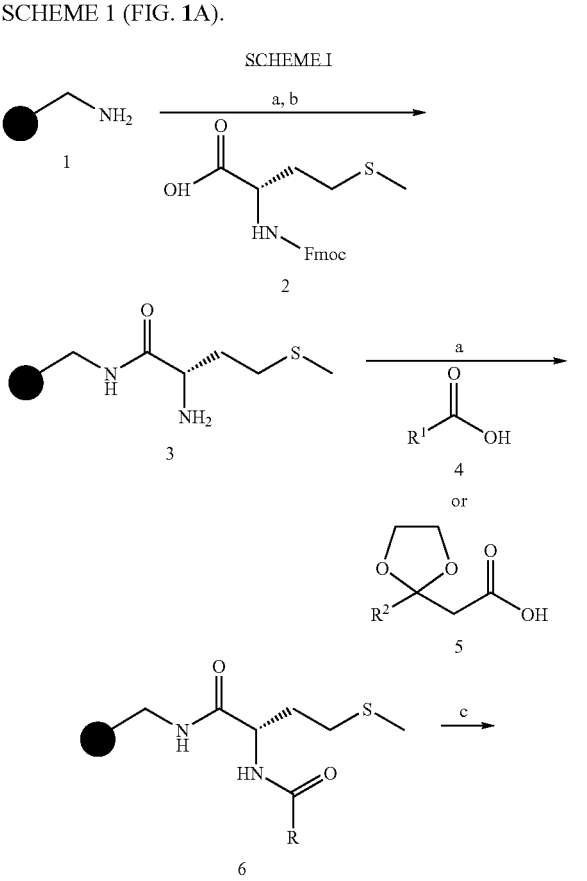
-continued
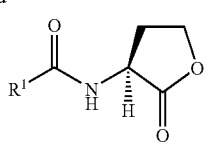
7a-q
or
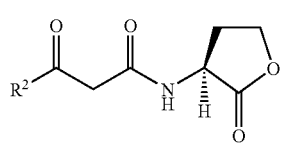
8a-h
where a=DIC, HOBT, CHCl3DMF, microwave 50° C. (2×10 min); b=DMF, 5 microwave 150° C., 7 min; c=CNBr, TFA, CHCl$_3$/H$_2$O, microwave 60° C., 30 min. In another exemplary embodiment, the compounds disclosed herein include:
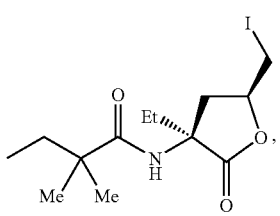
50
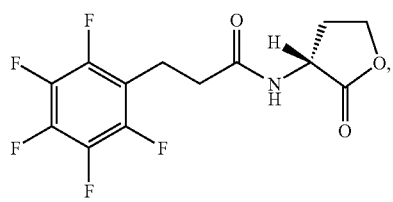
51
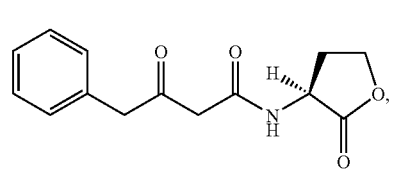
8f
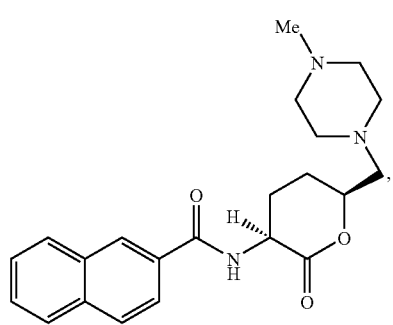
53

21
-continued

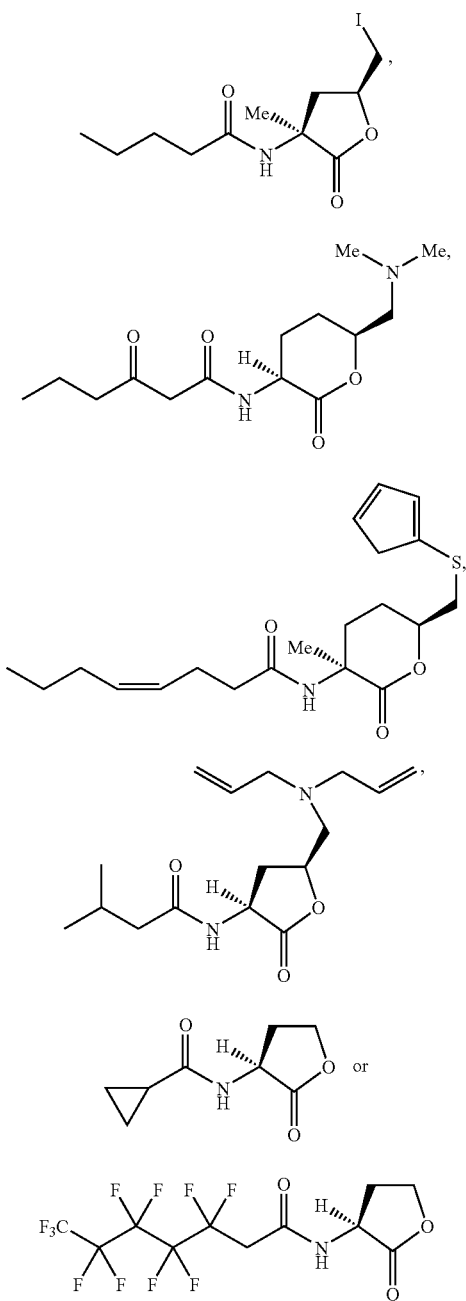

Figure 1B:
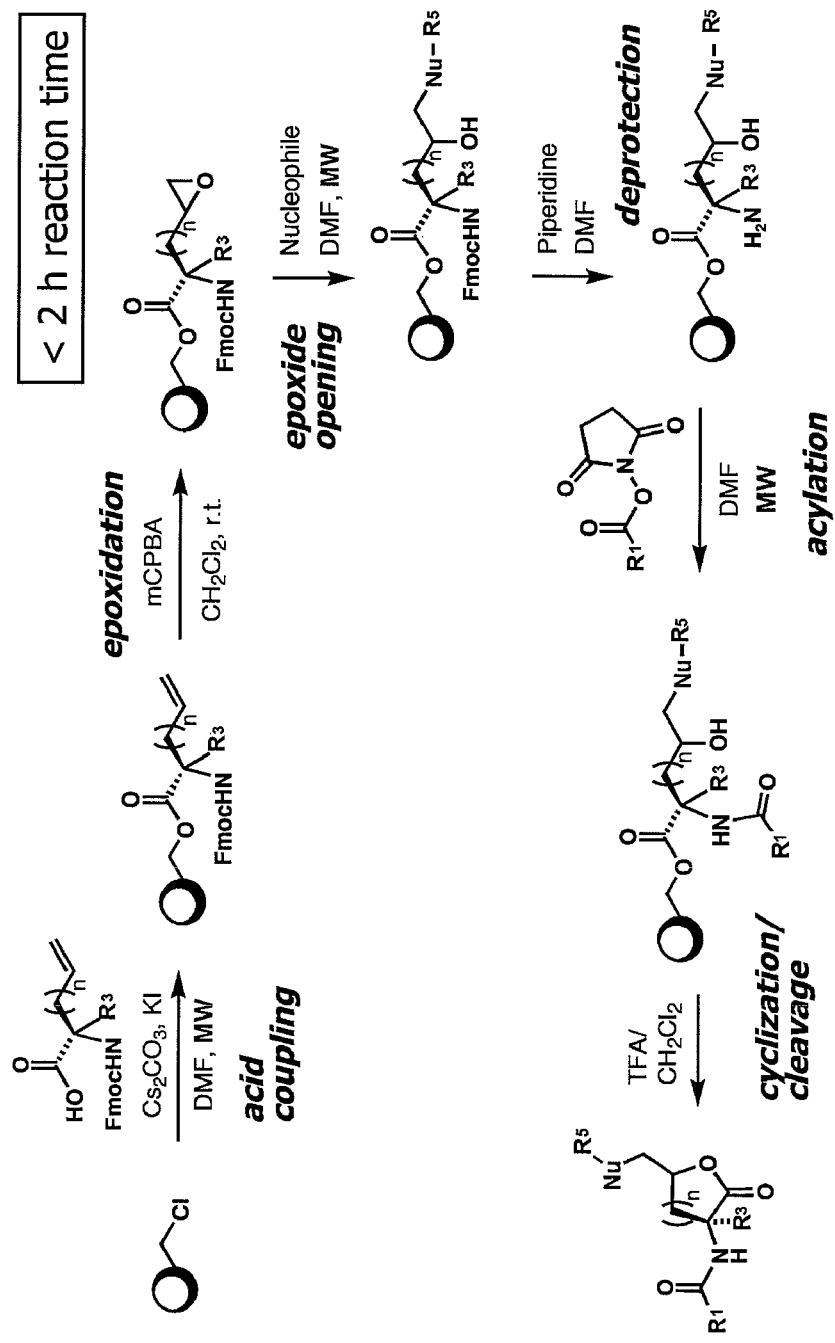
FIG. 1B is a schematic diagram illustrating Scheme II for the synthetic production of quorum sensing compounds.

Such compounds are generally synthesized as shown in SCHEME II (FIG. 1B).

SCHEME II

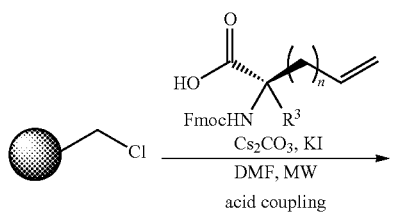

22
-continued

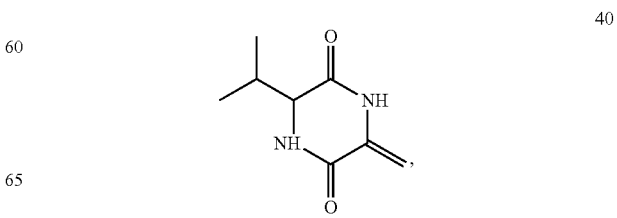

In preferred embodiments, the method illustrated by Scheme II comprises the steps of providing a halide derivatized substrate, preferably a chloride derivatized substrate, acid coupling, epoxidation, epoxide opening, deprotection, acylation, cyclization an deleavage from the substrate.

In yet another exemplary embodiment, the quorum sensing compounds disclosed herein include:

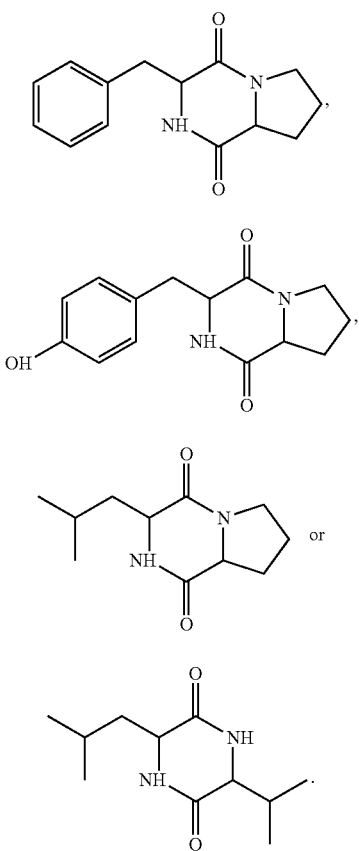

Figure 1C:
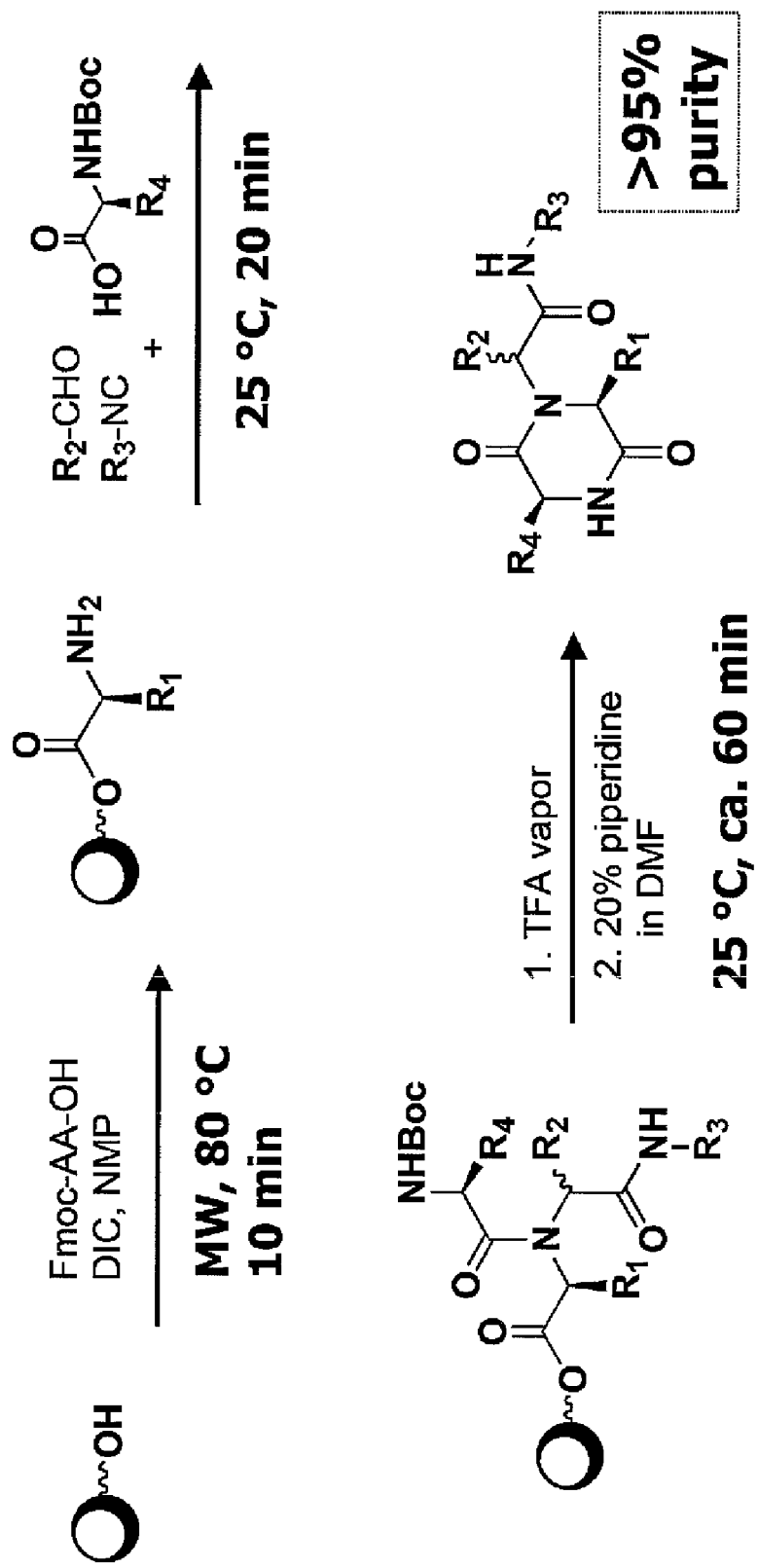
FIG. 1C is a schematic diagram illustrating Scheme III for the synthetic production of quorum sensing compounds.

These compounds are generally synthesized by the method shown in SCHEME III (FIG. 1C).

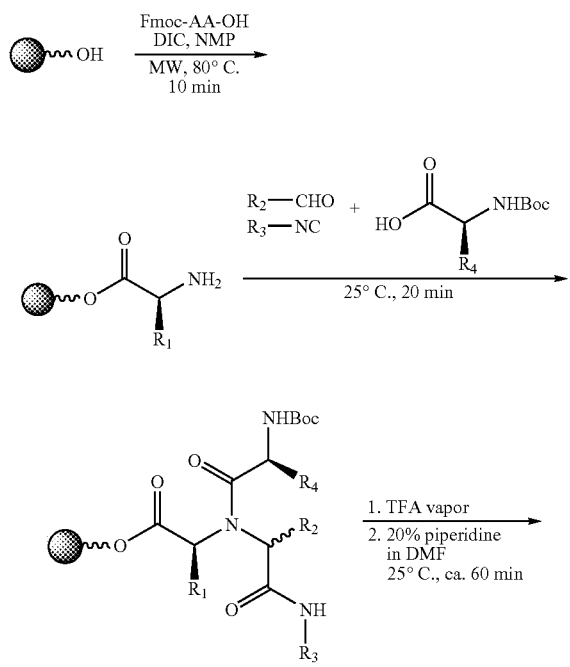

SCHEME III

>95% purity

In various exemplary embodiments, the invention described herein provides a method of regulating microbial population density comprising the step of contacting a microbe with a quorum sensing compound as shown above. Contacting may occur in numerous ways.

As defined herein, "contacting" means that the quorum sensing compound used in the present invention is introduced into a sample containing the receptor in a test tube, flask, tissue culture, chip, array, plate, microplate, capillary, or the like, and incubated at a temperature and time sufficient to permit binding of the quorum sensing compound to a receptor. Methods for contacting the samples with the quorum sensing compound or other specific binding components are known to those skilled in the art and may be selected depending on the type of assay protocol to be run. Incubation methods are also standard and are known to those skilled in the art.

In another embodiment, the term "contacting" means that the quorum sensing compound used in the present invention is introduced into a subject receiving treatment, and the compound is allowed to come in contact in vivo.

As used herein, the term "treating" includes preventative as well as disorder remittent treatment. As used herein, the terms "reducing", "suppressing" and "inhibiting" have their commonly understood meaning of lessening or decreasing.

The present invention also provides a method of reducing virulence in a microbe comprising the step of contacting said microbe with a quorum sensing compound, as shown above.

Further, in another embodiment, the present invention provides a method of modulating biofilm formation in a microbe comprising the step of contacting said microbe with a quorum sensing compound as shown in this disclosure. The invention also provides methods of regulating microbial disease resistance or susceptibility to a microbial disease in a subject comprising the step of contacting said microbe with a quorum sensing compound.

In certain embodiments, the present invention encompasses administering the compounds useful in the present invention to a patient or subject. A "patient" or "subject", used equivalently herein, refers to a plant or an animal. In particular, an animal refers to a mammal, preferably a human. The subject either: (1) has a pathogen remediable or treatable by administration of a quorum sensing compound; or (2) is susceptible to a pathogen that is preventable by administering a quorum sensing compound.

The present invention also provides a method of synthesis of a quorum sensing compound, comprising the steps shown in any of SCHEMES I-III.

The compounds shown above, or compounds made using the synthesis steps shown in SCHEMES I-III have industrial uses as well. For example, in industries where biofouling occurs, such as, for example, paper making, power generating and water treating, equipment and/or machinery subject to biofilms can be treated with quorum sensing antagonists to prevent biofilm formation. Such treatment can include spraying or painting the susceptible machinery, component or instrument with a quorum sensing compound or maintaining an effective concentration of a quorum sensing compound in a wash step or effluent step.

Bacteria affecting crops include beneficial species such as those of the *Rhisobium* genus and other related agriculturally important bacteria such as *Sinorhizobium melilotii* and *Bradyrhizobium japonicum*. Detrimental quorum sensing bacteria, such as species of *Erwinia* are is responsible for the soft rot of crops including carrots, potatoes, apples, pears and maize. Still other crop pathogens *Ralstonia solanacearum* (tomato and tobacco); *Xanothmonas campestris pathovars* (peppers and tomatoes); and *Pseudomonas syringae pathovars* (tomato, arabidopsis, legumes).

According to some exemplary embodiments of this invention, beneficial bacteria, such as *Rhizobium* can be encouraged to form symbiotic relationships with crops by treating soil, fertilizer or the like and applying an effective amount of a quorum sensing compound to the crops or tilling it into the soil. Similarly, destructive bacteria can be inhibited from attacking crop plants by applying a quorum sensing antagonist to the crops during growth, by treating the soil or applying as a spray. The crops can also be treated during harvest or distribution by applying a quorum sensing compound. Similar methods are used to encourage ripening of fruit by treatment with ethylene glycol.

Further, it should be appreciated that, in some exemplary embodiments, it may be desirable to treat a component, surgical instrument, machinery, food crop or the like with more than one quorum sensing compound. For example, when conditions may allow various pathogens to grow, it may be desirable to treat the area with a cocktail or mixture of quorum sensing compounds such that optimum compound is utilized for each suspect bacteria. In some embodiments, such quorum sensing compounds may all be inhibitory. In other embodiments some quorum sensing compounds could be inhibitory and some could be stimulatory. For example, in agriculture, a compound could be applied to the soil, much as fertilizer is that would encourage growth of nitrogen fixing bacteria while inhibiting the growth of various rot-causing bacteria. In some embodiments the quorum sensing compound may be applied in a prophylactic manner.

The present invention, thus, generally described, will be understood more readily by reference to the following examples, which are provided by way of illustration and are not intended to be limiting of the present invention.

EXPERIMENTAL BACKGROUND

Various exemplary embodiments of methods according to this invention are described in the following illustrative examples. In these examples, specific products identified by Arabic numerals (e.g., 1, 2, 3, etc.) refer to the specific structures so identified in the following description and synthesis route shown in SCHEME I (FIG. 1A). The present invention describes methods to synthesize AI analogs comprising both AHL agonists and antagonists and thereby create a combinatorial AHL library. In addition, the invention provides methods to screen novel quorum sensing compounds and assay their ability to interact and/or bind with the receptor/activator.

To meet these challenges, a solid-phase synthetic route to both natural and non-natural AHLs (Scheme 1) was developed. The solid-phase methods were chosen because they routinely give improved product purity relative to solution-phase methods, and enable combinatorial library construction (Ley, S. V.; Baxendale, I. R. *Nat. Rev. Drug. Discov.* 2002, 1, 573-586). To date, the use of combinatorial methods to systemically evaluate AHL analogs remains essentially unexplored. To further expedite both solid-phase and library synthesis, microwave (microwave)-assisted reactions were incorporated throughout the route (Blackwell, H. E. *Org. Biomol. Chem.* 2003, 1, 1251-1255; Kappe, C. O. *Angew. Chem. Int. Ed.* 2004, 43, 6250-6284). The four-step synthetic approach developed (SCHEME I) entails first loading amino polystyrene resin (1) with N-Fmoc-L-methionine (2) using a microwave-assisted carbodiimide coupling (DIC) (microwave-assisted reactions were performed in a commercial microwave reactor available from, for example, Milestone, Inc. Shelton, Conn.). Next, thermal Fmoc group removal was followed by a second microwave-assisted DIC coupling with various carboxylic acids (4) or protected β-keto-acids (5) using established procedures (Rathke, M. W.; Nowak, M. A. *Synth. Commun.* 1985, 15, 1039-1049) to generate acylated resin 6. Finally, the classical reaction of cyanogen bromide (CNBr) with L-methionine was used in a microwave-assisted, tandem cyclization-cleavage step to release AHLs 7 and 8 from the solid-support (Ko, D. H.; Kim, D. J.; Lyu, C. S.; Min, I. K.; Moon, H.-s. *Tetrahedron Lett.* 1998, 39, 297-300 (b) Kappel, J. C.; Barany, G. *J. Comb. Chem.* 2005, 7, 78-84, and references therein).

Microwave-Assisted Solid-Phase Synthetic Route to Natural and Non-Natural AHLs

The solid-phase route to AHLs is significant because it is the first to provide access to the ca. 15 known natural AHLs from Gram-negative bacteria as well as access to structural analogs thereof. Further, the route delivers compounds in sufficient purity and quantity for biological research. As a test, the inventors synthesized the majority of the natural AHLs (7a-f, 8a-e) in good yields and excellent purities in under 60 minutes total reaction time (Table 2). AHLs 8b, N-3-oxo-octanoyl L-homoserine lactone, (OOHL) and 8d, N-3-oxo-dodecanoyl L-homoserine lactone, (ODHL) were required as critical control molecules for biological work with *Agrobacterium tumefaciens* and *P. aeruginosa*, respectively (Examples 38-42). The high purities and shortened reaction times accessible using this approach underscore the value of microwave-assisted solid-phase chemistry for AHL synthesis. Table 2 lists the naturally occurring AHL's synthesized by the route shown in SCHEME I (FIG. 1A), the organism that is its natural source, the percent purity and yield.

TABLE 2

Naturally Occurring AHLs Synthesized via SCHEME I

| compound | $R^1$ or $R^2$ | organism | purity [%]$^{a,b}$ | yield [%]$^c$ |
|---|---|---|---|---|
| 7a | $C_3H_7$ | *P. aeruginosa* | 98 | 65 |
| 7b | $C_5H_{11}$ | *R. leguminosarum* | 98 | 64 |
| 7c | $C_7H_{15}$ | *Y. pseudotuberculosis* | 98 | 76 |
| 7d | $C_9H_{19}$ | *B. pseudomallei* | 97 | 80 |
| 7e | $C_{11}H_{23}$ | *S. meliloti* | 98 | 70 |
| 7f | $C_{13}H_{27}$ | *R. capsulatus* | 97 | 64 |
| 8a | $C_3H_7$ | *V. fischeri* | >93 | 63 |
| 8b: OOHL$^d$ | $C_5H_{11}$ | *A. tumefaciens* | >93 | 65 |
| 8c | $C_{57}H_{15}$ | *V. anguillarum* | >93 | 76 |
| 8d: ODHL$^e$ | $C_9H_{19}$ | *P. aeruginosa* | >93 | 62 |
| 8e | $C_{11}H_{23}$ | *S. meliloti* | >93 | 62 |

$^a$Purities of 7a-f determined by integration of GC spectra.
$^b$Purities of 8a-e determined by $^1$H NMR.
$^c$Isolated yields.
$^d$N-3-oxo-octanoyl L-homoserine lactone.
$^e$N-3-oxo-dodecanoyl L-homoserine lactone.

The solid-phase route of SCHEME I was used for the parallel synthesis of a library of non-natural AHLs used as test compounds (7g-q, 8f-h). The acyl substitutents and stereochemistry of the AHL products were chosen to probe broadly the sterics and functionality present in the AHL binding site of LuxR-type proteins, as revealed in a recent X-ray structure of TraR from *A. tumefaciens*. Zhang, R. G.; Pappas, T.; Brace, J. L.; Miller, P. C.; Oulmassov, T.; Molyneaux, J. M.; Anderson, J. C.; Bashkin, J. K.; Winans, S. C.; Joachimiak, A. *Nature* 2002, 417, 971-974. The synthetic route proved robust and delivered the non-native AHLs in good yields (ca. 70%) and high purities (>93%) (Table 3).

TABLE 3

Non-Natural AHLs Synthesized via SCHEME 1.

| compound | $R^1$ or $R^2$ | stereochemistry[a] | Purity[b,c] [%] | yield[d] [%] |
|---|---|---|---|---|
| 7g | $C_6H_{13}$ | L | 98 | 81 |
| 7h | (indol-3-yl)propyl | L | 94 | 61 |
| 7i | (indol-3-yl)propyl | D | 93 | 52 |
| 7j | Boc-NH-CH2-(p-phenyl)methyl | L | 93 | 74 |
| 7k | (cyclopent-2-en-1-yl)ethyl | L | 98 | 51 |
| 7l | (cyclopent-2-en-1-yl)ethyl | D | 97 | 54 |
| 7m | Boc-NH-pentyl | L | >93 | 64 |
| 7n | ethyl (E)-but-2-enoate | L | 93 | 47 |
| 7o | (4-bromophenyl)methyl | L | 98 | 65 |
| 7p | (E)-cinnamyl | L | 93 | 76 |
| 7q | 3-phenylpropyl | L | 95 | 56 |
| 7r | 3-phenylpropyl | D | 95 | 62 |
| 8f | benzyl | L | >90 | 59 |
| 8g | benzyl | D | >90 | 64 |
| 8h | $C_5H_{11}$ | D | >93 | 54 |

[a]Determined by the N-Fmoc methionine (2) starting material
[b]Purities of 7g-h, 7l-m, and 7o-r determined by integration of GC spectra (flame ionization and MS detection).
[c]Purities of 7i-k, 7n m and 8f-h determined by $^1$H NMR analyses.
[d]Isolated yield.

Synthesis Steps: General Experimental Information $^1$H NMR and $^{13}$C NMR spectra were recorded on a Bruker AC-300 spectrometer in deuterated solvents at 300 MHz and 75 Hz, respectively. Chemical shifts are reported in parts per million (ppm, δ) using tetramethyl silane (TMS) as an internal reference (0.0 ppm). Couplings are reported in hertz. Electrospray ionization (ESI) MS were obtained using a Shimadzu LCMS-2010 system (Columbia, Md.) equipped with two pumps (LC10ADvp), controller (SCL-10Avp), autoinjector (SIL-10ADvp), UV diode array detector (SPD-M10Avp), and single quadrupole analyzer. FT-IR and attenuated total reflectance (ATR)-IR spectra were recorded with a Bruker Tensor 27 spectrometer, outfitted with a single reflection MIRacle Horizontal ATR unit from Pike Technologies. A ZnSe crystal with spectral range 20,000 to 650 cm-I was used for ATR-IR measurements. UV spectra were recorded using an HP-8452 UV-Visible spectrometer running Chemstation software. GC-MS spectra were obtained using a Shimadzu GC-17A system (Columbia, Md.) equipped with a QP-5000 mass spectrometer. A Restek RTX-5 crossbond 95% polysiloxane GC column was used with following general GC gradient: injection temperature 300° C.; initial oven temperature 100° C.; hold 3 minutes; ramp at 20° C./minutes to 300° C.; hold 2-15 minutes for a total run time of 15-30 minutes. Optical rotations ([a]24D) were measured on a Perkin-Elmer 241 digital polarimeter at 25° C.

All reagents were purchased from commercial sources (Alfa-Aesar, Ward Hill, Mass.; Aldrich, Milwaukee, Wis.; Acros Organics, Geel, Belgium; and Sigma, St. Louis Mo.) and used without further purification. Solvents were purchased from commercial sources (Aldrich and J. T. Baker, Phillipsburg, N.J.) and used as is, with the exception of dichloromethane ($CH_2Cl_2$), which was distilled over calcium hydride immediately prior to use. All solid-phase syntheses were performed using aminomethyl polystyrene resin (Nova-Biochem, Merck, KGaA, Darmstadt, Del.) 100-200 mesh; loading 1.1-1.2 mmol/g).

Microwave Instrumentation: Solid-phase reactions were carried out using either Milestone (Shelton, Conn.) or CEM (Mathews, N.C.) commercial microwave reactors. The Milestone MicroSYNTH Labstation is a multimodal microwave synthesis reactor equipped with a continuous power source (1000 W max). This instrument was interfaced with an Ethos MicroSYNTH Lab Terminal PC running EasyWave reaction monitoring software. Using this reactor system, microwave irradiation was applied to reactions using either wattage (power) control or temperature control. The microwave reactor is equipped with a fiber-optic temperature sensor that allows direct monitoring of the internal temperature of reaction vessels, and an infrared sensor (installed in the side wall of the reactor cavity) that monitors the surface temperature of any reaction vessel inside the cavity. The system also has a rotating plate in the cavity and the capability for stirring (using magnetic stir-bars) during reactions.

The CEM Discover is a monomodal microwave synthesis reactor equipped with a 300 W (max) power source. The system has an attached Explorer automated synthesis workstation module, with four autosampler racks that each holds six samples. The instrument is interfaced with a Dell Inspiron PC running ChemDriver Discovery reaction monitoring software. Using this system, microwave irradiation can be applied to reactions using wattage, pressure, or temperature control. The CEM microwave reactor is equipped with an infrared temperature sensor positioned below the reaction vessel to control temperature. The system also has the capability for stirring (using magnetic stir-bars) during reactions.

All microwave-assisted reactions reported herein were performed using temperature control to monitor and control microwave irradiation.

Solid-Phase Library Synthesis Techniques

Solid-phase reactions were performed in either 100 mL round bottom flasks in the Milestone microwave reactor or 10 mL glass CEM microwave vessels (part #908035) in the CEM microwave reactor. Between synthesis steps, the solid-phase resin was washed with solvents stored in standard polypropylene Nalgene squirt bottles on a Vac-Man vacuum manifold (Promega, part #: A7231) using 8 mL polypropylene sample reservoirs (Alltech, part #: 210208) equipped with 20 µm fits (Alltech, part #: 211408). Liquid reagents were dispensed during synthesis using Brinkman Eppendorf pipettmen (calibrated for variable solvent delivery) equipped with disposable polypropylene pipette tips.

Synthesis of 1,3-Dioxolane Protected β-Keto Acids

The 1,3-dioxolane protected β-keto acids building blocks (5) used in this study were prepared via a modified version of the methods reported by Barnick and Rathke (Barnick, J. W. F. K.; van der Baan, J. L.; Bickelhaupt, F. *Synthesis* 1979, 79, 787-788; Rathke, M. W.; Nowak, M. A. *Synth. Commun.* 1985, 15, 1039-1049). A representative synthesis is outlined below in Examples 1-3 and illustrated in SCHEMES IV-VI.

Example 1

Synthesis of 3-Oxooctanoic Acid (10b) (SCHEME IV)

A stirred solution of bis-trimethylsilyl malonate (21.6 g, 71.5 mmol) in 100 mL of anhydrous diethyl ether was cooled to −78° C. To this solution, n-butyl lithium (1.6 M in ether, 44.7 mL, 71.5 mmol) was added slowly, keeping the temperature below −60° C. Upon completion of addition, the reaction was allowed to warm to −10° C., at which time hexanoyl chloride (5 mL, 35.75 mmol) was added quickly and allowed to stir for 30 minutes. Next, 150 mL of a cold, aq. 5% sodium bicarbonate solution was added, and the resulting solution was stirred vigorously for 30 minutes. The aq. layer was separated out and acidified with cold 4N sulfuric acid until pH=2. The aq. layer was then extracted 2×50 mL with diethyl ether, dried over MgSO$_4$, and concentrated down in vacuo to afford a white solid. This solid could be further purified by recrystallization from hexane, if necessary. 4.9 g, 87% yield. $^1$H NMR (300 MHz, CDCl$_3$) δ=3.49 (s, 2H, CH$_2$), 2.59 (t, 2H, J=7.3 Hz, CH$_2$), 1.64 (p, 2H, J=7.4 Hz, CH$_2$), 1.34 (m, 4H, CH$_2$CH$_2$), 0.92 (t, 3H, J=6.9 Hz, CH$_3$); $^{13}$C NMR (75 MHz, CDCl$_3$) δ=204.4, 182.8, 87.9, 48.1, 43.4, 31.3, 23.5, 14.1 ppm.

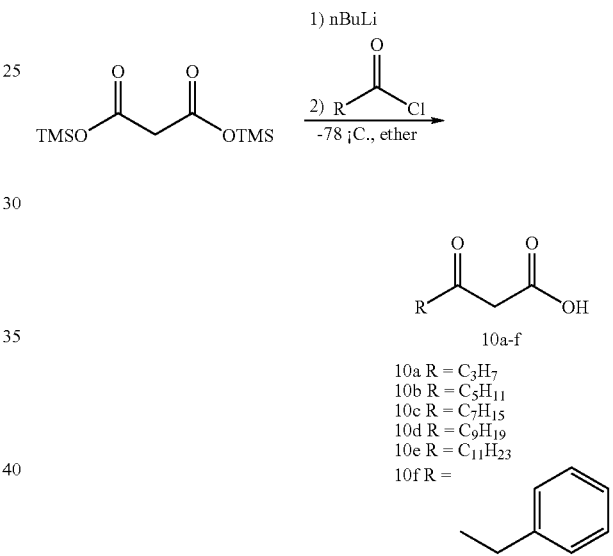

Example 2

Synthesis of Methyl-3-Oxooctanoate (11b) (SCHEME V)

To a stirred solution of 10b (5.5 g, 35 mmol) in 150 mL of a 4:1 mixture of benzene and methanol, TMSCHN$_2$ in diethyl ether (2M, 21 mL, 42 mmol) was added over a period of 10 minutes. The reaction was allowed to stir for 30 minutes, after which the reaction mixture was concentrated in vacuo to afford 11b as a yellow oil. This material was used in the subsequent step (SCHEME IV) with no further purification. 6.1 g, 95% yield. NMR (300 MHz, CDCl$_3$) δ=3.73 (s, 3H, CH$_3$) 3.44 (s, 2H, CH$_2$), 2.55 (t, 2H, J=7.3 Hz, CH$_2$), 1.64 (p, 2H, J=7.4 Hz, CH$_2$), 1.36 (m, 4H, CH$_2$CH$_2$), 0.91 (t, 3H, J=6.9 Hz, CH$_3$); $^{13}$C NMR (75 MHz, CDCl$_3$) δ=202.9, 167.9, 128.5, 52.7, 49.2, 43.2, 31.3, 23.3, 14.0 ppm.

SCHEME V

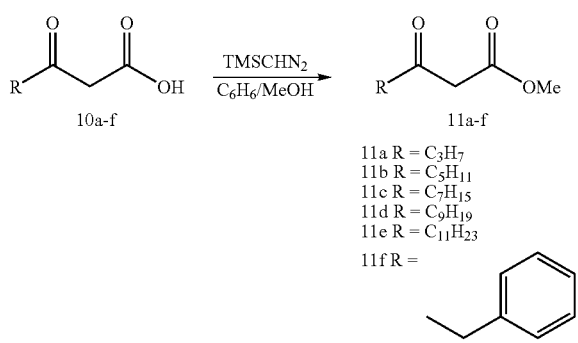

11a R = C₃H₇
11b R = C₅H₁₁
11c R = C₇H₁₅
11d R = C₉H₁₉
11e R = C₁₁H₂₃
11f R =

Example 3

Synthesis of 3,3-Ethylenedioxooctanoic Acid (5b) (SCHEME VI)

To a stirred solution of methyl-3-oxooctanoate (11b) (5.6 g, 32.5 mmol) in 125 mL of benzene, ethylene glycol (20.2 g, 325 mmol) and pTsOH (0.617 g, 3.25 mmol) was added. The flask was equipped with a condenser and Dean-Stark trap and heated to reflux for 24 h. The reaction mixture was concentrated in vacuo and diluted in 100 mL of diethyl ether. The organic layer was washed with 2×25 mL of 10% aq. NaOH, then 2×25 mL of saturated NaCl solution, dried over MgSO₄, and concentrated in vacuo to afford a clear oil. This oil was subjected to saponification by treatment with 1N NaOH (150 mL) and MeOH (75 mL) for 6 h. The basic solution was concentrated in vacuo, chilled in an ice bath, and acidified with cold concentrated HCl to a pH=2. The acidified solution was extracted with 2×75 mL of diethyl ether, dried over MgSO₄, and concentrated in vacuo to afford 3,3-ethylenedioxooctanoic acid 5b as a clear oil. 3.3 g, 50% yield. $^1$H NMR (300 MHz, CDCl$_3$) δ=4.06-3.95 (m, 4H, OCH$_2$CH$_2$O), 2.70 (s, 2H, CH$_2$), 1.83 (t, 2H, J=7.3 Hz, CH$_2$), 1.42-1.18 (m, 6H, J=7.4 Hz, (CH$_2$)$_3$), 0.94 (t, 3H, J=6.9 Hz, CH$_3$); $^{13}$C NMR (75 MHz, CDCl$_3$) δ=175.3, 109.5, 65.3, 37.8, 32.0, 22.7, 14.1 ppm.

SCHEME VI

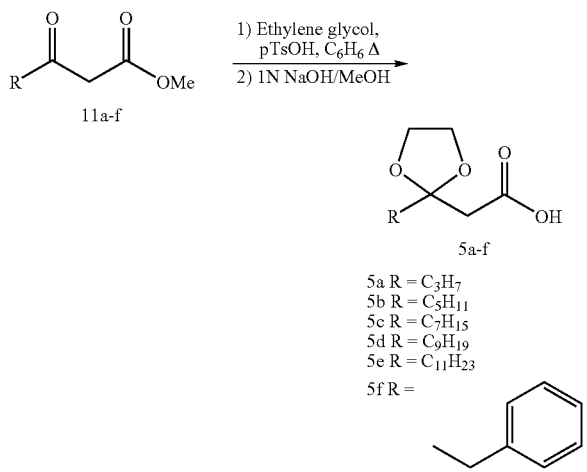

5a R = C₃H₇
5b R = C₅H₁₁
5c R = C₇H₁₅
5d R = C₉H₁₉
5e R = C₁₁H₂₃
5f R =

Example 4

Synthesis of Natural and Unnatural Acylated Homoserine Lactone Analogs Representative n-Fmoc-Methionine Resin Loading Protocol (SCHEME VII)

Aminomethyl polystyrene resin (1, 5.2 g, 6 mmol) was pre-swelled in 40 mL of CHCl$_3$ in a 100 mL round-bottom flask for 10 minutes at room temperature. In a separate flask, an activated solution of N-Fmoc-L-methionine (2, 6.7 g, 18 mmol), 1-hydroxybenzotriazole (HOBt (2.8 g, 21 mmol)), and N,N-diisopropyl-carbodiimide (DIC, 3.8 mL, 24 mmol) was prepared in 50 mL of DMF. This activated solution was stirred for 10 minutes at room temperature and then added to the swelled resin. The reaction flask was equipped with a stir-bar and sealed with rubber septum that has been pierced to allow for the insertion of the Milestone fiber optic temperature probe (in a protective sheath). The reaction flask was placed into the Milestone Microsynth Labstation and irradiated for 10 minutes at 50° C. (3 minutes ramp to 50° C. with a max of 600 W, hold 10 minutes at 50° C. with a max of 600 W). The resin then was filtered and washed with 250 mL each of DMF, water, EtOH, and CH$_2$Cl$_2$ and dried in vacuo. This coupling process was repeated 1× to yield N-Fmoc-L-methionine resin at 0.8-0.9 mmol/g loading as quantified by UV absorbance.

SCHEME VII

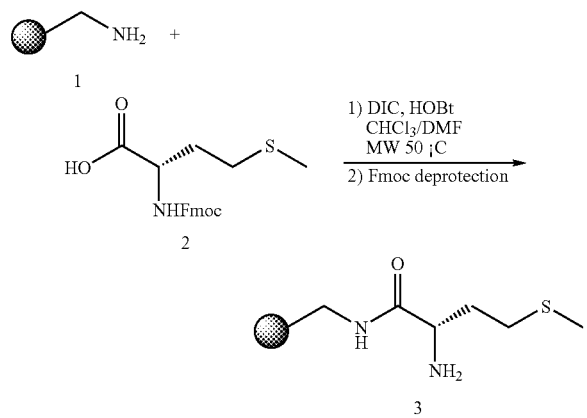

Example 5

Representative UV Fmoc Quantitation Protocol

Approximately 20 mg of N-Fmoc-L-methionine loaded resin was submersed in 3 mL of a 4% 1,8-diazabicyclo[5.4.0]undec-7-ene (DBU) solution in DMF and stirred for 30 minutes at room temperature. Thereafter, 100 μL of the solution was removed and diluted to 3.0 mL in DMF. A 1.0 mL aliquot of this solution was withdrawn and the UV absorbance was read at 296 nm ($\epsilon_{296}$=9500 M$^{-1}$ cm$^{-1}$) in a quartz cuvette; loadings were calculated according to standard methods.

Example 6

Representative Microwave-Assisted Fmoc-Deprotection Protocol

Approximately 300 mg of N-Fmoc-L-methionine loaded resin was placed in a 10 mL CEM microwave vial with 4 mL of DMF and irradiated in the CEM Discover at 150° C. for 6 minutes (300 W max. wattage). UV Fmoc-quantitation was performed as described above.

Example 7

Alternate Room Temperature Fmoc Deprotection Protocol

N-Fmoc-L-methionine loaded resin was placed into the appropriate size container and stirred with a solution of 20% piperidine/DMF solution for 30 minutes. The solution was drained and the process was repeated. UV Fmoc-quantitation was performed as described above.

Example 8

Representative Synthesis of AHLs (7a-r) (SCHEME VIII)

In a 10 mL CEM microwave vial equipped with a stir-bar, methionine resin 3 (300 mg, 0.295 mmol) was pre-swelled in 1.5 mL of $CHCl_3$ for 5 minutes at room temperature. An activated solution of carboxylic acid 4 (1.03 mmol) and DIC (1.5 mmol) was prepared in a separate vial in 2 mL of DMF and stirred for 5 minutes. The activated solution was added to the swelled resin, and the reaction mixture was subjected to microwave irradiation for 10 minutes at 50° C. (ramp time 30 sec, hold for 10 minutes at 50° C., max. wattage 300 W). The resin then was filtered and washed 2× with 50 mL each of DMF, $H_2O$, EtOH, and $CH_2Cl_2$ and dried in vacuo. To obtain the best yields, this process was repeated again. To affect compound cleavage, resin was treated with 7 mL of a 5:2 solution of 1.5 M CNBr in $CHCl_3$ and 1% aqueous TFA solution and subjected to microwave irradiation for 30 minutes at 60° C. (ramp time 60 sec, hold for 30 minutes at 60° C., max. wattage 300 W). The AHL product was eluted from the resin with 5 mL of $CHCl_3$, washed with water (3×10 mL), dried over $MgSO_4$, and concentrated in vacuo to yield the AHL as a white powder. Purities and yields for 7a-q are reported in Tables 2 and 3.

SCHEME VIII

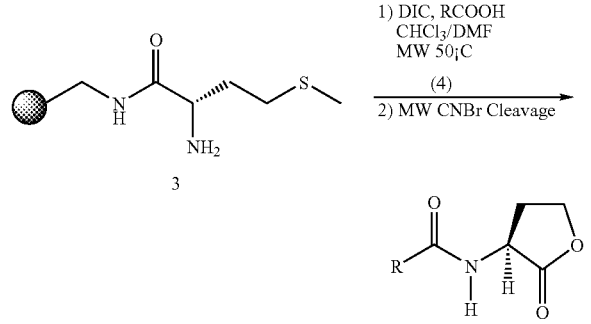

Example 9

Representative Synthesis of 3-Oxo AHLs (8a-h) (SCHEME IX)

In a 10 mL CEM microwave vial, methionine resin 3 (300 mg, 0.295 mmol) was pre-swelled in 1.5 mL of $CHCl_3$ for 5 minutes at room temperature. An activated solution of 3,3-ethylenedioxocarboxylic acid 5 (1.03 mmol) and DIC (1.5 mmol) was prepared in a separate vial in 2 mL of DMF and stirred for 5 minutes. The activated solution was added to the swelled resin, and the reaction mixture was subjected to microwave irradiation for 10 minutes at 50° C. (ramp time 30 sec, hold for 10 minutes at 50° C., max. wattage 300 W). The resin then was filtered and washed 2× with 50 mL each of DMF, $H_2O$, EtOH, and $CH_2Cl_2$ and dried in vacuo. To obtain the best yields, this process was repeated again. To effect compound cleavage, resin was treated with 7 mL of a 5:2 solution of 1.5 M CNBr in $CHCl_3$ and 1% aqueous TFA solution and subjected to microwave irradiation for 30 minutes at 60° C. (ramp time 60 sec, hold for 30 minutes at 60° C., max. wattage 300 W). AHL was eluted from the resin with 5 mL of $CHCl_3$, washed with water (3×10 mL), dried over $MgSO_4$, and concentrated in vacuo. This material was stirred for 30 minutes in 5 mL of 50% TFA/$CH_2Cl_2$ to affect β-keto deprotection. The solution was washed with water (2×5 mL), dried over $MgSO_4$, and concentrated in vacuo to yield 3-oxo AHL product as a white powder. Purities and yields for 8a-h are reported in Tables 2 and 3.

SCHEME IX

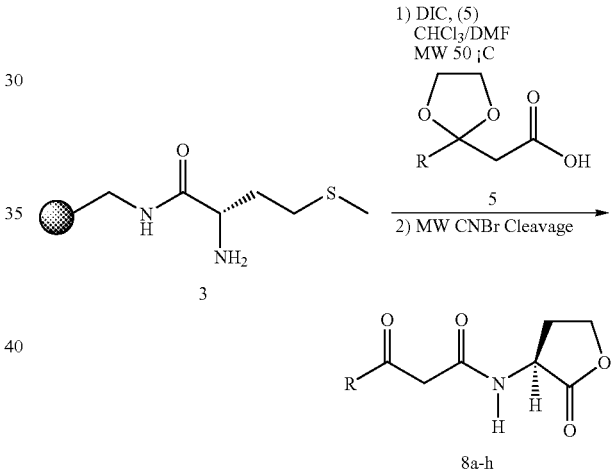

Example 10

Alternative Room Temperature Microwave Cleavage Protocol

To effect compound cleavage, resin was stirred at room temperature in 7 mL of a 5:2 solution of 1.5 M CNBr in $CHCl_3$ and 50% aqueous TFA solution for 24 h. The AHL product was eluted from the resin with 5 mL of $CHCl_3$, washed with water (3×10 mL), dried over $MgSO_4$, and concentrated in vacuo to yield the 3-oxo AHL as a white powder.

FIGS. 2 through 27 show GC-MS and/or NMR spectra (as noted) used to confirm the identity and purity of the compounds of the synthetic AHL analogs listed in Tables 2 and 3. Each of the compounds 7a-7r and 8a-8h were synthesized using the overall synthesis route illustrated in SCHEME I to provide both the naturally occurring and non-natural AHLs.

Example 11

N-butanoyl-L-homoserine lactone (7a)

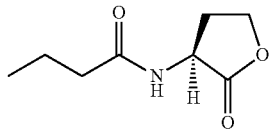

Figure 2A:
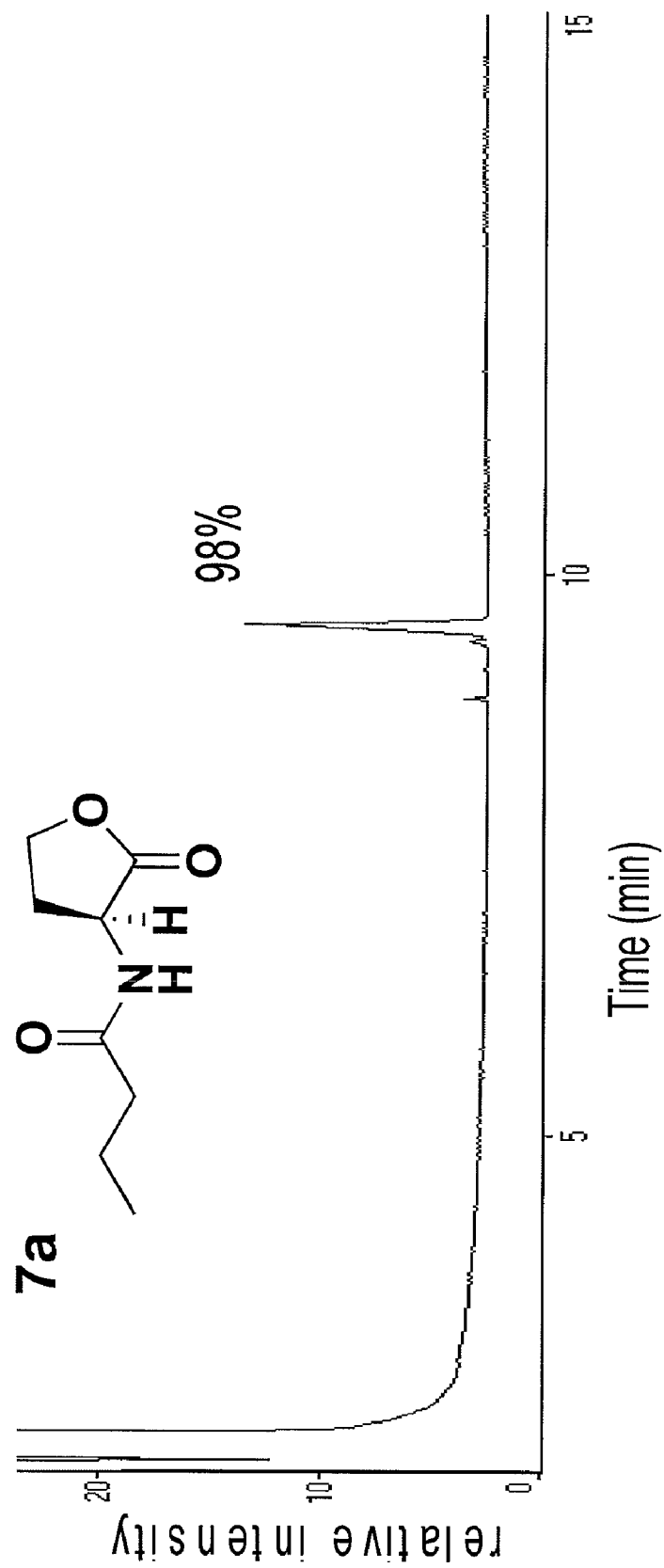
FIG. 2A shows a GC-MS spectrum and FIG. 2B shows an NMR spectrum for N-butanoyl-L-homoserine lactone (7a) produced by the scheme shown in FIG. 1A.
Figure 2B:
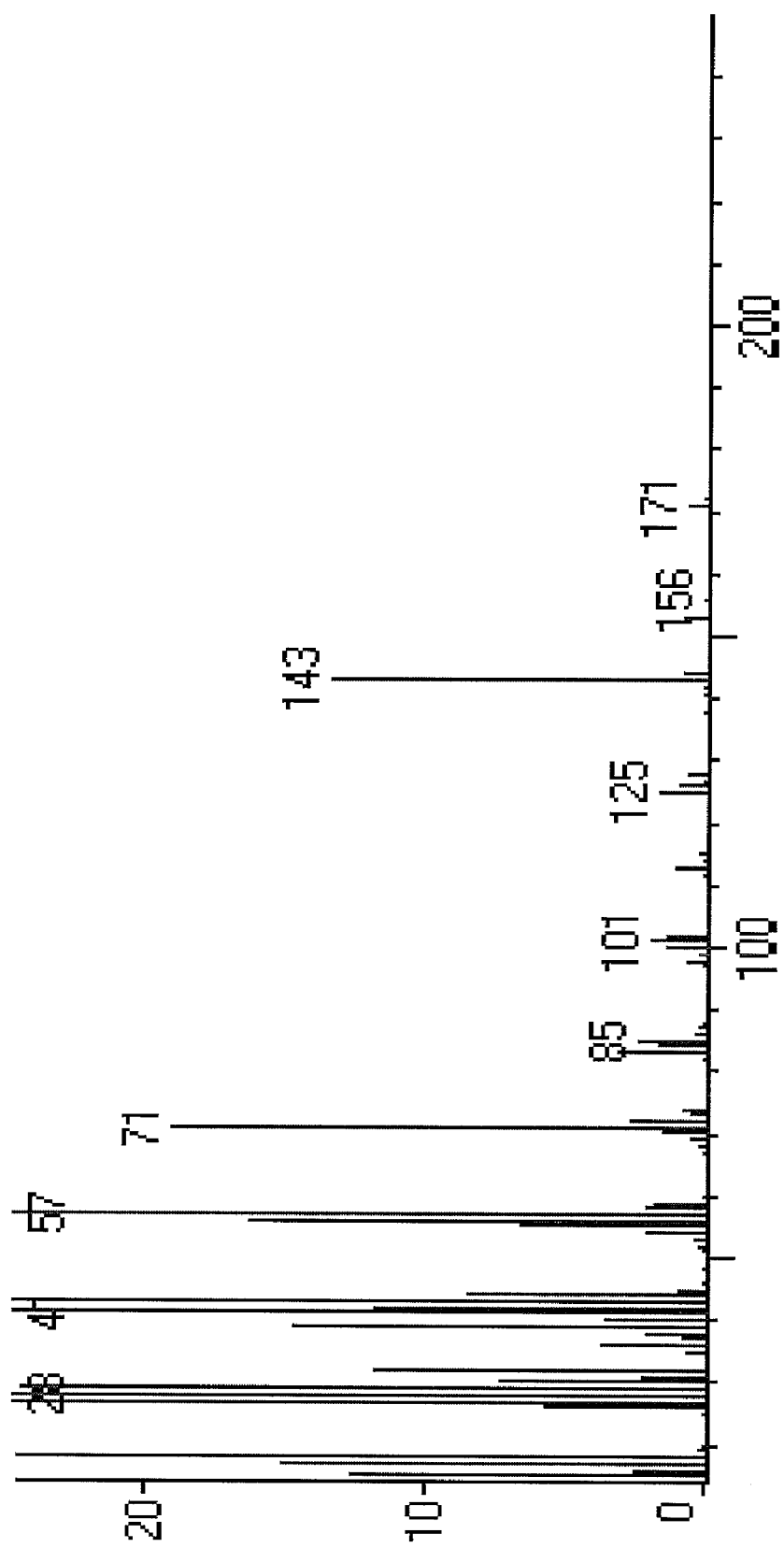

N-butanoyl-L-homoserine lactone (7a) was synthesized by the method described in Example 8. FIG. 2A shows the GC-MS spectrum assaying the purity of the synthesis (inset shows the chemical structure). FIG. 2B is the NMR spectrum where: $^1$H NMR (300 MHz, CDCl$_3$) δ=5.97 (s, 1H, NH), 4.59 (ddd, 1H, J=5.9 Hz, CH-lac), 4.51 (td, 1H, J=1.1 Hz, CH-lac), 4.34 (ddd, 1H, J=5.9 Hz, CH-lac), 2.93 (dddd, 1H, J=1.1 Hz, CH-lac), 2.27 (t, 2H, J=7.5 Hz, CH$_2$), 2.17 (ddd, 1H, J=1.7 Hz, CH-lac), 1.29 (h, 2H, J=7.4 Hz, CH$_2$), 0.99 (t, 3H, J=7.1 Hz, CH$_3$); $^{13}$C NMR (75 MHz, CDCl$_3$) δ=175.7, 174.2, 66.3, 49.5, 38.2, 29.9, 19.1, 13.9; GC-MS: expected m/z=171, observed [M+]=171;

[α$_D$]=+14.8 (c=3.4 mg/mL; CHCl$_3$); IR (cm$^{-1}$): 3020, 2401, 1781, 1515, 1425, 1216, 929, 757, 670.

Example 12

N-hexanoyl-L-homoserine lactone (7b)

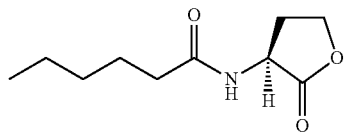

Figure 3A:
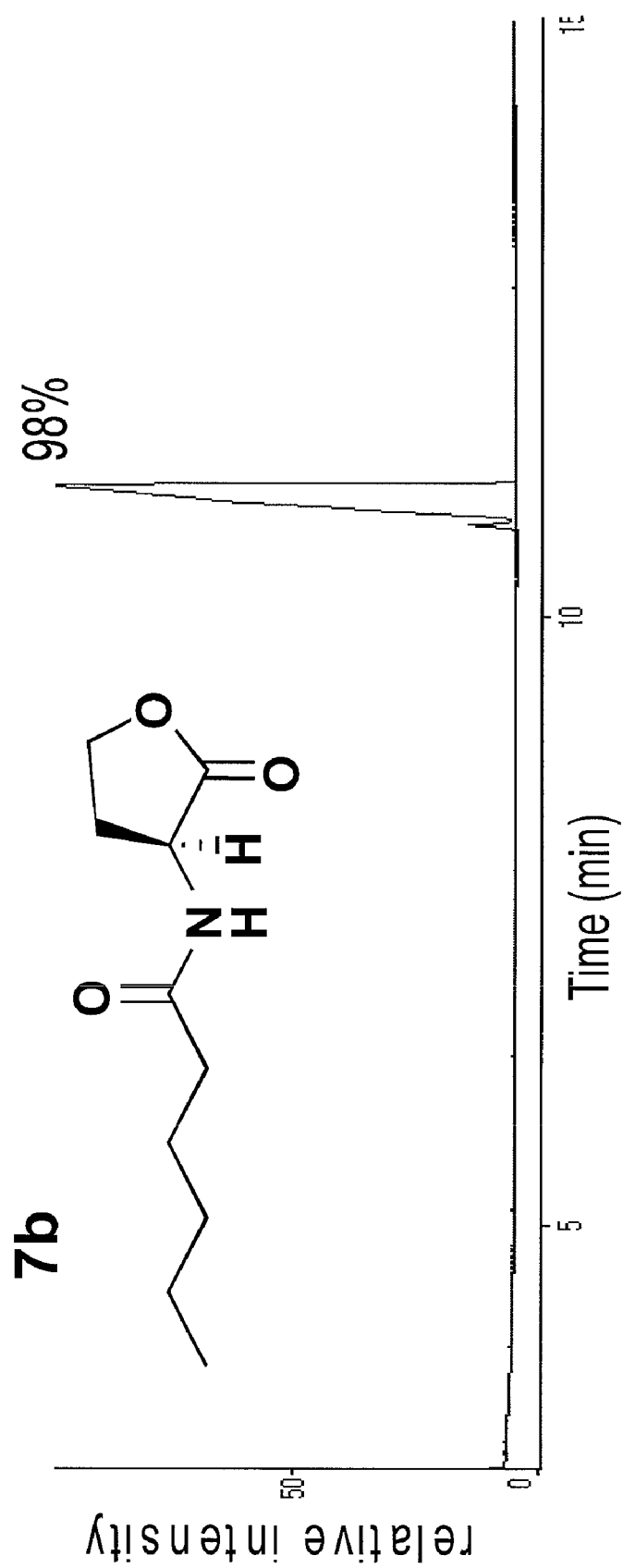
FIG. 3A shows a GC-MS spectrum and FIG. 3B shows an NMR spectrum for N-hexanoyl-L-homoserine lactone (7b) produced by the scheme shown in FIG. 1A.
Figure 3B:
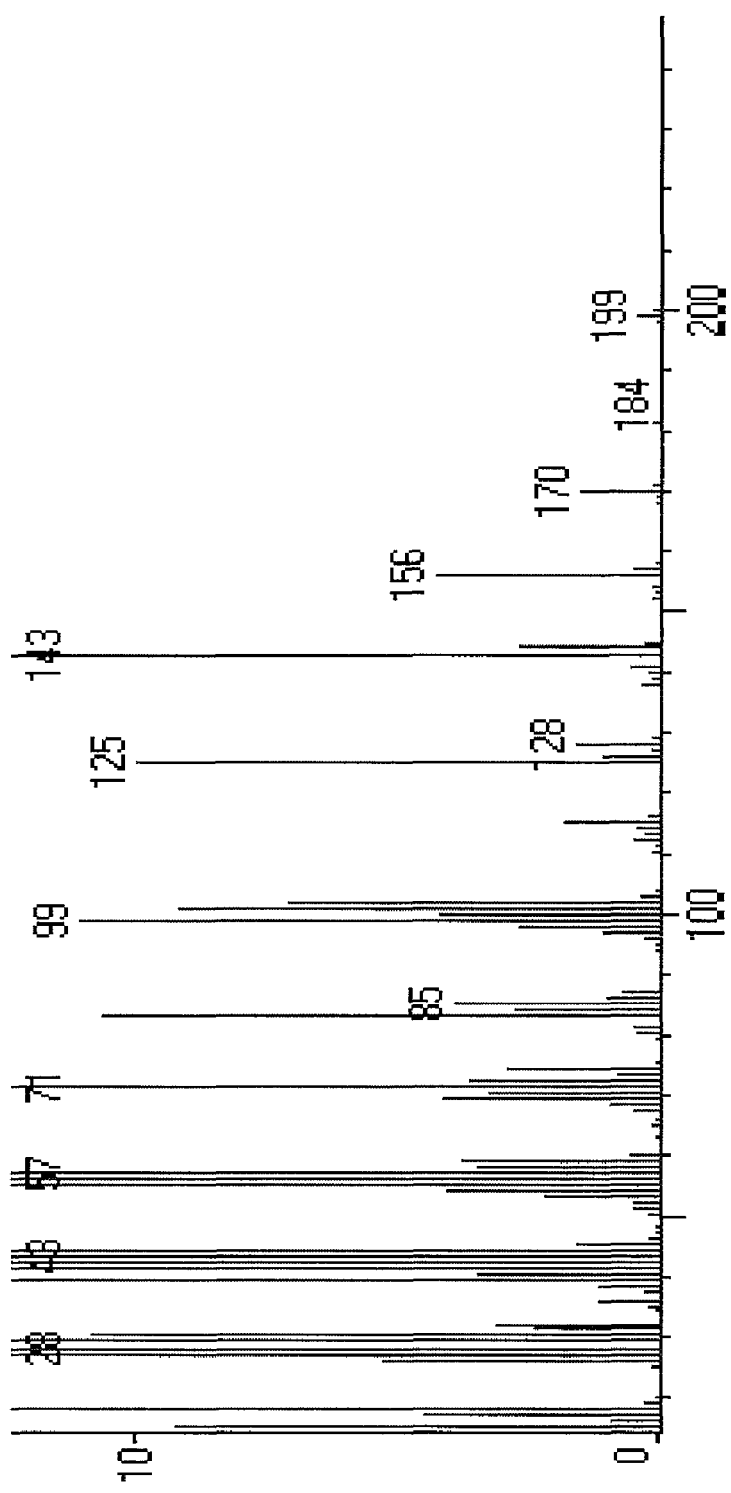

N-hexanoyl-L-homoserine lactone (7b) was synthesized by the method described in Example 7. FIG. 3A shows the GC-MS spectrum assaying purity (inset illustrates compound structure). FIG. 3B is the NMR spectrum where: $^1$H NMR (300 MHz, CDCl$_3$) δ=6.22 (s, 1H, NH), 4.63 (ddd, 1H, J=6.1 Hz, CH-lac), 4.51 (td, 1H, J=1.0 Hz, CH-lac), 4.34 (ddd, 1H, J=5.9 Hz, CH-lac), 2.89 (dddd, 1H, J=1.4 Hz, CH-lac), 2.28 (t, 2H, J=7.4 Hz, CH$_2$), 2.20 (ddd, 1H, J=2.2 Hz, CH-lac), 1.71 (t, 2H, J=7.4 Hz, CH$_2$), 1.34 (m, 4H, (CH$_2$)$_2$), 0.93 (t, 3H, J=7.1 Hz, CH$_3$); $^{13}$C NMR (75 MHz, CDCl$_3$) δ=175.9, 174.1, 66.4, 49.4, 36.4, 31.6, 30.8, 25.4, 22.6, 14.1; GC-MS: expected m/z=199, observed [M+]=199;

[α$_D$]=+15.9 (c=3.4 mg/mL; CHCl$_3$); IR (cm$^{-1}$): 3689, 3620, 3426, 3020, 2963, 2401, 1781, 1675, 1510, 1381, 1216, 1020, 929, 757, 669.

Example 13

N-octanoyl-L-homoserine lactone (7c)

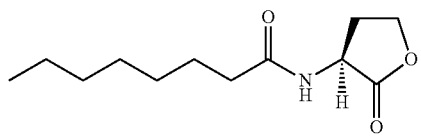

Figure 4A:
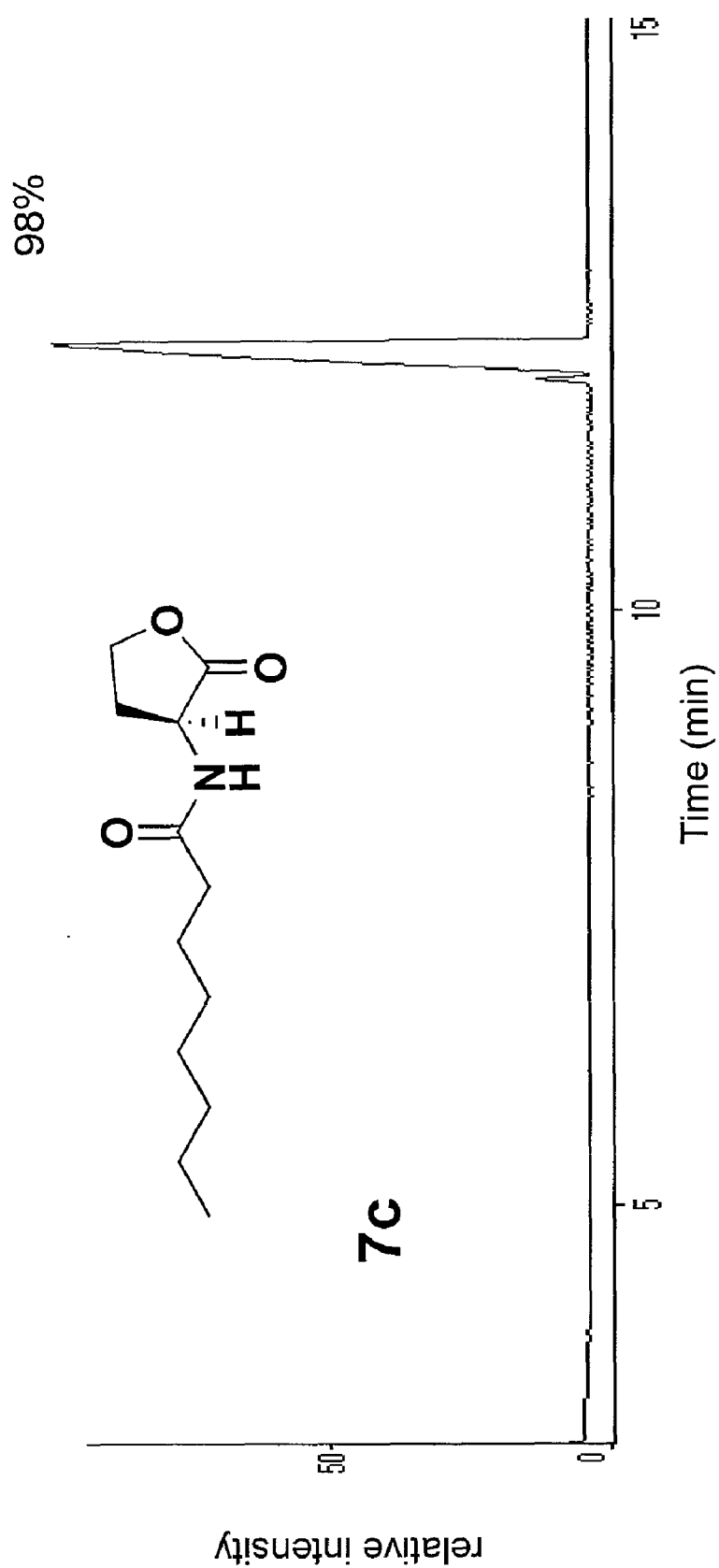
FIG. 4A shows a GC-MS spectrum and FIG. 4B shows an NMR spectrum for N-octanoyl-L-homoserine lactone (7c) produced by the scheme shown in FIG. 1A.
Figure 4B:
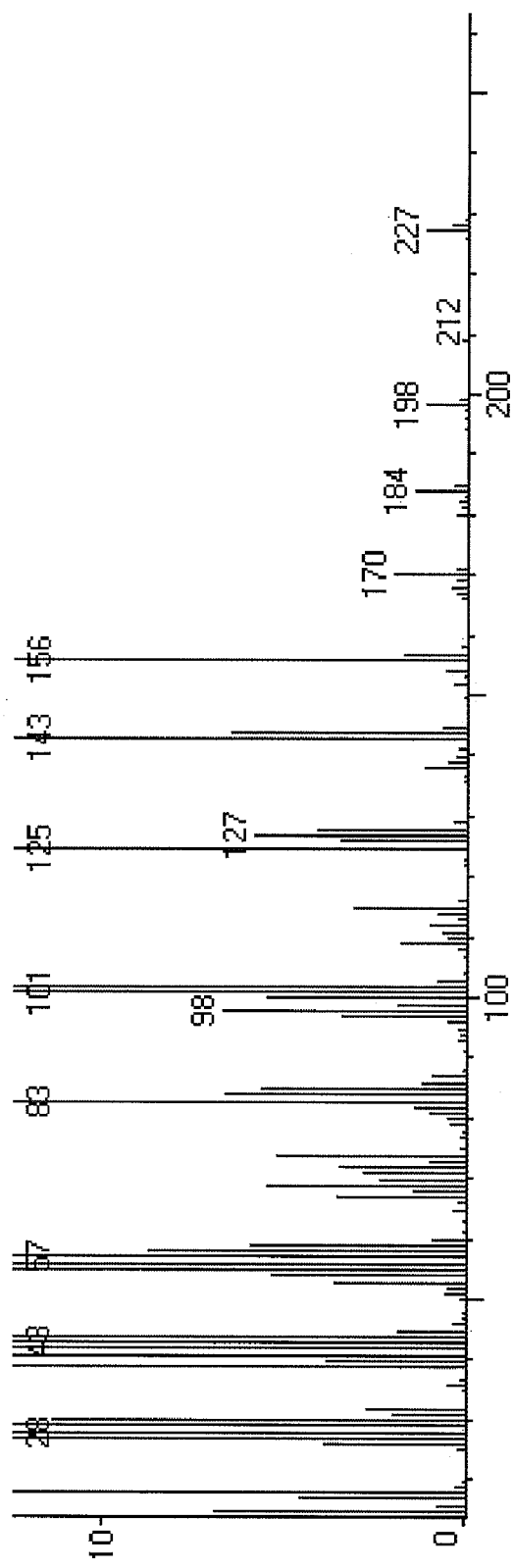

N-octanoyl-L-homoserine lactone (7c) was synthesized by the method described in Example 8. FIG. 4A shows the GC-MS spectrum assaying the purity of the synthesis (inset shows the chemical structure). FIG. 4B shows the NMR spectrum where: $^1$H NMR (300 MHz, CDCl$_3$) δ=6.44 (s, 1H, NH), 4.65 (ddd, 1H, J=6.5 Hz, CH-lac), 4.50 (t, 1H, J=9.2 Hz, CH-lac), 4.34 (ddd, 1H, J=2.3 Hz, CH-lac), 2.85 (dddd, 1H, J=6.1 Hz, CH-lac), 2.28 (t, 2H, J=7.4 Hz, CH$_2$), 2.22 (ddd, 1H, J=2.3 Hz, CH-lac), 1.67 (t, 2H, J=7.1 Hz, CH$_2$), 1.30 (m, 8H, (CH$_2$)$_4$), 0.91 (t, 3H, J=6.3 Hz, CH$_3$); $^{13}$C NMR (75 MHz, CDCl$_3$) δ=175.5, 173.7, 65.9, 48.9, 35.9, 31.4, 30.1, 29.0, 28.8, 25.2, 22.4, 13.8; GC-MS: expected m/z=227, observed [M+]=227; [α$_D$]=+15.9 (c=3.4 mg/mL; CHCl$_3$); IR (cm$^{-1}$): 3684, 3619, 3427, 3020, 2930, 2858, 2401, 1780, 1673, 1511, 1423, 1381, 1216, 1019, 929, 772, 669.

Example 14

N-decanoyl-L-homoserine lactone (7d)

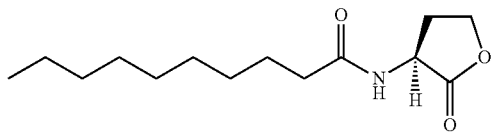

Figure 5A:
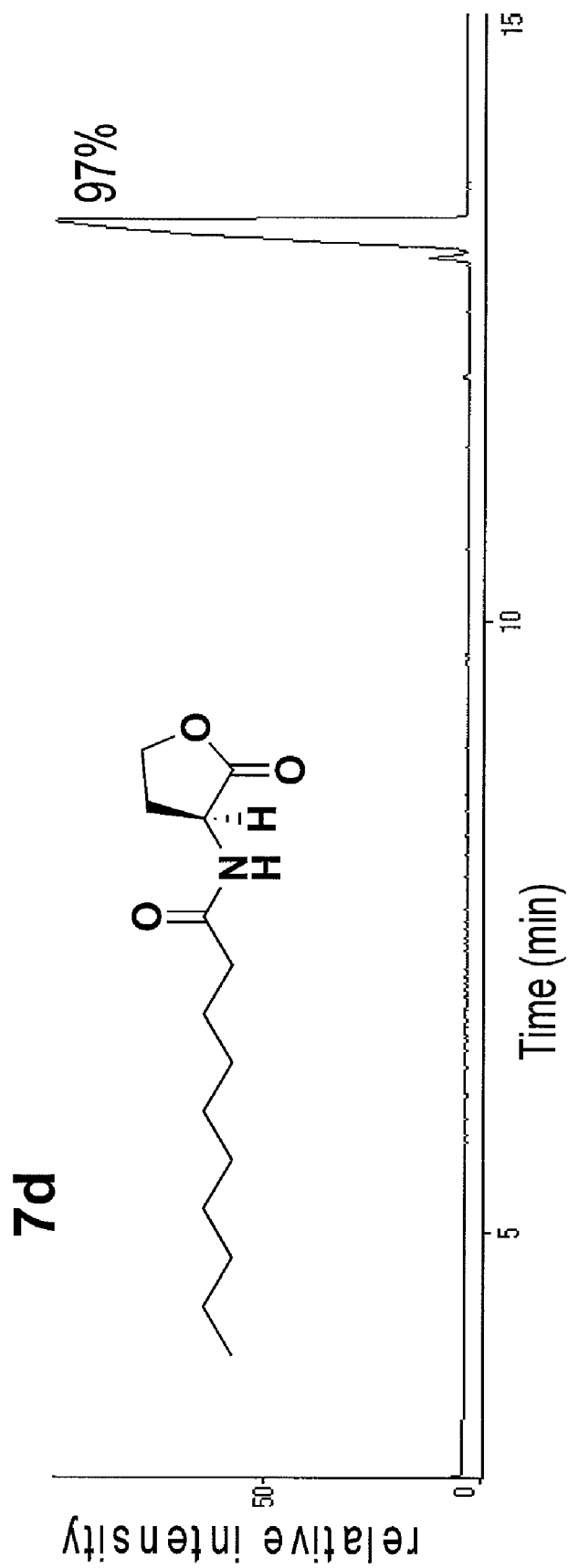
FIG. 5A shows a GC-MS spectrum and FIG. 5B shows an NMR spectrum for N-decanoyl-L-homoserine lactone (7d) produced by the scheme shown in FIG. 1A.
Figure 5B:
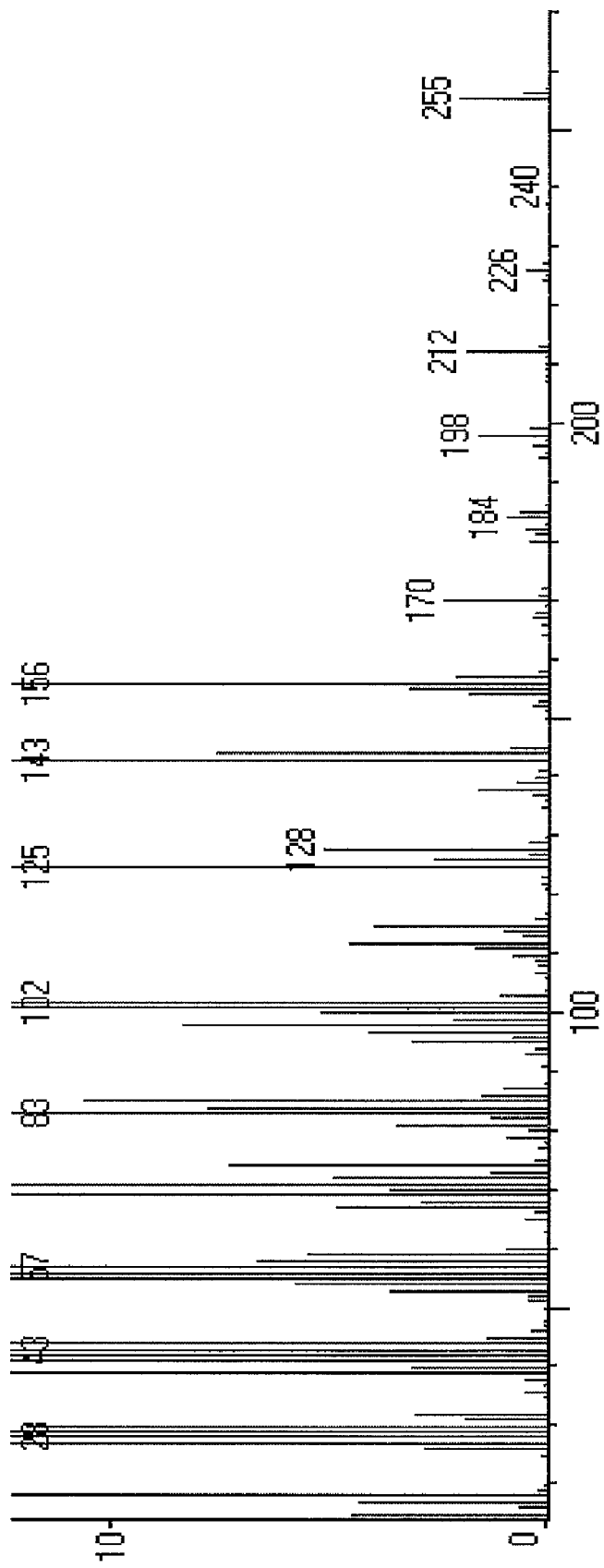

N-decanoyl-L-homoserine lactone (7d) was synthesized by the method described in Example 8. FIG. 5A is the GC-MS spectrum assaying the purity of the synthesis (inset shows the chemical structure). FIG. 5B is an NMR spectrum where: $^1$H NMR (300 MHz, CDCl$_3$) δ=6.16 (s, 1H, NH), 4.62 (ddd, 1H, J=6.0 Hz, CH-lac), 4.51 (td, 1H, J=1.0 Hz, CH-lac), 4.34 (ddd, 1H, J=5.9 Hz, CH-lac), 2.90 (dddd, 1H, J=8.3 Hz, CH-lac), 2.28 (t, 2H, J=6.9 Hz, CH$_2$), 2.15 (ddd, 1H, J=3.3 Hz, CH-lac), 1.70 (t, 2H, J=7.5 Hz, CH$_2$), 1.30 (m, 12H, (CH$_2$)$_6$), 0.91 (t, 3H, J=6.6 Hz, CH$_3$); $^{13}$C NMR (75 MHz, CDCl$_3$) δ=175.7, 173.9, 66.2, 49.3, 36.3, 31.9, 30.7, 29.5, 29.4, 29.3, 25.5, 22.7, 14.2; GC-MS: expected m/z=255, observed [M+]=255; [α$_D$]=+15.5 (c=2.9 mg/mL; CHCl$_3$); IR (cm$^{-1}$): 3684, 3620, 3427, 3020, 2928, 2857, 2401, 1780, 1673, 1511, 1423, 1381, 1216, 1019, 929, 772, 669.

Example 15

N-dodecanoyl-L-homoserine lactone (7e)

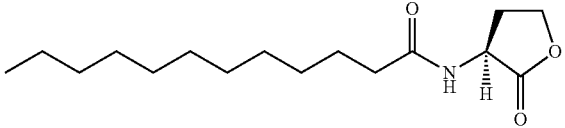

Figure 6A:
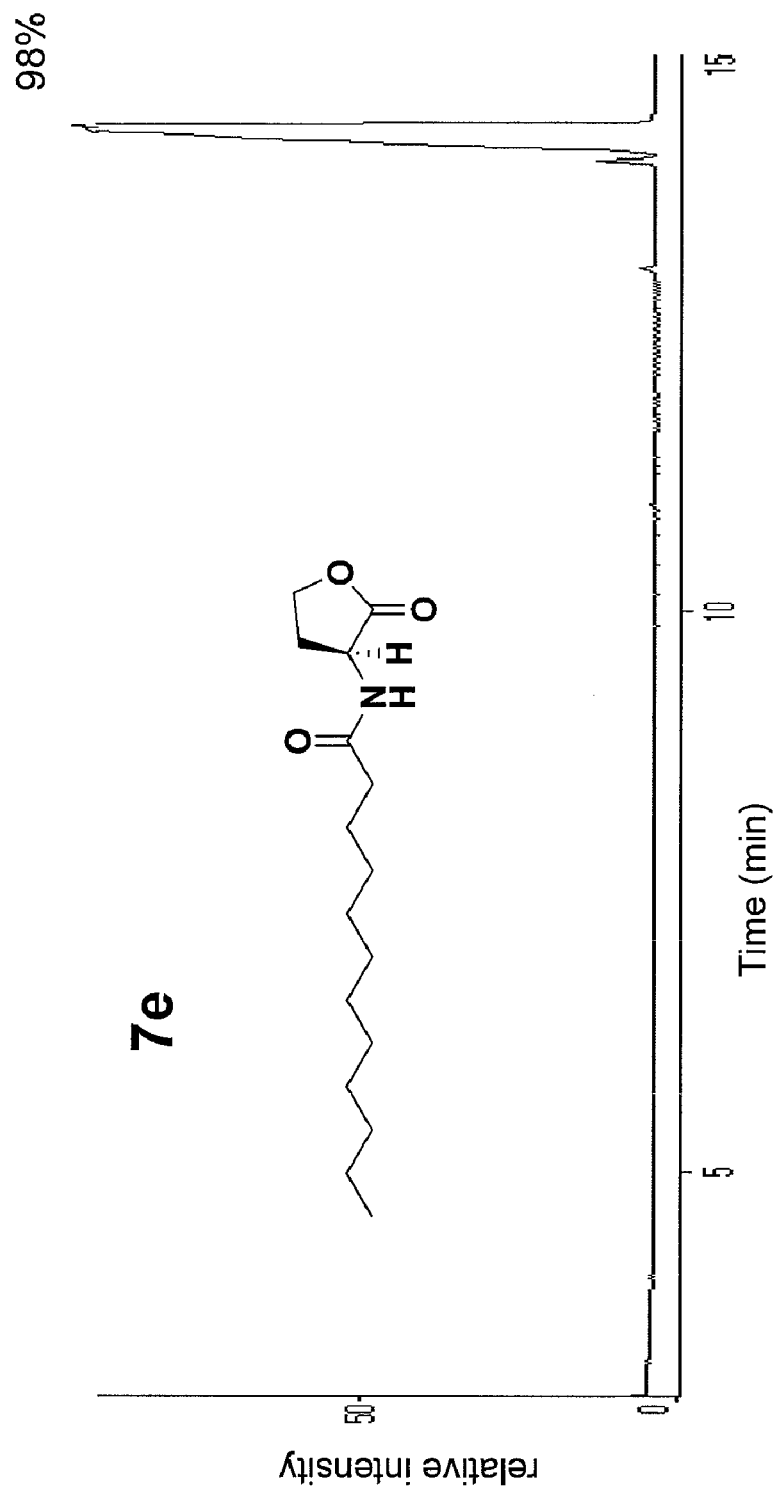
FIG. 6A shows a GC-MS spectrum and FIG. 6B shows an NMR spectrum for N-dodecanoyl-L-homoserine lactone (7e) produced by the scheme shown in FIG. 1A.
Figure 6B:
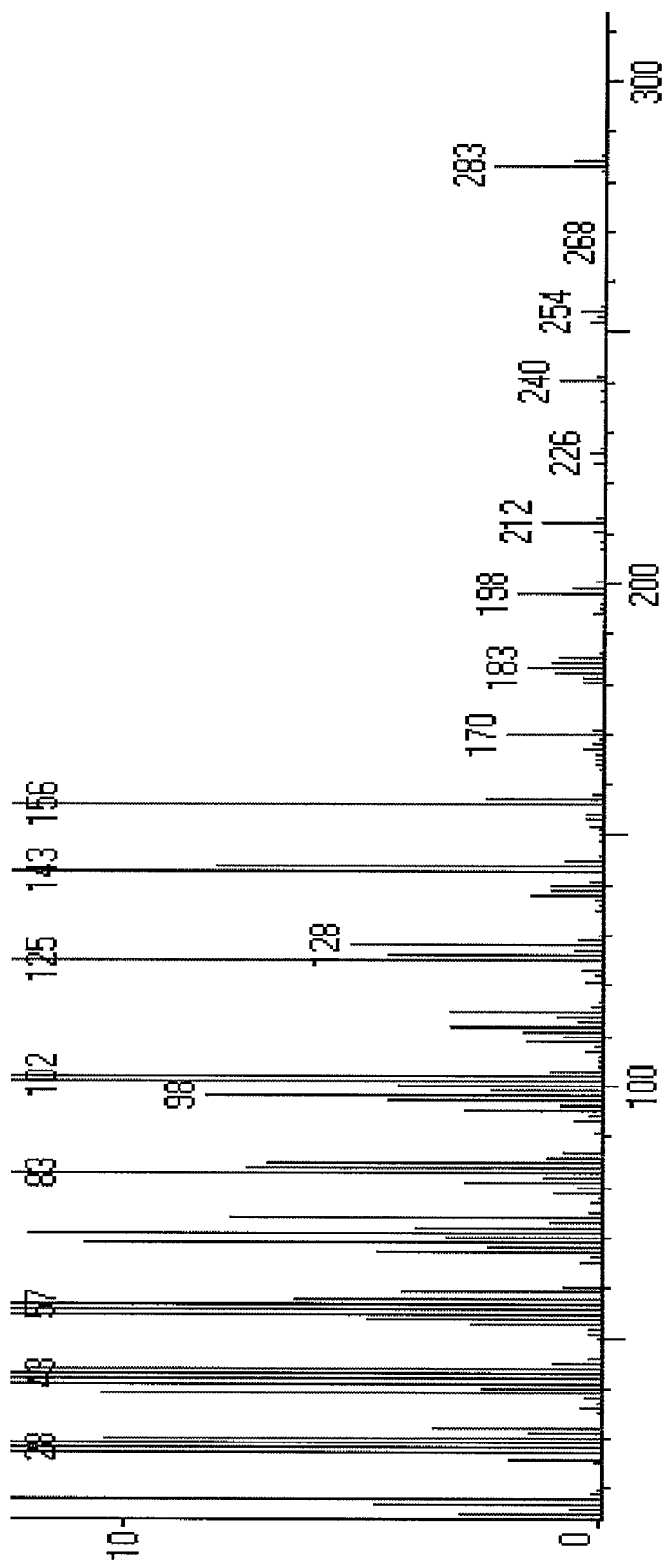

N-dodecanoyl-L-homoserine lactone (7e) was synthesized by the method described in Example 8. FIG. 6A is the GC-MS spectrum assaying the purity of the synthesis (inset shows the chemical structure) while 6B is the NMR spectrum where: $^1$H NMR (300 MHz, CDCl$_3$) δ=6.22 (s, 1H, NH), 4.63 (ddd, 1H, J=6.1 Hz, CH-lac), 4.50 (t, 1H, J=9.1 Hz, CH-lac), 4.34 (ddd, 1H, J=5.9 Hz, CH-lac), 2.86 (dddd, 1H, J=5.9 Hz, CH-lac), 2.28 (t, 2H, J=6.9 Hz, CH$_2$), 2.19 (ddd, 1H, J=2.9 Hz, CH-lac), 1.67 (t, 2H, J=6.8 Hz, CH$_2$), 1.30 (m, 18H, (CH$_2$)$_9$), 0.91 (t, 3H, J=6.5 Hz, CH$_3$); $^{13}$C NMR (75 MHz, CDCl$_3$) δ=176.1, 174.3, 66.6, 49.7, 36.7, 32.4, 31.0, 30.1, 29.9, 29.7, 29.6, 25.9, 23.2, 14.6; GC-MS: expected m/z=283, observed [M+]=283; [α$_D$]=+15.1 (c=3.5 mg/mL; CHCl$_3$); IR (cm$^{-1}$): 3684, 3621, 3426, 3020, 2928, 2856, 2401, 1780, 1673, 1511, 1381, 1216, 1019, 929, 760, 669.

Example 16

N-hexadecanoyl-L-homoserine lactone (7f)

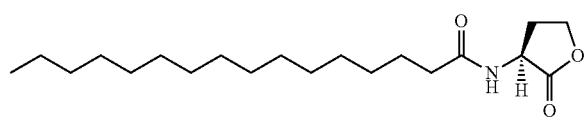

Figure 7A:
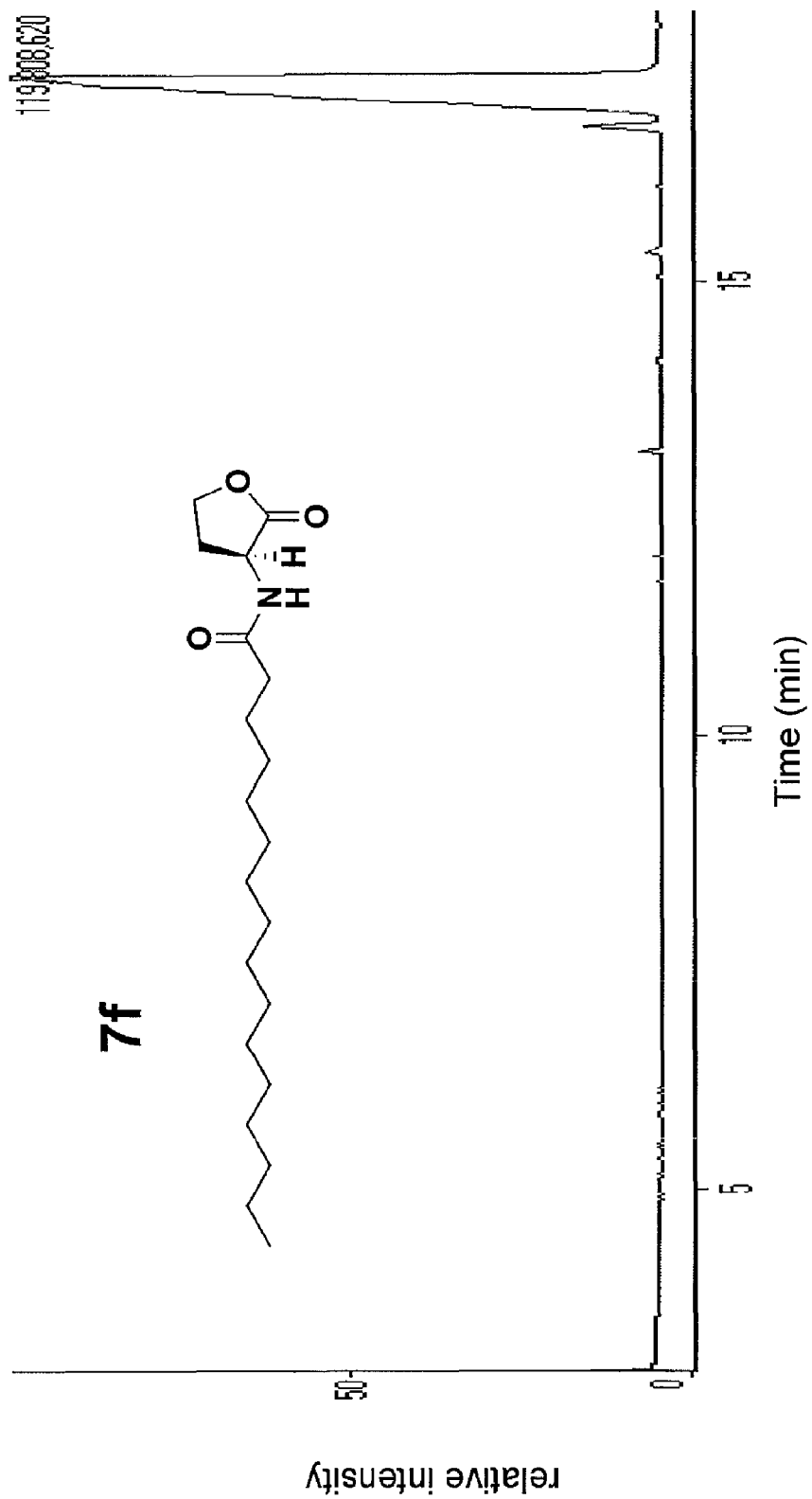
FIG. 7A shows a GC-MS spectrum and FIG. 7B shows an NMR spectrum for N-hexadecanoyl-L-homoserine lactone (7f) produced by the scheme shown in FIG. 1A.
Figure 7B:
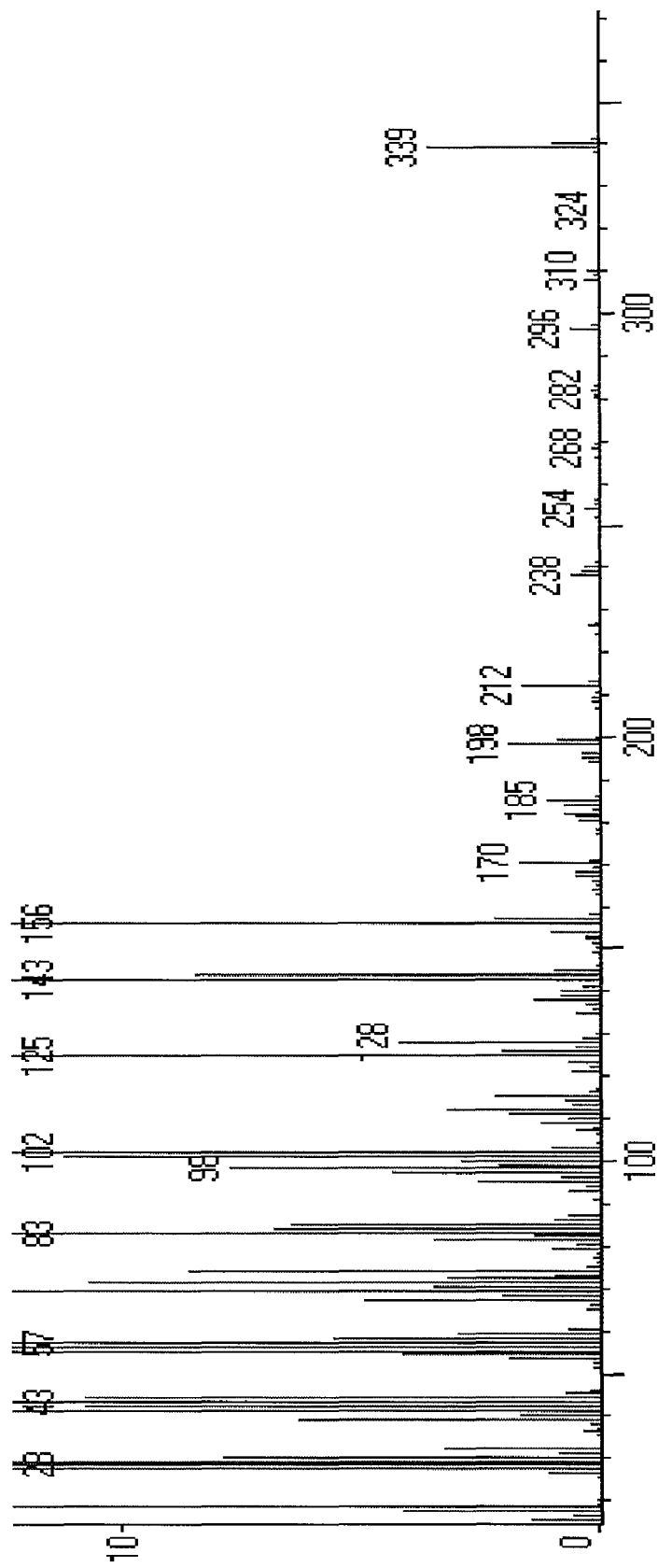

N-hexadecanoyl-L-homoserine lactone (7f) was synthesized by the method described in Example 8. FIG. 7A is the GC-MS spectrum assaying the purity of the synthesis (inset shows the chemical structure). FIG. 7B is the NMR spectrum where: $^1$H NMR (300 MHz, CDCl$_3$) δ=6.03 (s, 1H, NH), 4.59 (ddd, 1H, J=5.6 Hz, CH-lac), 4.50 (t, 1H, J=8.2 Hz, CH-lac), 4.33 (ddd, 1H, J=5.7 Hz, CH-lac), 2.92 (dddd, 1H, J=1.3 Hz, CH-lac), 2.28 (t, 2H, J=6.9 Hz, CH$_2$), 2.20 (ddd, 1H, J=8.8 Hz, CH-lac), 1.69 (t, 2H, J=7.1 Hz, CH$_2$), 1.31 (m, 24H, (CH$_2$)$_{12}$), 0.91 (t, 3H, J=6.4 Hz, CH$_3$); $^{13}$C NMR (75 MHz, CDCl$_3$) δ=175.8, 174.0, 66.4, 49.6, 36.5, 32.2, 31.0, 30.0, 29.7, 29.6, 29.5, 25.7, 23.0, 14.4; GC-MS: expected m/z=339, observed [M+]=339; [α$_D$]=+14.9 (c=2.4 mg/mL; CHCl$_3$); IR (cm$^{-1}$): 3684, 3621, 3426, 3020, 2928, 2855, 2401, 1781, 1675, 1513, 1424, 1381, 1216.

Example 17

N-heptanoyl-L-homoserine lactone (7g)

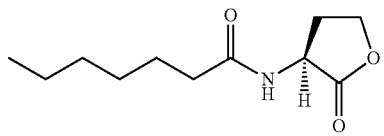

Figure 8A:
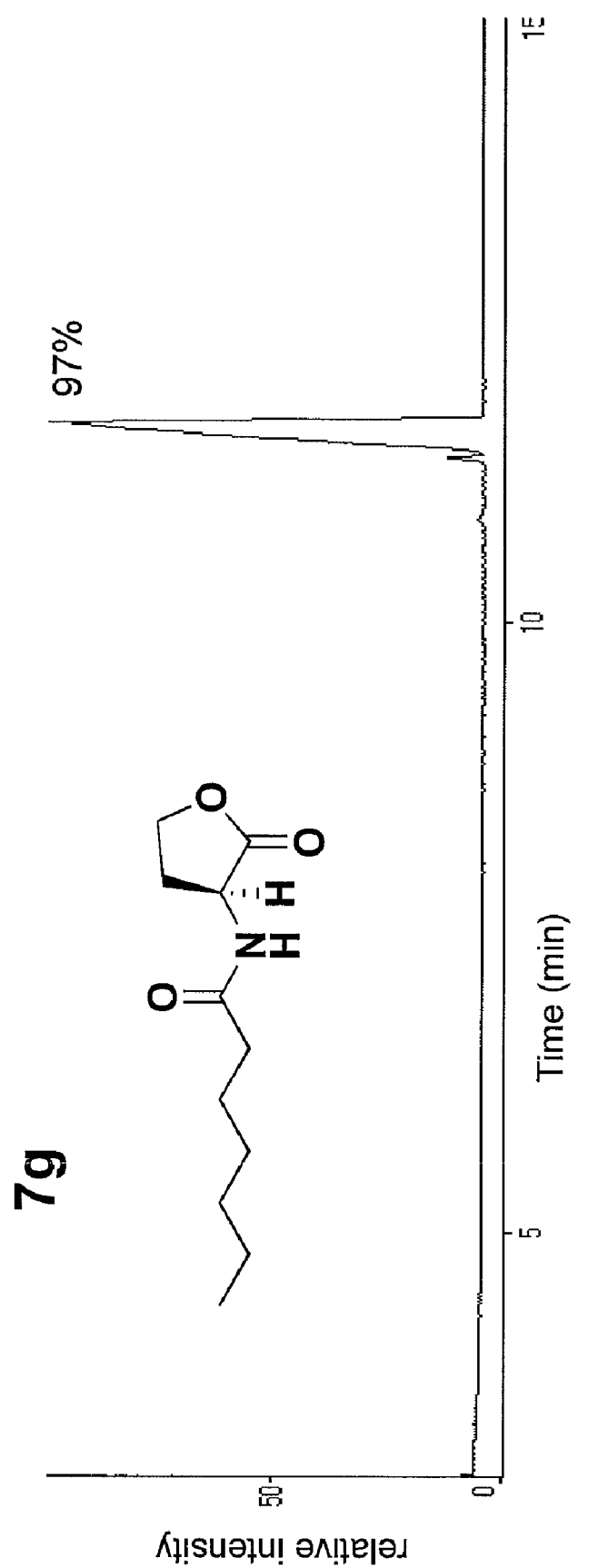
FIG. 8A shows a GC-MS spectrum and FIG. 8B shows an NMR spectrum for N-heptanoyl-L-homoserine lactone (7g) produced by the scheme shown in FIG. 1A.
Figure 8B:
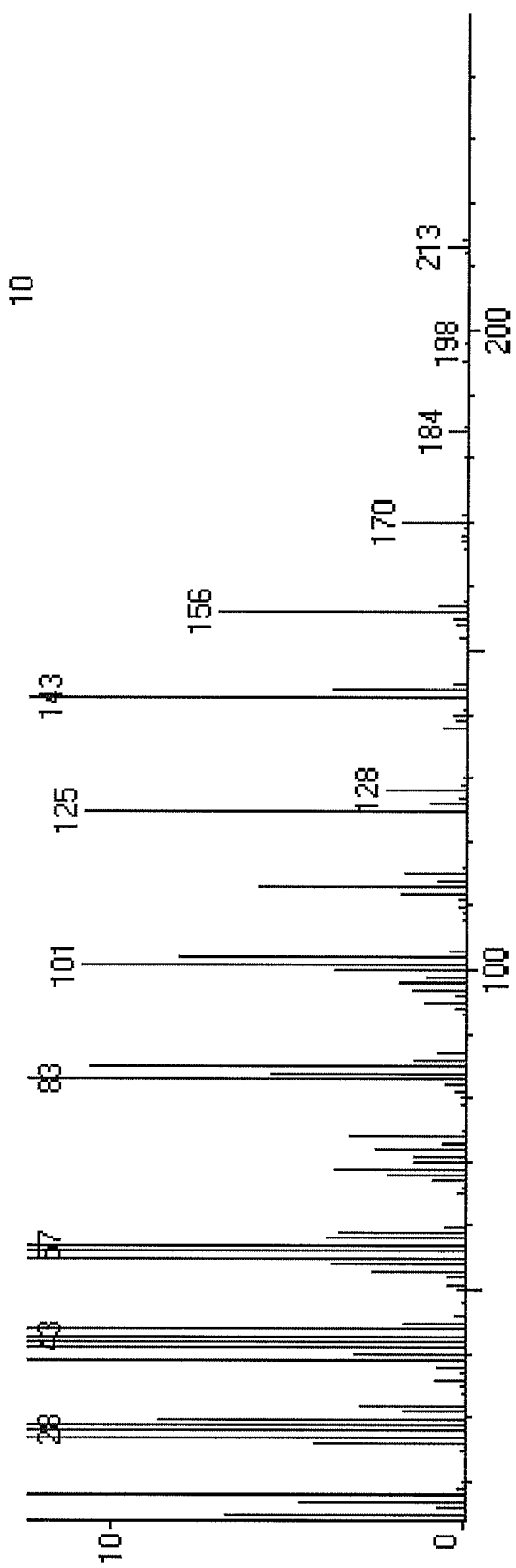

N-heptanoyl-L-homoserine lactone (7g) was synthesized by the method described in Example 8. FIG. 8A is the GC-MS spectrum assaying the purity of the synthesis (inset shows the chemical structure). FIG. 8B is the NMR spectrum where: $^1$H NMR (300 MHz, CDCl$_3$) δ=6.28 (s, 1H, NH), 4.64 (ddd, 1H, J=6.4 Hz, CH-lac), 4.50 (td, 1H, J=1.2 Hz, CH-lac), 4.34 (ddd, 1H, J=5.8 Hz, CH-lac), 2.87 (dddd, 1H, J=8.4 Hz, CH-lac), 2.28 (t, 2H, J=6.7 Hz, CH$_2$), 2.20 (ddd, 1H, J=2.5 Hz, CH-lac), 1.70 (t, 2H, J=7.8 Hz, CH$_2$), 1.38 (m, 6H, (CH$_2$)$_3$), 0.91 (t, 3H, J=6.7 Hz, CH$_3$); $^{13}$C NMR (75 MHz, CDCl$_3$) δ=175.5, 173.6, 65.9, 49.0, 36.0, 31.3, 30.3, 28.7, 25.2, 22.3, 13.8; GC-MS: expected m/z=213, observed [M+]=213; [α$_D$]=+12.6 (c=1.9 mg/mL; CHCl$_3$); IR (cm$^{-1}$): 3685, 3621, 3427, 3020, 2931, 2401, 1780, 1674, 1510, 1423, 1381, 1216.

Example 18

N-(indole-3-butanoyl)-L-homoserine lactone (7h)

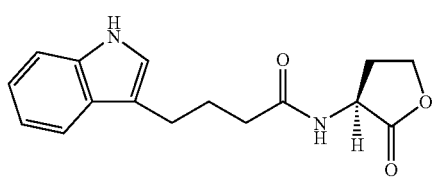

Figure 9A:
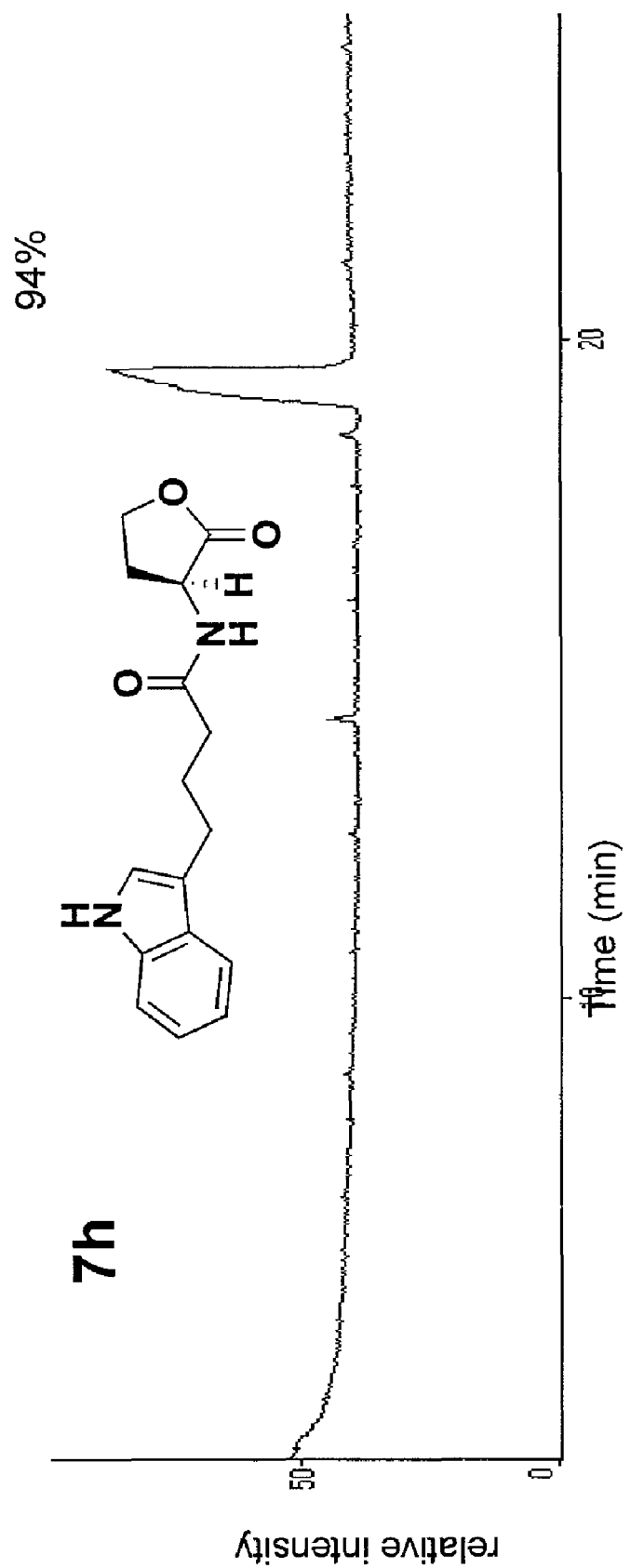
FIG. 9A shows a GC-MS spectrum and FIG. 9B shows an NMR spectrum for N-(indole-3-butanoyl)-L-homoserine lactone (7h) produced by the scheme shown in FIG. 1A.
Figure 9B:
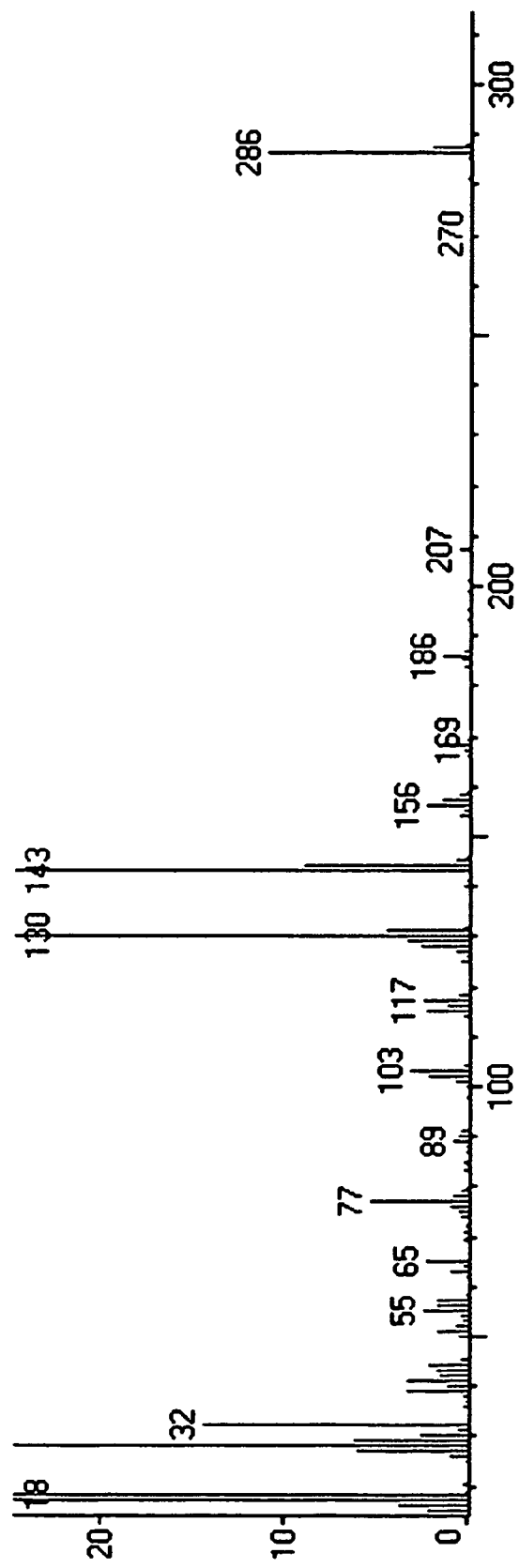

N-(indole-3-butanoyl)-L-homoserine lactone (7h) was synthesized by the methods described in Example 8. FIG. 9A is the GC-MS spectrum assaying the purity of the synthesis (inset shows the chemical structure). FIG. 9B is the NMR spectrum where $^1$H NMR (300 MHz, CDCl$_3$) δ=8.08 (s, 1H, NH-indole), 7.59 (d, 1H, J=7.6 Hz, CH—Ar), 7.35 (d, 1H, J=7.1 Hz, CH—Ar), 7.20 (td, 1H, J=1.2 Hz, CH—Ar), 7.12 (td, 1H, J=1.2 Hz, CH—Ar), 6.97 (d, 1H J=2.3 Hz, CH—Ar), 6.05 (d, 1H, J=5.8 Hz, NH), 4.54 (ddd, 1H, J=6.3 Hz, CH-lac), 4.43 (td, 1H, J=0.9 Hz, CH-lac), 4.26 (ddd, 1H, J=6.0 Hz, CH-lac), 2.82 (t, 2H, J=7.3 Hz, CH$_2$), 2.76 (m, 1H, CH-lac), 2.28 (t, 2H, J=7.7 Hz, CH$_2$), 2.10 (m, 3H, CH$_2$+CH-lac); $^{13}$C NMR (75 MHz, CDCl$_3$) δ=122.2, 121.9, 119.5, 119.1, 115.6, 111.3, 66.2, 49.4, 35.7, 30.7, 25.8, 24.6; GC-MS: expected m/z=286, observed [M+]=286; [α$_D$]=+14.2 (c=2.6 mg/mL; CHCl$_3$); IR (cm$^{-1}$): 3684, 3620, 3480, 3426, 3020, 2977, 2401, 2362, 2254, 1780, 1674, 1603, 1514, 1217.

Example 19

N-(indole-3-butanoyl)-D-homoserine lactone (7i)

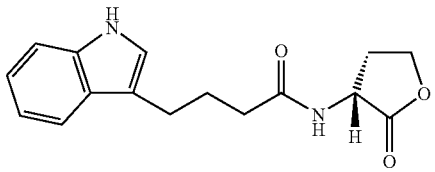

Figure 10A:
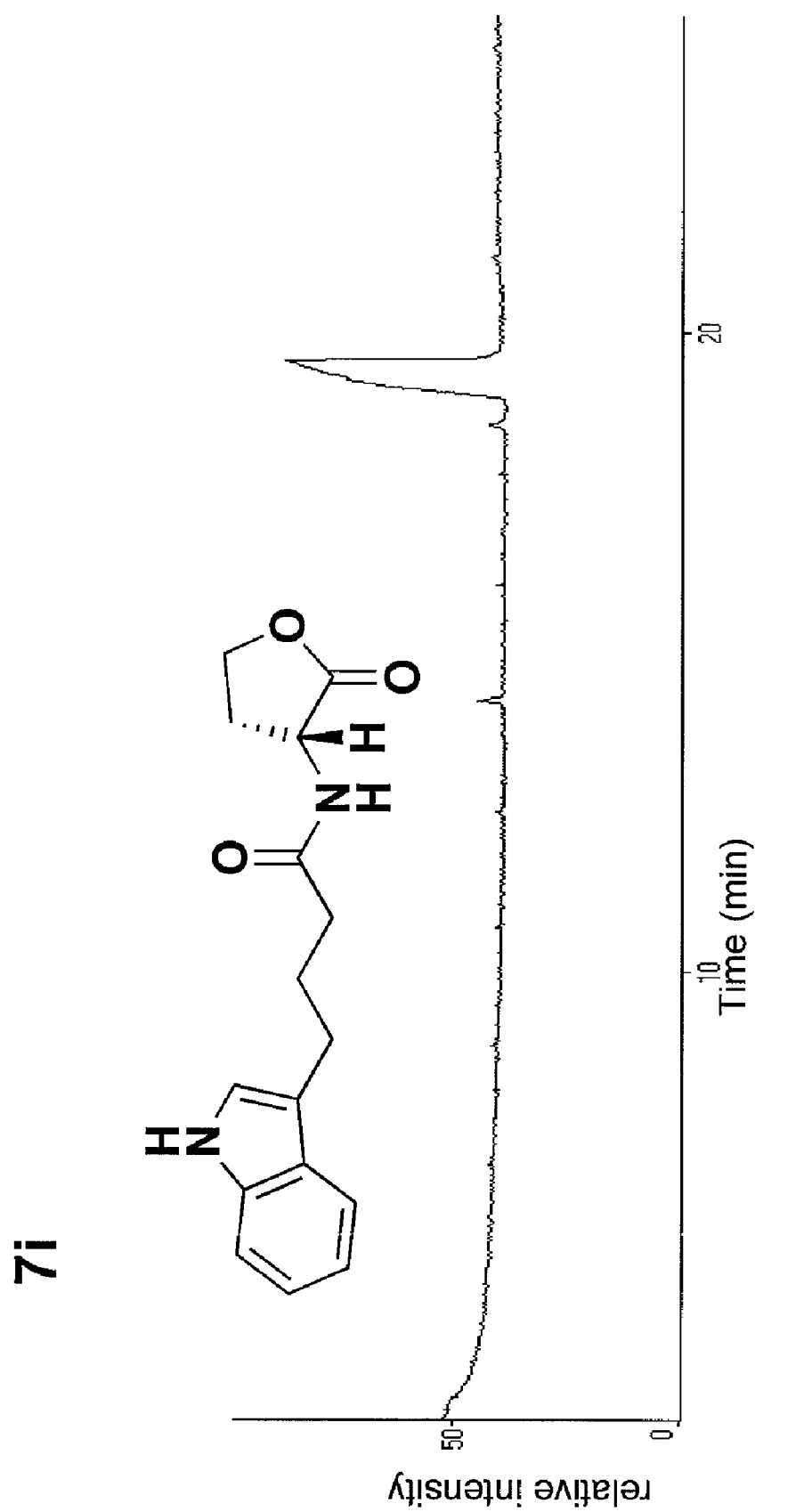
FIG. 10A shows a GC-MS spectrum and FIG. 10B shows an NMR spectrum for N-(indole-3-butanoyl)-D-homoserine lactone (7i) produced by the scheme shown in FIG. 1A.
Figure 10B:
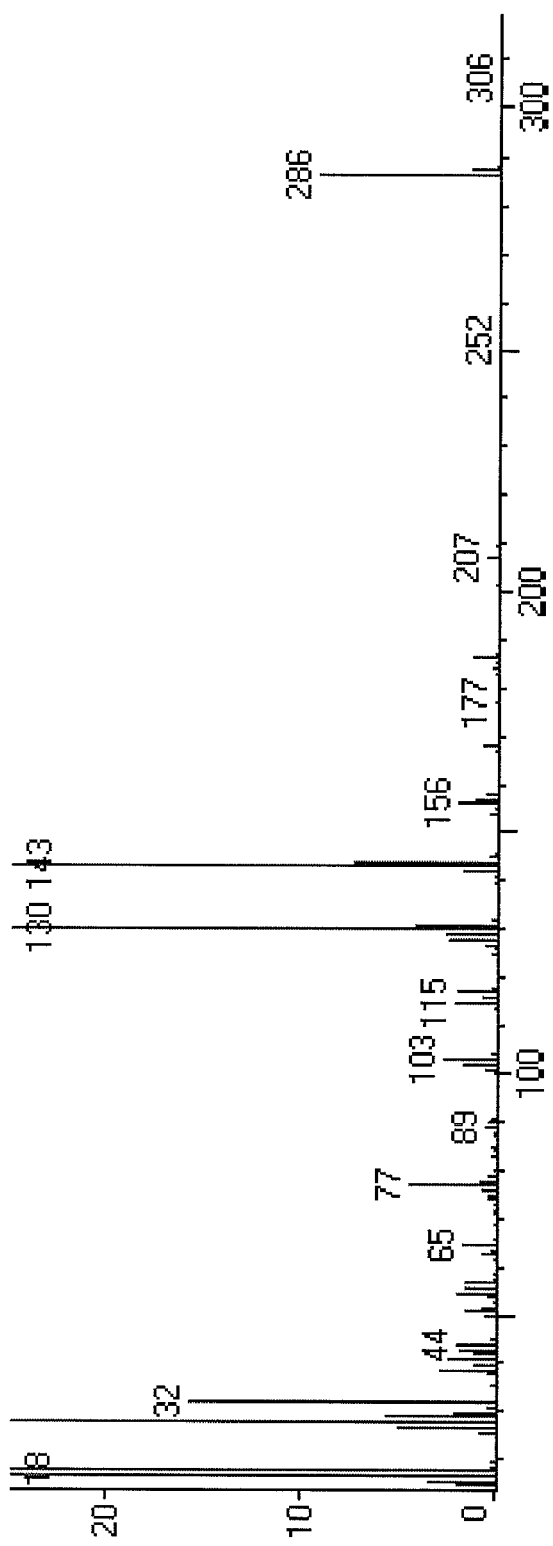

N-(indole-3-butanoyl)-D-homoserine lactone (7i) was synthesized by the method described in Example. 8. FIG. 10A is the GC-MS spectrum assaying the purity of the synthesis (inset shows the chemical structure). FIG. 10B is the NMR spectrum where: $^1$H NMR (300 MHz, CDCl$_3$) δ=7.99 (s, 1H, NH), 7.61 (d, 1H, J=0.6 Hz, CH—Ar), 7.37 (d, 1H, J=0.4 Hz, CH—Ar), 7.26 (m, 2H, CH—Ar), 7.01 (d, 1H, J=2.1 Hz, CH—Ar), 5.90 (d, 1H, J=4.4 Hz, NH), 4.55 (ddd, 1H, J=5.9 Hz, CH-lac), 4.46 (td, 1H, J=8.3 Hz, CH-lac) 4.29 (ddd, 1H, J=5.9 Hz, CH-lac), 2.85 (m, 3H), 2.32 (m, 2H), 2.17 (m, 3H); $^{13}$C NMR (75 MHz, CDCl$_3$) δ=122.2, 121.8, 119.5, 111.3, 66.3, 49.4, 35.7, 30.7, 25.8, 24.6; GC-MS: expected m/z=286, observed [M+]=286; [α$_D$]=−11.6 (c=1.95 mg/mL; CHCl$_3$); IR (cm$^{-1}$): 3359, 2921, 2692, 2358, 1771, 1648, 1558, 1220, 1019.

Example 20

N-Boc-(4-aminomethyl)-N-benzoyl-L-homoserine lactone (7j)

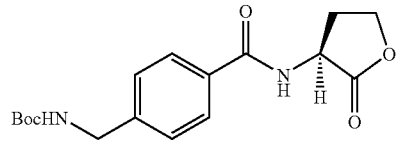

Figure 11:
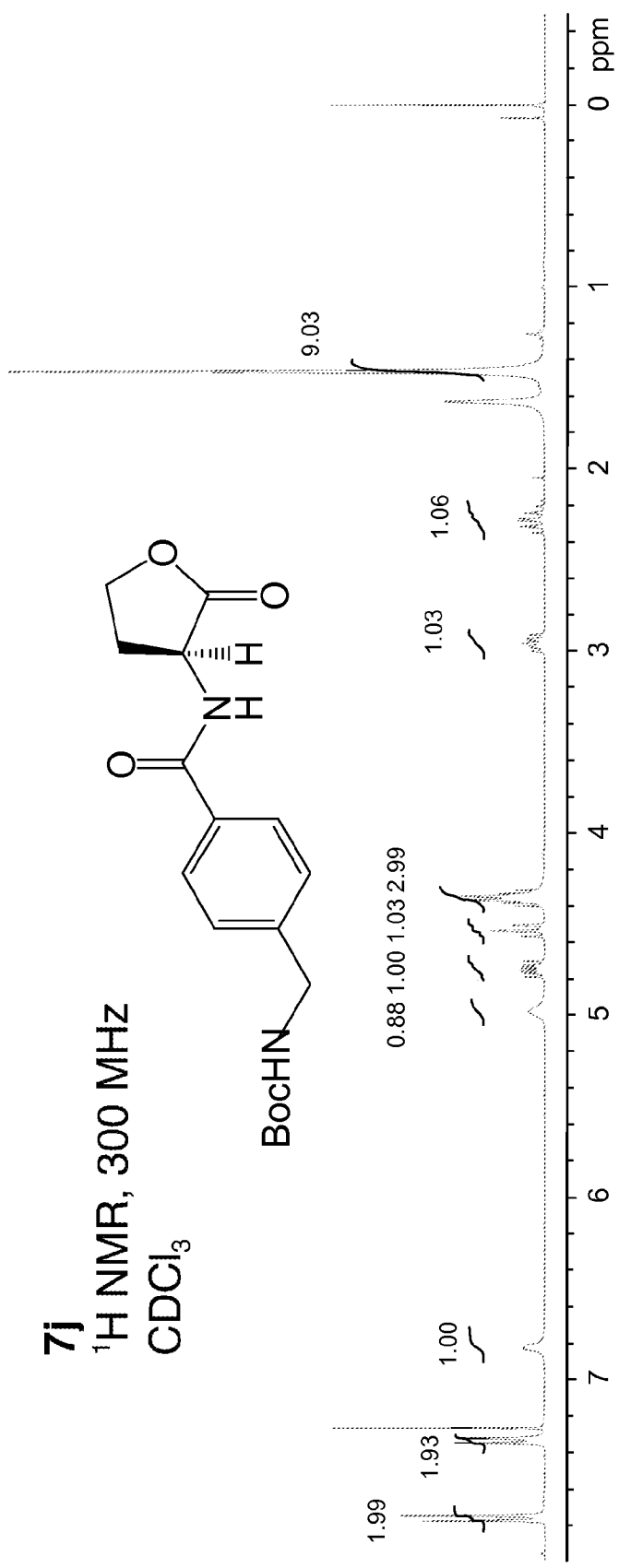
FIG. 11 shows an NMR spectrum for N-Boc-(4-aminomethyl)-N-benzoyl-L-homoserine lactone (7j) produced by the scheme shown in FIG. 1A.

N-Boc-(4-aminomethyl)-N-benzoyl-L-homoserine lactone (7j) was synthesized by the method described in Example 8. FIG. 11 is the NMR spectrum where: $^1$H NMR (300 MHz, CDCl$_3$) δ=7.78 (d, 2H, Ar—H), 7.35 (d, 2H, Ar—H), 6.02 (d, 1H, NH), 4.98 (s, 1H, NH), 4.79 (ddd, 1H, J=6.0 Hz, CH-lac), 4.57 (td, 1H, J=0.9 Hz, CH-lac), 4.40 (m, 3H, J=8.7 Hz, CH$_2$+CH-lac) 3.00 (dddd, 1H, J=1.2 Hz, CH-lac), 2.35 (ddd, 1H, J=8.8 Hz, CH-lac), 1.47 (s, 9H, BocCH₃); ¹³C NMR (75 MHz, CDCl₃) δ=131.7, 127.3, 66.1, 49.6, 30.4, 28.2; MS(ESI): expected m/z=334, observed [M+Na]=357; [α$_D$]=+21.6 (c=2.7 mg/mL; CHCl₃); IR (cm⁻¹): 3621, 3453, 3020, 2401, 1780, 1692, 1527, 1216.

Example 21

N-(2-cyclopentene-1-acetanoyl)-L-homoserine lactone (7k)

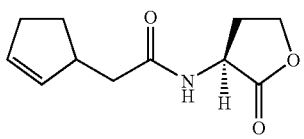

Figure 12A:
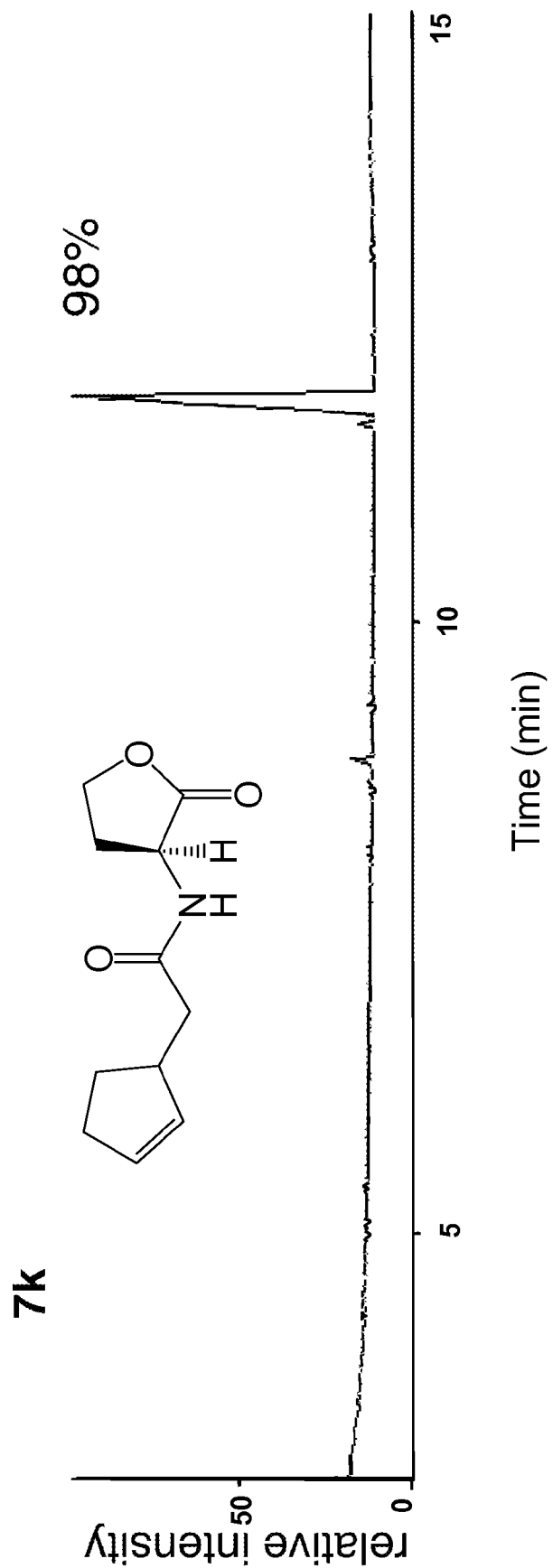
FIG. 12A shows a GC-MS spectrum and FIG. 12B shows an NMR spectrum for N-(2-cyclopentene-1-acetanoyl)-L-homoserine lactone (7k) produced by the scheme shown in FIG. 1A.
Figure 12B:
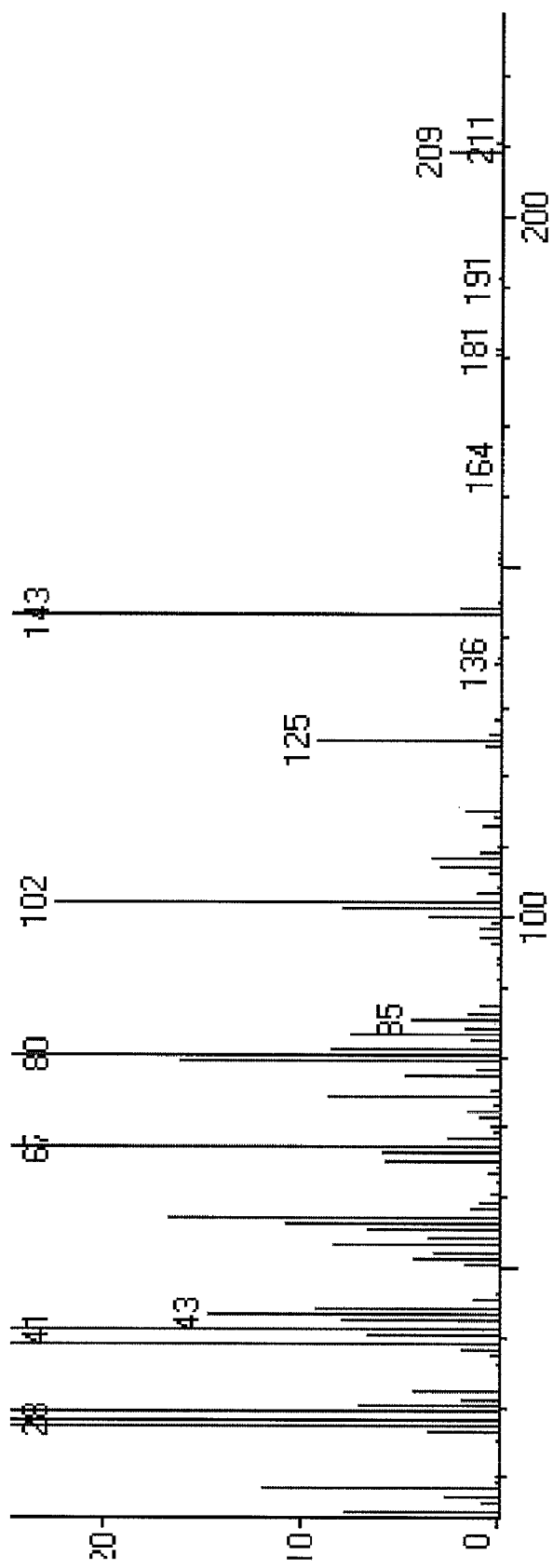

N-(2-cyclopentene-1-acetanoyl)-L-homoserine lactone (7k) was synthesized by the method described in Example 8. FIG. 12A is the GC-MS spectrum assaying the purity of the synthesis (inset shows the chemical structure). FIG. 12B is the NMR spectrum where: ¹H NMR (300 MHz, CDCl₃) δ=6.01 (d, 1H, NH), 5.81 (m, 1H, CH-vinyl), 5.69 (m, 1H, CH-vinyl), 4.57 (ddd, 1H, J=3.0 Hz, CH-lac), 4.5 (td, 1H, J=9.5 Hz, CH-lac), 4.33 (ddd, 1H, J=6.0 Hz, CH-lac), 3.15 (m, 1H, J=2.6 Hz, CH), 2.91 (ddd, 1H, J=1.2 Hz, CH-lac) 2.39-2.09 (m, 6H), 1.52 (ddd, 1H, J=5.0 Hz, CH-lac); ¹³C NMR (75 MHz, CDCl₃) δ=175.6, 173.0, 133.7, 132.1, 66.3, 49.5, 42.6, 42.6, 42.4, 32.1, 30.9, 29.8, 29.7; GC-MS: expected m/z=209, observed [M+]=209; [α$_D$]=+10.8 (c=2.6 mg/mL; CHCl₃); IR (cm⁻¹): 3311, 2923, 2851, 1775, 1643, 1546, 1173, 1016.

Example 22

N-(2-cyclopentene-1-acetanoyl)-D-homoserine lactone (7l)

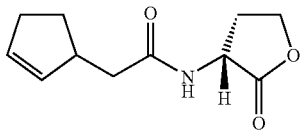

Figure 13A:
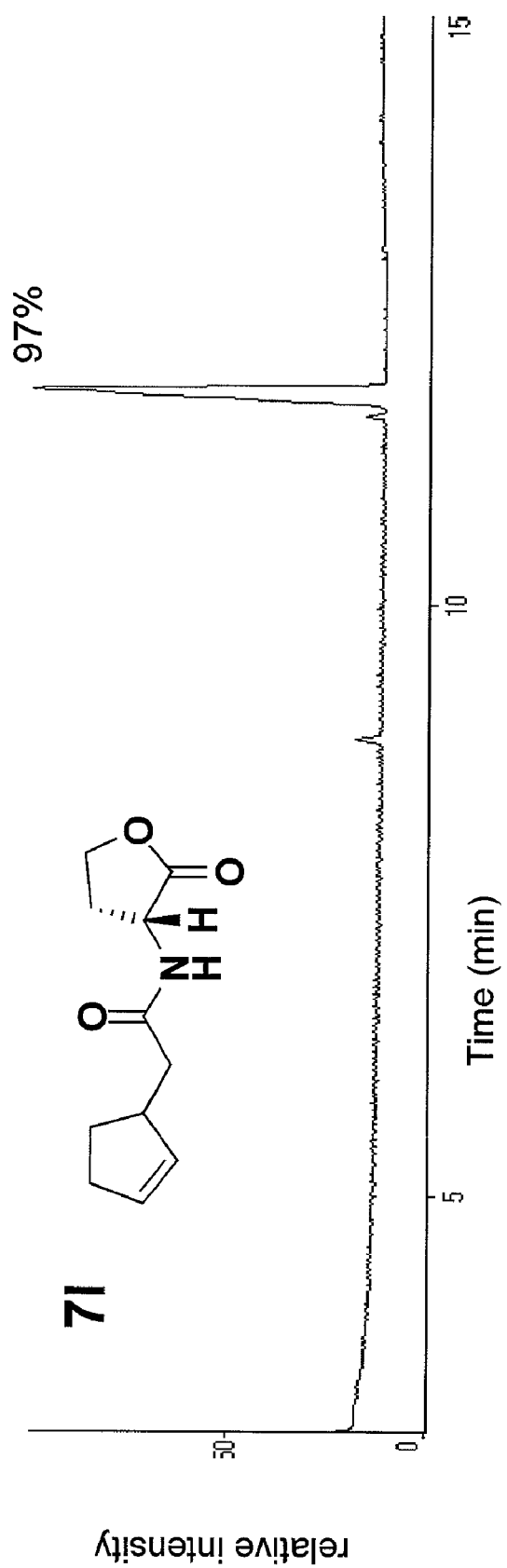
FIG. 13A shows a GC-MS spectrum and FIG. 13B shows an NMR spectrum for N-(2-cyclopentene-1-acetanoyl)-D-homoserine lactone (7l) produced by the scheme shown in FIG. 1A.
Figure 13B:
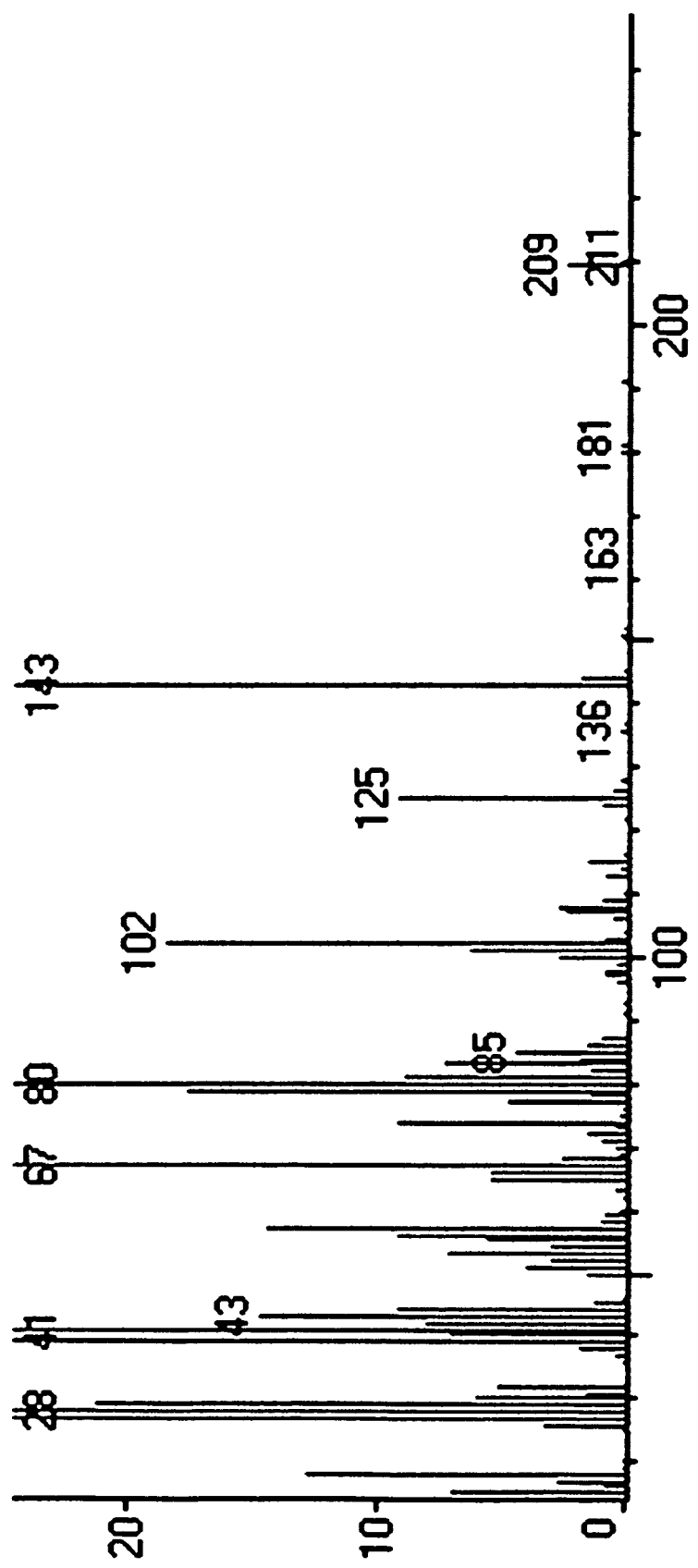

N-(2-cyclopentene-1-acetanoyl)-D-homoserine lactone (7l) was synthesized by the method described in Example 8. FIG. 13A is the GC-MS spectrum assaying the purity of the synthesis (inset shows the chemical structure). FIG. 13B is the NMR spectrum where: ¹H NMR (300 MHz, CDCl₃) δ=6.07 (s, 1H, NH), 5.81-5.70 (m, 1H, CH-vinyl), 5.69-5.66 (m, 1H, CH-vinyl), 4.60 (ddd, 1H, J=2.9 Hz, CH-lac), 4.47 (td, 1H, J=8.3 Hz, CH-lac), 4.33 (ddd, 1H, J=6.0 Hz, CH-lac), 3.15-3.10 (m, 1H), 2.91 (ddd, 1H, J=1.3 Hz, CH-lac) 2.40-2.08 (m, 6H), 1.54-1.43 (m, 1H, CH-lac); ¹³C NMR (75 MHz, CDCl₃) δ=173.0, 033.8, 133.7, 132.1, 132.0, 66.3, 49.5, 42.6, 42.6, 42.4, 32.0, 30.8, 29.7; GC-MS: expected m/z=209, observed [M+]=209; [α$_D$]=−12.9 (c=2.7 mg/mL; CHCl₃); IR (cm⁻¹): 3310, 2923, 2851, 2385, 1775, 1643, 1546, 1173, 1016.

Example 23

N-Boc-aminocapranoyl-L-homoserine lactone (7m)

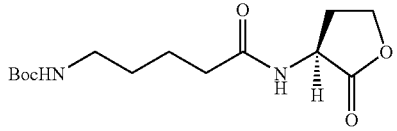

Figure 14:
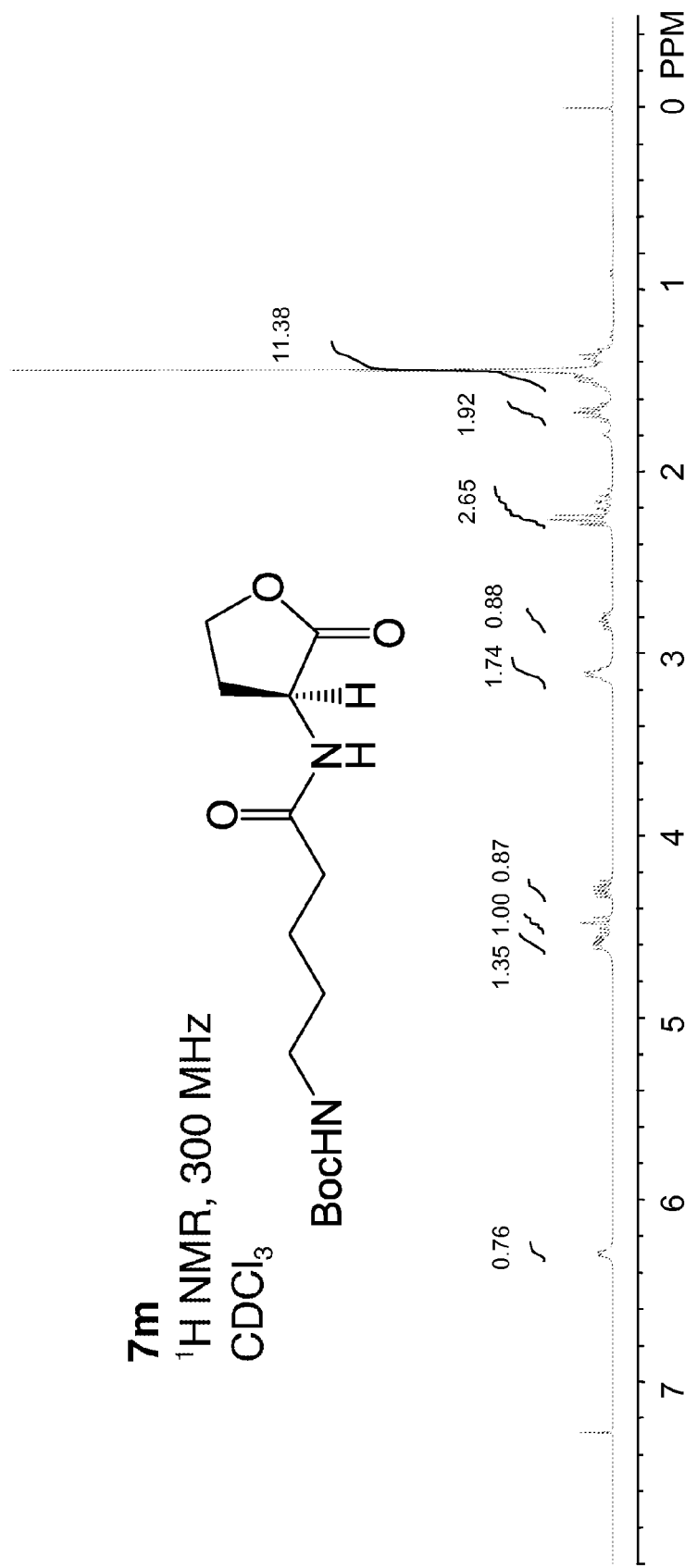
FIG. 14 shows an NMR spectrum for N-Boc-aminocapranoyl-L-homoserine lactone (7m) produced by the scheme shown in FIG. 1A.

N-Boc-aminocapranoyl-L-homoserine lactone (7m) was synthesized by the method described in Example 8. FIG. 14 is the NMR spectrum where: ¹H NMR (300 MHz, CDCl₃) δ=6.50 (d, 1H, NH), 4.65 (m, 2H, CH-lac, NH), 4.49 (td, 1H, J=9.0 Hz, CH-lac), 4.32 (ddd, 1H, J=6.1 Hz, CH-lac), 3.11 (q, 2H, J=6.3 Hz, CH₂), 2.79 (ddd, 1H, J=4.5 Hz, CH-lac), 2.28 (t, 2H, J=7.5 Hz, CH₂), 2.17 (ddd, 1H, J=6.8 Hz, CH-lac) 1.69 (p, 2H, J=7.4 Hz, CH₂), 1.52 (m, 12H); ¹³C NMR (75 MHz, CDCl₃) δ=175.8, 173.7, 156.2, 66.2, 49.2, 40.5, 36.0, 31.1, 30.3, 29.9, 28.6, 26.4, 25.1, 16.5; GC-MS: expected m/z=314, observed [M+Na]=337; [α$_D$]=+5.7 (c=2.1 mg/mL; CHCl₃); IR (cm⁻¹): 3684, 3455, 3020, 2401, 1781, 1693, 1511, 1216.

Example 24

N-monoethyl fumaroyl-L-homoserine lactone (7n)

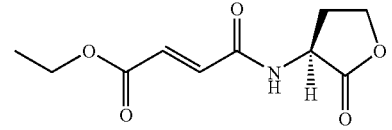

Figure 15A:
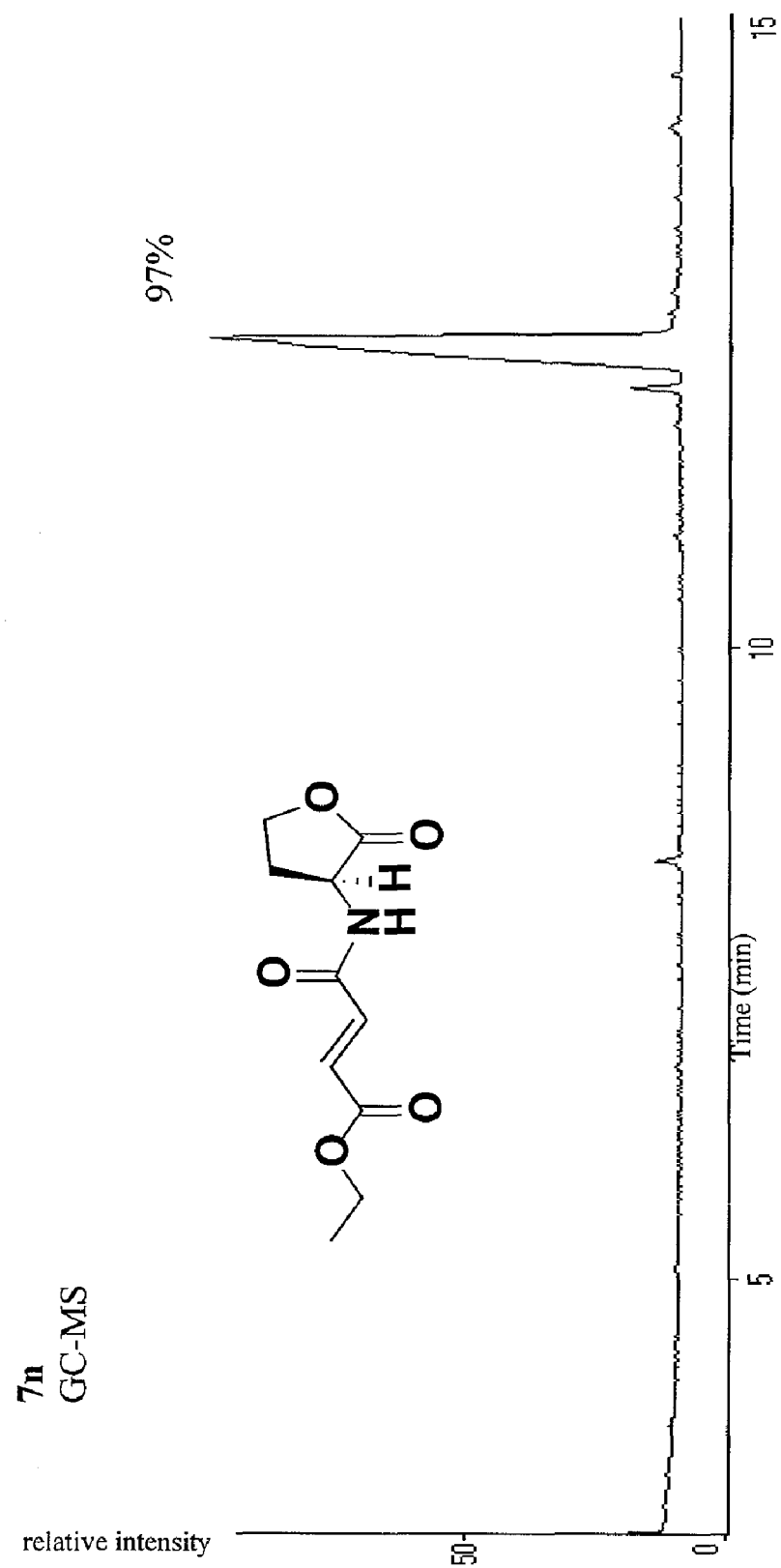
FIG. 15A shows a GC-MS spectrum and FIG. 15B shows an NMR spectrum for N-monoethyl fumaroyl-L-homoserine lactone (7n) produced by the scheme shown in FIG. 1A.
Figure 15B:
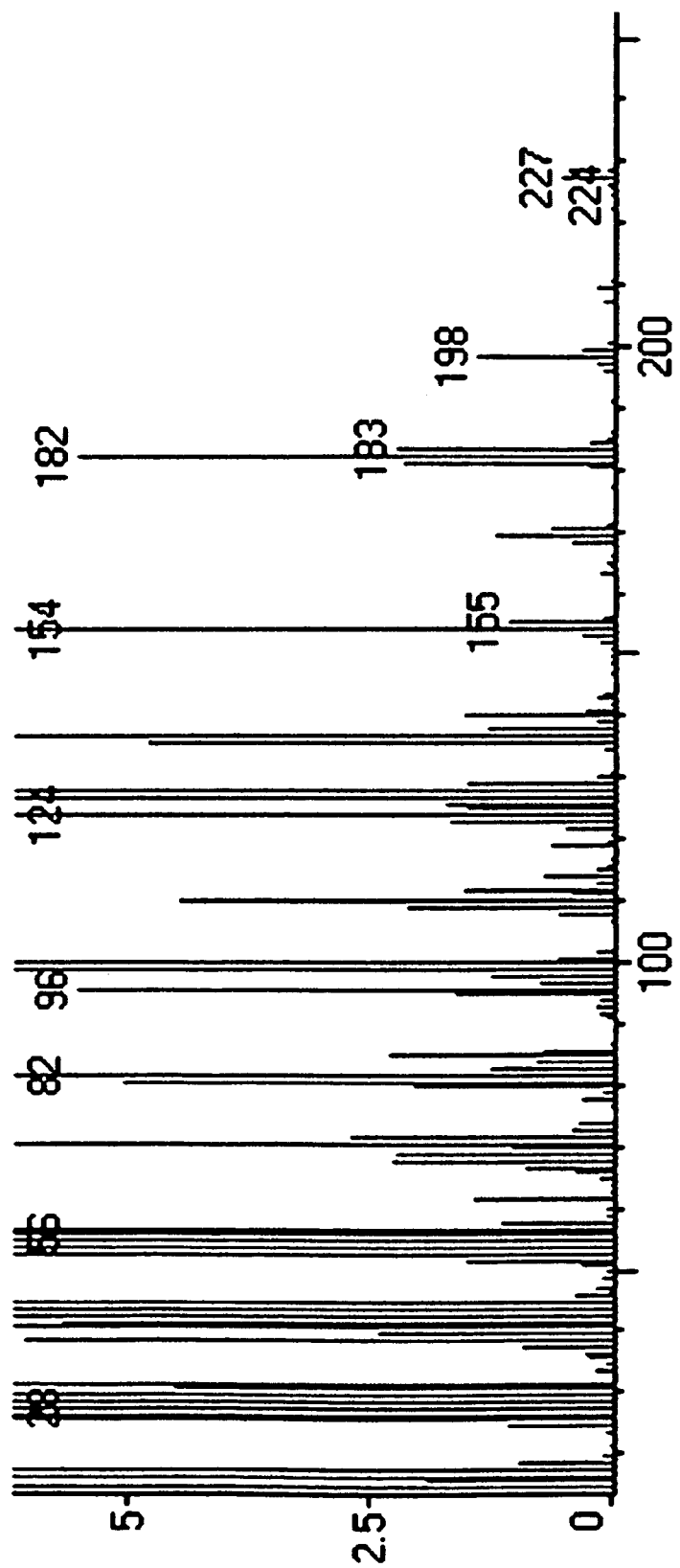

N-monoethyl fumaroyl-L-homoserine lactone (7n) was synthesized by the method described in Example 8. FIG. 15A is the GC-MS spectrum assaying the purity of the synthesis (inset shows the chemical structure). FIG. 15B is the NMR spectrum where: ¹H NMR (300 MHz, CDCl₃) δ=7.0 (d, 2H, Ar—H), 6.87 (d, 2H, Ar—H), 4.72 (ddd, 1H, J=6.3 Hz, CH-lac), 4.54 (td, 1H, J=1.3 Hz, CH-lac), 4.37 (ddd, 1H, J=6.0 Hz, CH-lac), 4.29 (q, 2H, J=7.1 Hz, CH₂), 2.91 (ddd, 1H, J=1.4 Hz, CH-lac), 2.31 (ddd, 1H, J=8.7 Hz, CH-lac) 1.47 (s, 2H, CH₂), 1.34 (t, 3H, J=7.1 Hz, CH₃); ¹³C NMR (75 MHz, CDCl₃) δ=175.2, 165.5, 164.4, 135.1, 131.8, 66.4, 61.6, 49.7, 30.4, 28.5, 14.3; GC-MS: expected m/z=227, observed [M+]=227; [α$_D$]=+4.7 (c=2.8 mg/mL; CHCl₃); IR (cm⁻¹): 3316, 2923, 1778, 1712, 1645, 1549, 1166.

Example 25

N-(4-bromophenylacetanoyl)-L-homoserine lactone (7o)

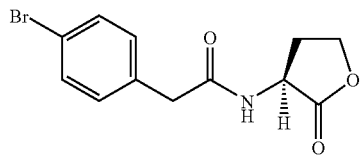

Figure 16A:
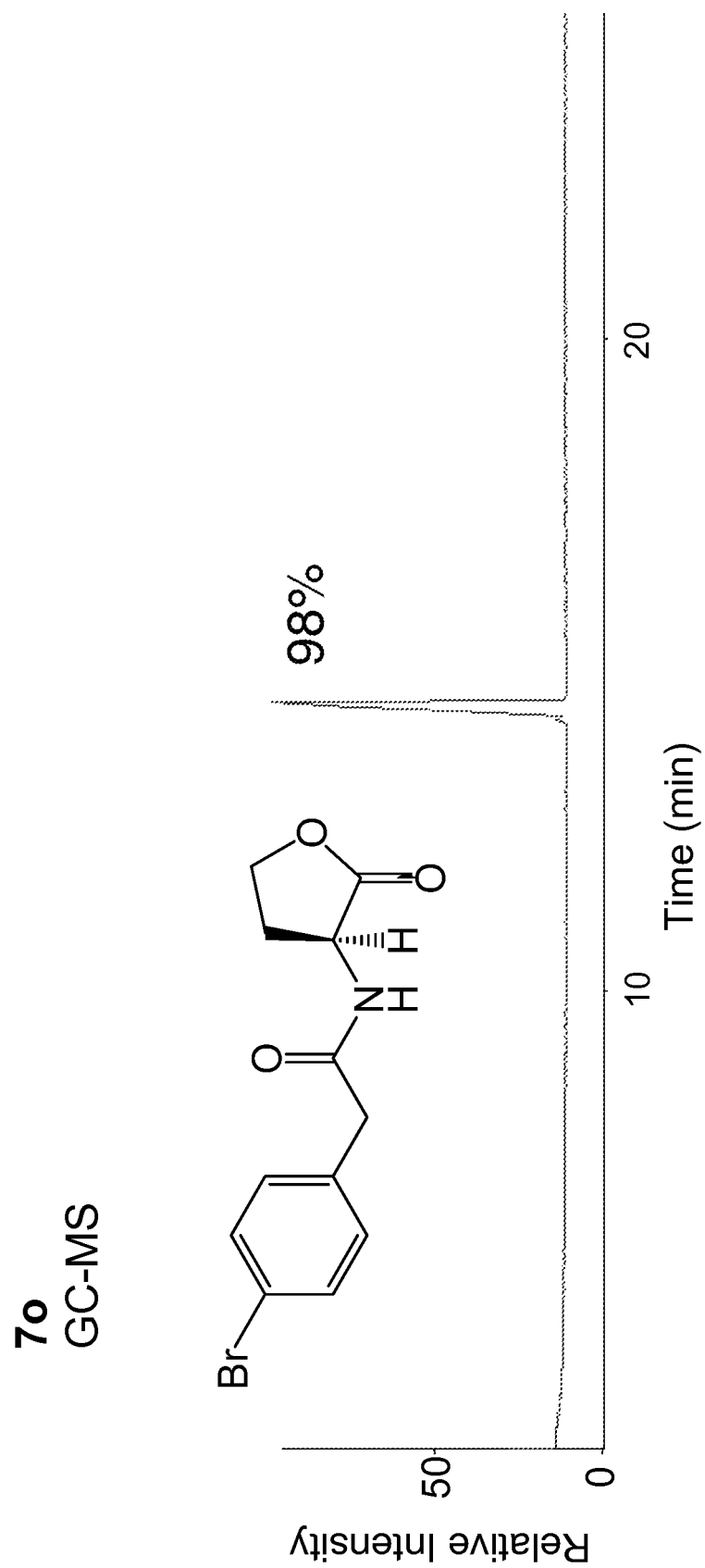
FIG. 16A shows a GC-MS spectrum and FIG. 16B shows an NMR spectrum for N-(4-bromophenylacetanoyl)-L-homoserine lactone (7o) produced by the scheme shown in FIG. 1A.
Figure 16B:
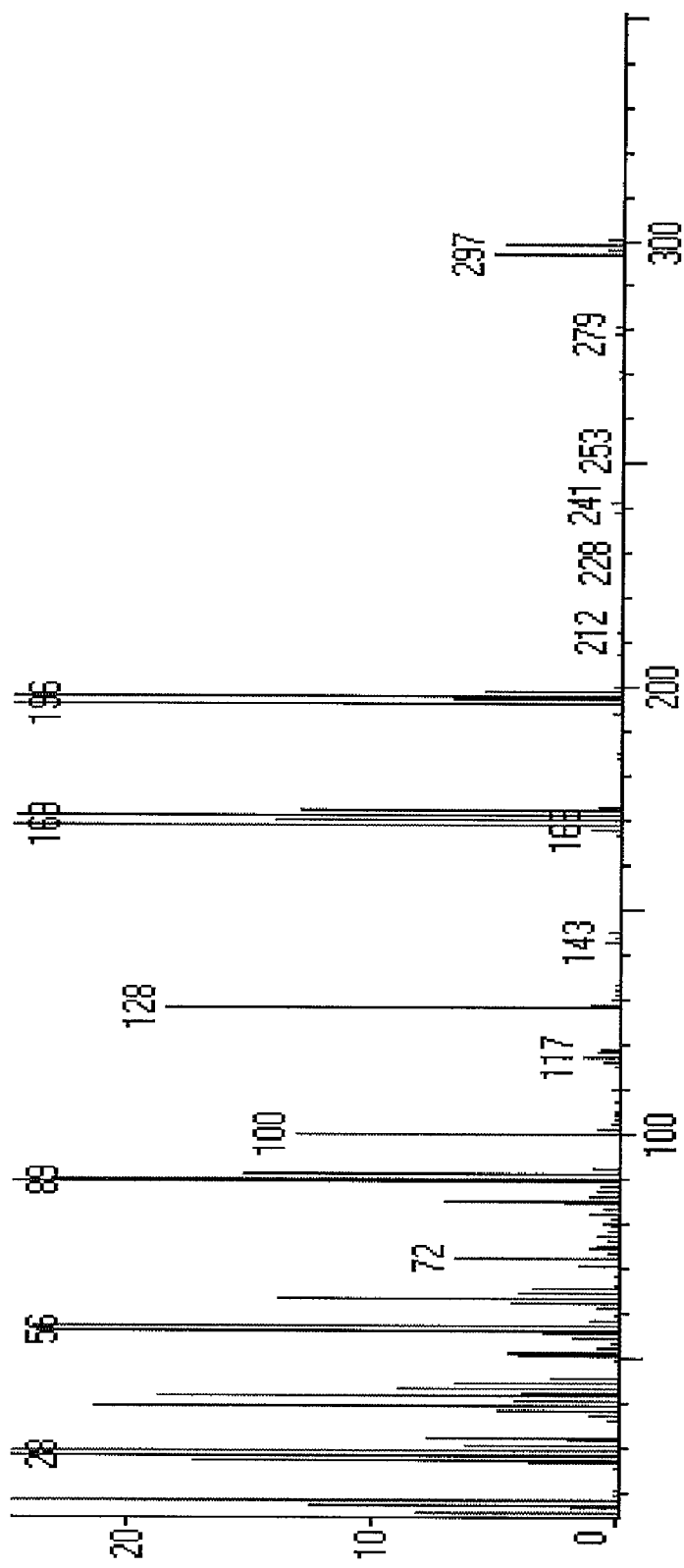

N-(4-bromophenylacetanoyl)-L-homoserine lactone (7o) was synthesized by the method described in Example 8. FIG. 16A is the GC-MS spectrum assaying the purity of the synthesis (inset shows the chemical structure). FIG. 16B is the NMR spectrum where: $^1$H NMR (300 MHz, CDCl$_3$) δ=7.49 (d, 2H, J=2.7 Hz, CH—Ar), 7.17 (d, 2H, J=2.7 Hz, CH—Ar), 6.02 (s, 1H, NH), 4.58 (ddd, 1H, J=6.2 Hz, CH-lac), 4.45 (td, 1H, J=1.2 Hz, CH-lac), 4.33 (ddd, 1H, J=5.9 Hz, CH-lac), 3.59 (s, 2H, CH$_2$), 2.87 (ddd, 2H, J=1.4 Hz, CH-lac), 2.19 (dd, 1H, J=8.9 Hz, CH-lac); $^{13}$C NMR (75 MHz, CDCl$_3$) δ=132.8, 131.9, 130.9, 65.8, 49.2, 30.1; GC-MS: expected m/z=297, observed [M+]=297; [α$_D$]=+3.8 (c=2.55 mg/mL; CHCl$_3$); IR (cm$^{-1}$): 3419, 3020, 2401, 1782, 1672, 1216.

Example 26

N-(trans-cinamoyl)-L-homoserine lactone (7p)

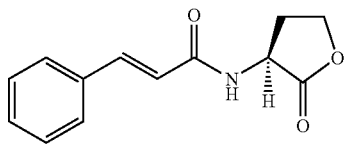

Figure 17A:
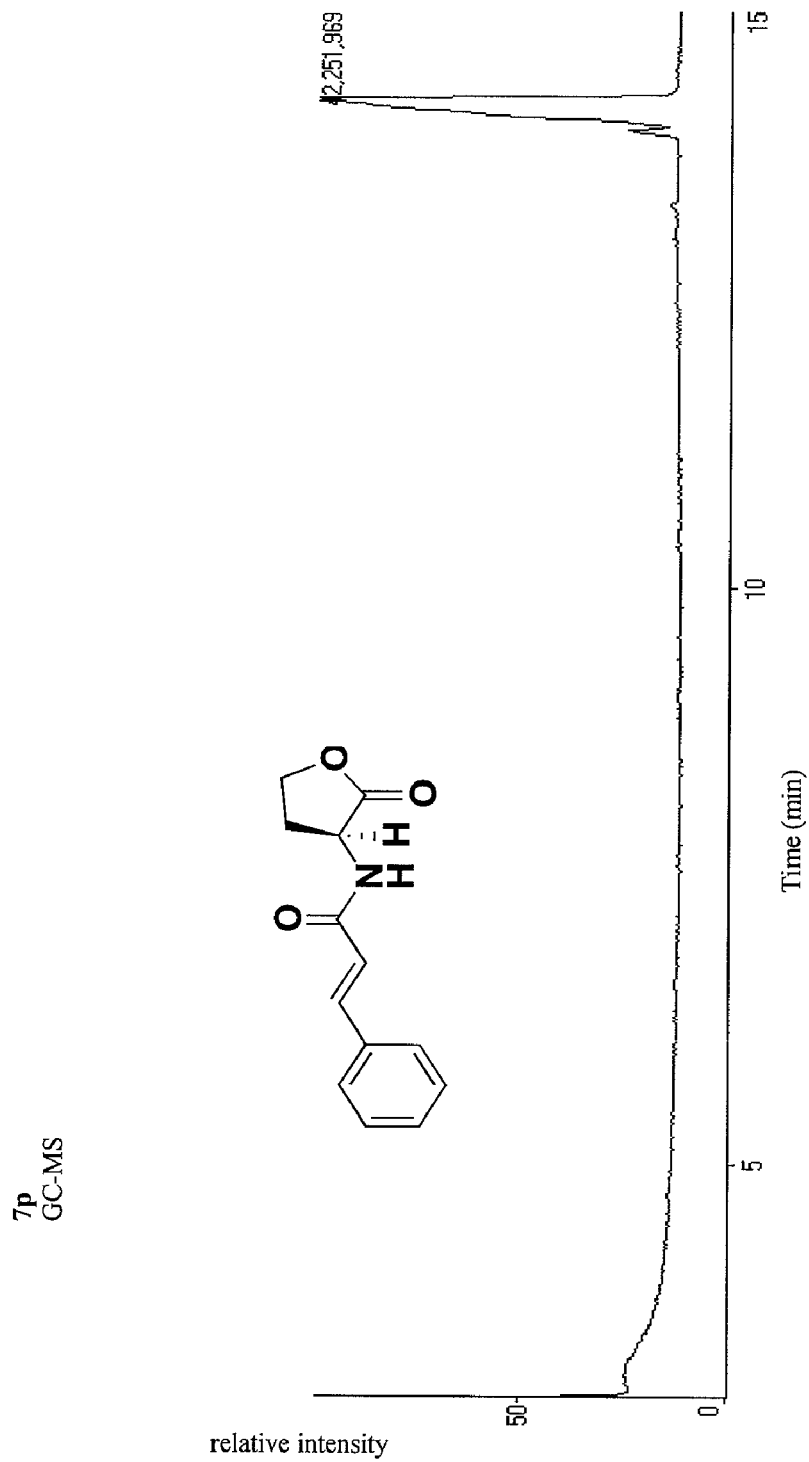
FIG. 17A shows a GC-MS spectrum and FIG. 17B shows an NMR spectrum for N-(trans-cinamoyl)-L-homoserine lactone (7p) produced by the scheme shown in FIG. 1A.
Figure 17B:
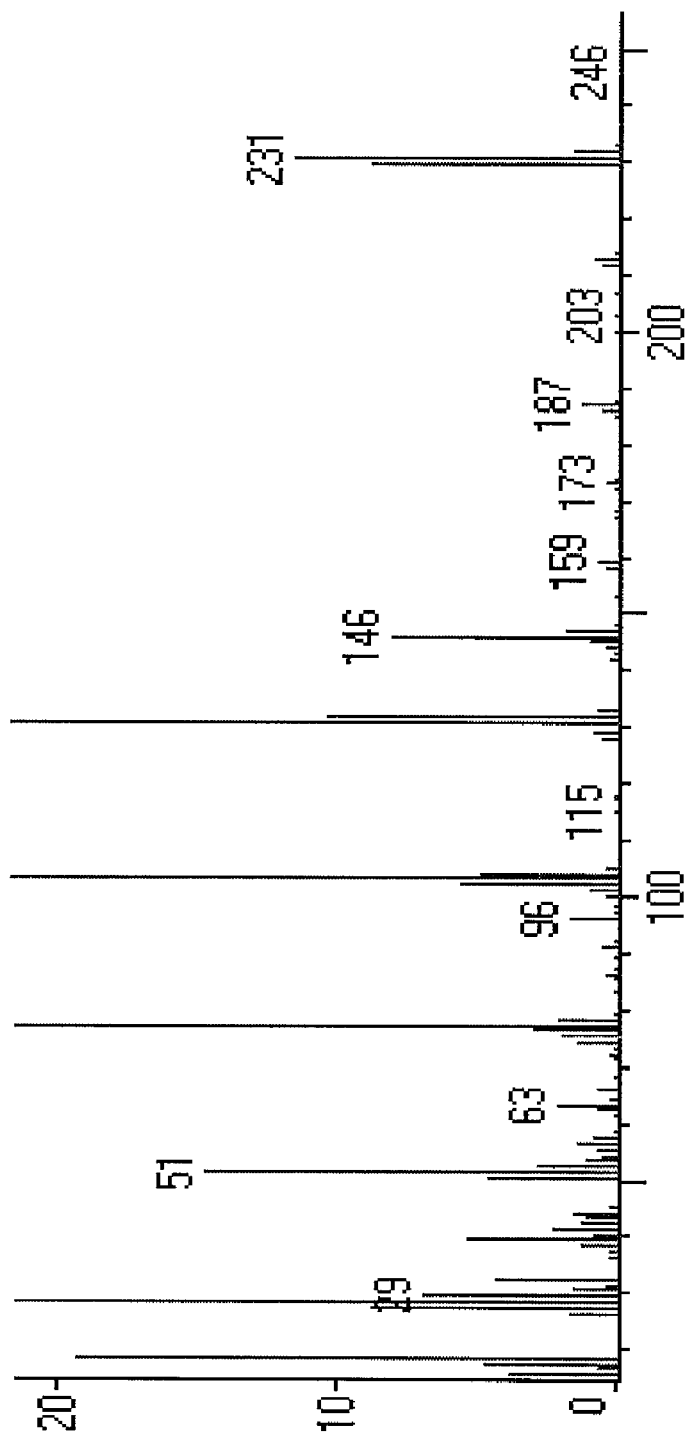

N-(trans-cinamoyl)-L-homoserine lactone (7p) was synthesized by the method described in EXAMPLE 8. FIG. 17A is the GC-MS spectrum assaying the purity of the synthesis (inset shows the chemical structure). FIG. 17B is the NMR spectrum: $^1$H NMR (300 MHz, CDCl$_3$) δ=7.66 (d, 2H, Ar—H), 7.48 (m, 2H, Ar—H), 7.36 (m, 3H, Ar—H), 6.51 (d, 1H, J=5.9 Hz, NH), 6.49 (d, 1H, J=15.7 Hz, H-vinyl), 4.78 (ddd, 1H, J=6.4 Hz, CH-lac), 4.53 (td, 1H, J=8.9 Hz, CH-lac), 4.37 (ddd, 1H, J=5.9 Hz, CH-lac) 2.92 (ddd, 1H, J=1.0 Hz, CH-lac), 2.32 (td, 1H, J=8.9 Hz, CH-lac); $^{13}$C NMR (75 MHz, CDCl$_3$) δ=176.0, 166.6, 142.6, 134.6, 130.2, 129.1, 128.2, 119.5, 66.5, 49.7, 30.7; GC-MS: expected m/z=231, observed [M+]=231; [α$_D$]=+30.2 (c=2.45 mg/mL; CHCl$_3$); IR (cm$^{-1}$): 3312, 2923, 1774, 1644, 1547, 1173, 1016.

Example 27

N-(4-phenylbutanoyl)-L-homoserine lactone (7q)

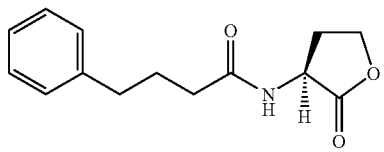

Figure 18A:
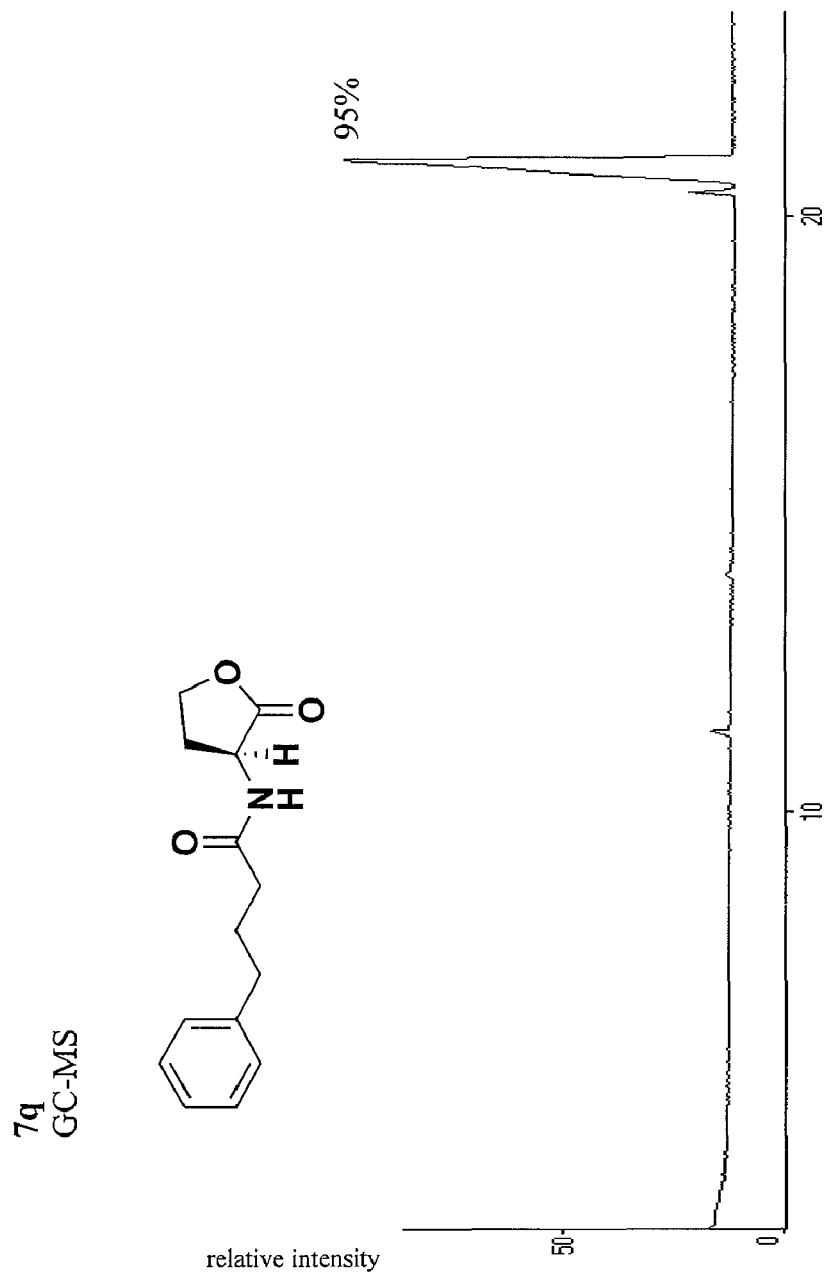
FIG. 18A shows a GC-MS spectrum and FIG. 18B shows an NMR spectrum for N-(4-phenylbutanoyl)-L-homoserine lactone (7q) produced by the scheme shown in FIG. 1A.
Figure 18B:
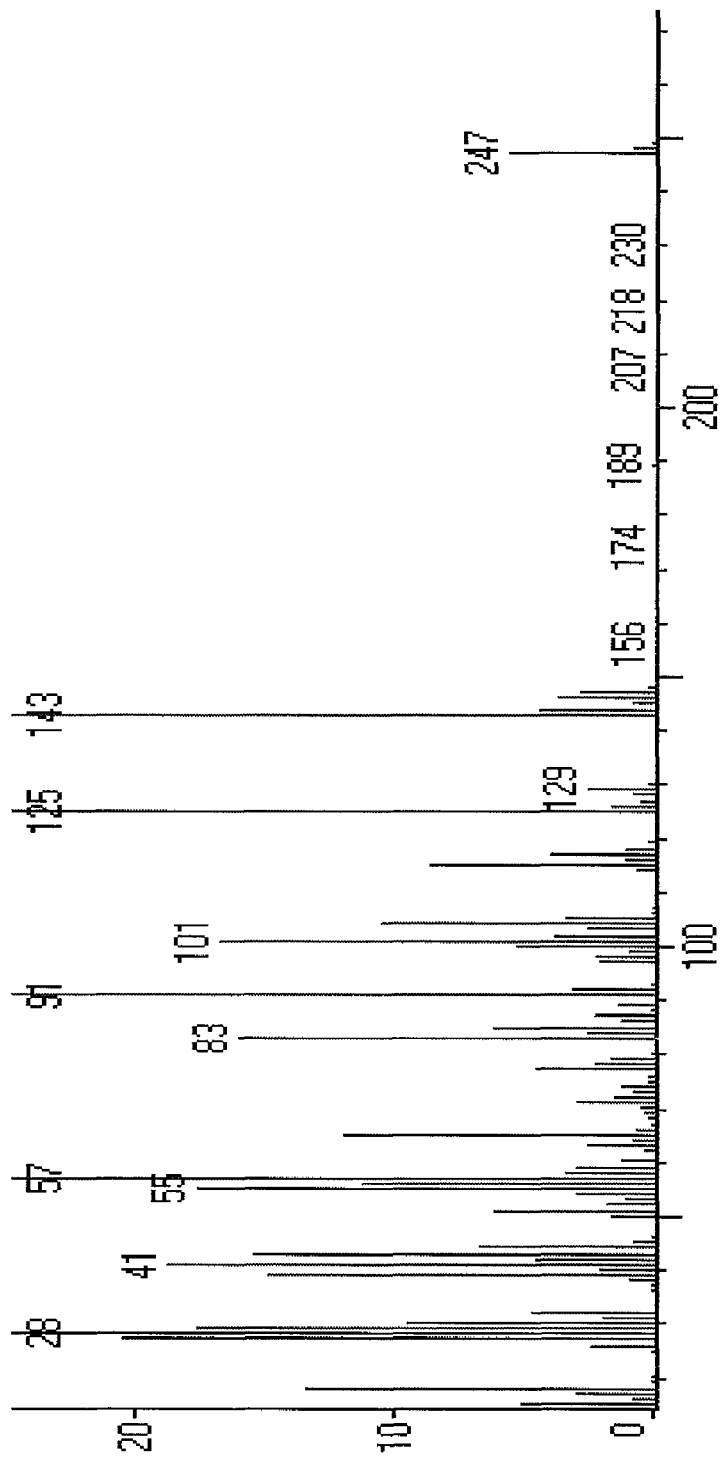

N-(4-phenylbutanoyl)-L-homoserine lactone (7q) was synthesized by the method described in Example 8. FIG. 18A is the GC-MS spectrum assaying the purity of the synthesis (inset shows the chemical structure). FIG. 18B is the NMR spectrum where: $^1$H NMR (300 MHz, CDCl$_3$) δ=7.31 (m, 2H, Ar—H), 7.21 (m, 3H, Ar—H), 6.13 (d, 1H, J=5.3 Hz, NH), 4.59 (ddd, 1H, J=6.2 Hz, CH-lac), 4.47 (td, 1H, J=1.0 Hz, CH-lac), 4.30 (ddd, 1H, J=5.7 Hz, CH-lac), 2.85 (ddd, 1H, J=1.1 Hz, CH-lac), 2.68 (t, 2H, J=7.3 Hz, CH$_2$), 2.36 (t, 2H, J=6.7 Hz, CH$_2$), 2.18 (d, 1H, J=3.2 Hz, CH-lac), 2.04 (p, 2H, J=7.4 Hz, CH$_2$); $^{13}$C NMR (75 MHz, CDCl$_3$) δ=175.7, 173.5, 167.7, 141.5, 128.7, 128.6, 126.2, 115.0, 66.3, 49.4, 35.5, 35.3, 30.7, 27.0; GC-MS: expected m/z=247, observed [M+]=247; [α$_D$]=+27.9 (c=6.7 mg/mL; CHCl$_3$); IR (cm$^{-1}$): 3314, 2935, 2358, 2331, 1771, 1652, 1447, 1173.

Example 28

N-(4-phenylbutanoyl)-D-homoserine lactone (7r)

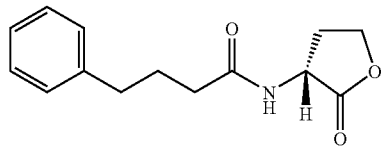

Figure 19A:
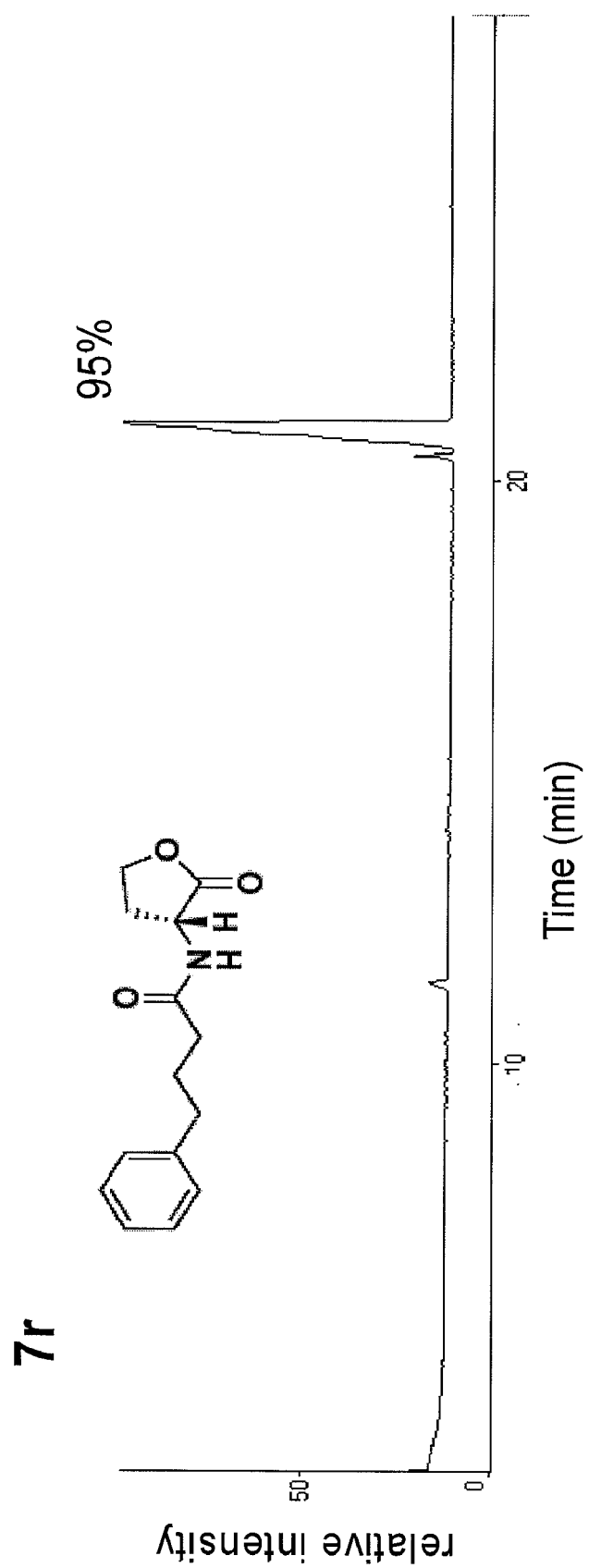
FIG. 19A shows a GC-MS spectrum and FIG. 19B shows an NMR spectrum for N-(4-phenylbutanoyl)-D-homoserine lactone (7r) produced by the scheme shown in FIG. 1A.
Figure 19B:
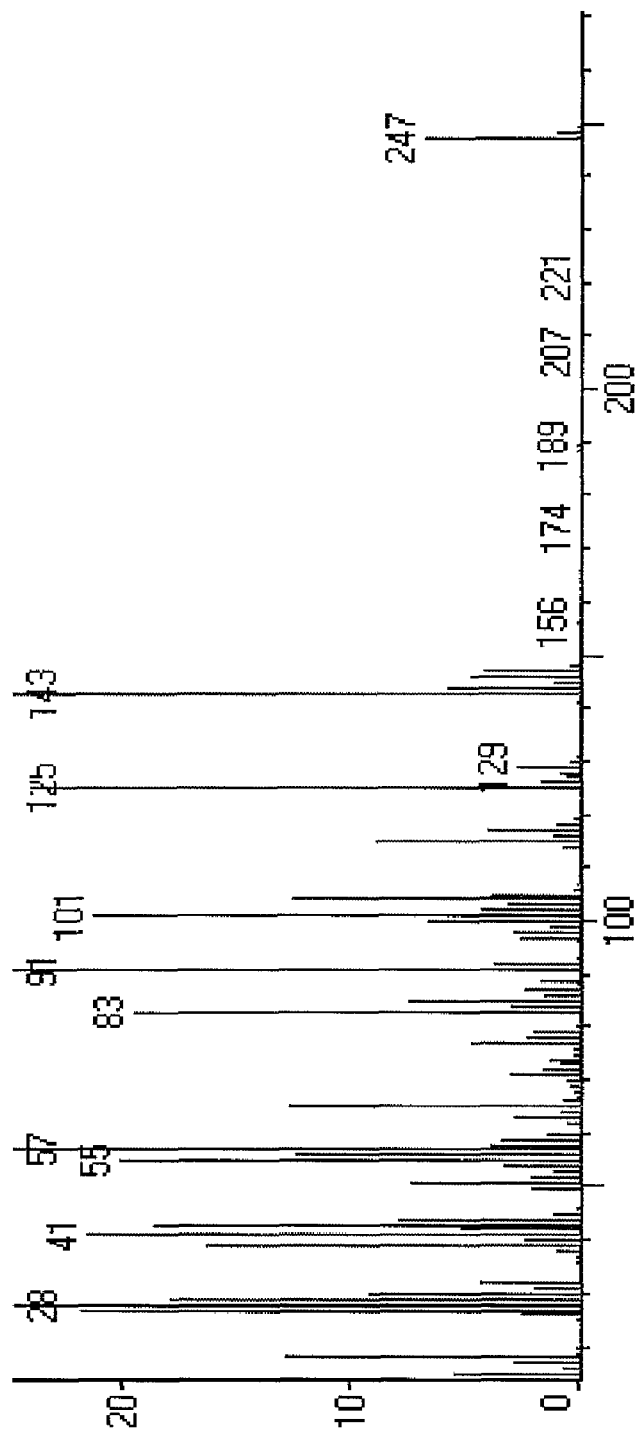

N-(4-phenylbutanoyl)-D-homoserine lactone (7r) was synthesized by the method described in Example 8. FIG. 19A is the GC-MS spectrum assaying the purity of the synthesis (inset shows the chemical structure). FIG. 19B is the NMR spectrum: $^1$H NMR (300 MHz, CDCl$_3$) δ=7.31 (m, 2H, Ar—H), 7.21 (m, 3H, Ar—H), 6.10 (d, 1H, J=4.7 Hz, NH), 4.59 (ddd, 1H, J=5.9 Hz, CH-lac), 4.47 (td, 1H, J=1.2 Hz, CH-lac), 4.31 (ddd, 1H, J=5.8 Hz, CH-lac), 2.86 (ddd, 1H, J=1.2 Hz, CH-lac), 2.69 (t, 2H, J=7.2 Hz, CH$_2$), 2.36 (t, 2H, J=7.8 Hz, CH$_2$), 2.18 (ddd, 1H, J=3.2 Hz, CH-lac), 2.04 (p, 2H, J=7.1 Hz, CH$_2$); $^{13}$C NMR (75 MHz, CDCl$_3$) δ=175.6, 173.5, 167.6, 163.9, 141.5, 128.7, 128.6, 126.2, 115.1, 115.0, 66.3, 59.4, 49.4, 35.5, 35.3, 30.7, 27.0; GC-MS: expected m/z=247, observed [M+]=247; [α$_D$]=−24.1 (c=4.0 mg/mL; CHCl$_3$); IR (cm$^{-1}$): 3309, 2966, 2685, 23559, 2338, 1772, 1669, 1539, 1556, 1221, 1201.

Example 29

N-(3-oxo-hexanoyl)-L-homoserine lactone (8a)

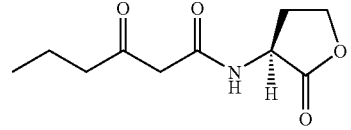

Figure 20:
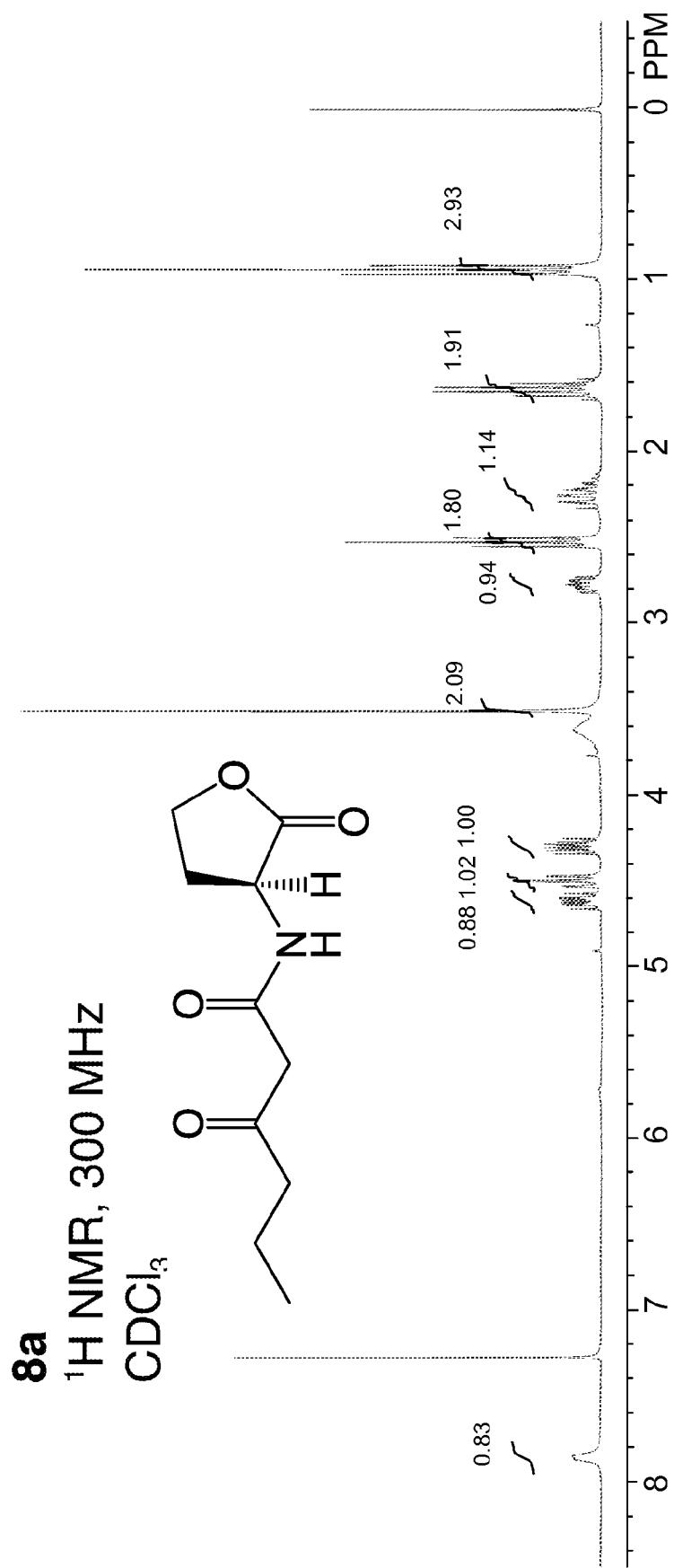
FIG. 20 shows an NMR spectrum for N-(3-oxo-hexanoyl)-L-homoserine lactone (8a) produced by the scheme shown in FIG. 1A.

N-(3-oxo-hexanoyl)-L-homoserine lactone (8a) was synthesized by the method described in Example 9. FIG. 20 is the NMR spectrum (inset shows the chemical structure) where: $^1$H NMR (300 MHz, CDCl$_3$) δ=7.85 (s, 1H, NH), 4.67 (ddd, 1H, J=6.7 Hz, CH-lac), 4.57 (td, 1H, J=1.3 Hz, CH-lac), 4.34 (ddd, 1H, J=6.1 Hz, CH-lac), 3.52 (s, 2H, CH$_2$), 2.82 (dddd, 1H, J=1.2 Hz, CH-lac), 2.56 (t, 2H, J=7.2 Hz, CH$_2$) 2.33 (ddd, 1H, J=2.4 Hz, CH-lac), 1.64 (p, 2H, J=7.2 Hz, CH$_2$), 0.98 (t, 3H, J=6.5 Hz, CH$_3$); $^{13}$C NMR (75 MHz, CDCl$_3$) δ=204.7, 173.1, 164.9, 64.2, 47.4, 46.3, 44.0, 28.1, 15.1, 11.8; MS(ESI): expected m/z=213, observed [M+Na]=236; [α$_D$]=+12.2 (c=2.7 mg/mL; CHCl$_3$); IR (cm$^{-1}$): 3286, 3966, 1783, 1718, 1646, 1545, 1171.

Example 30

N-(3-oxo-octanoyl)-L-homoserine lactone (8b)

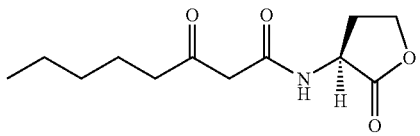

Figure 21:
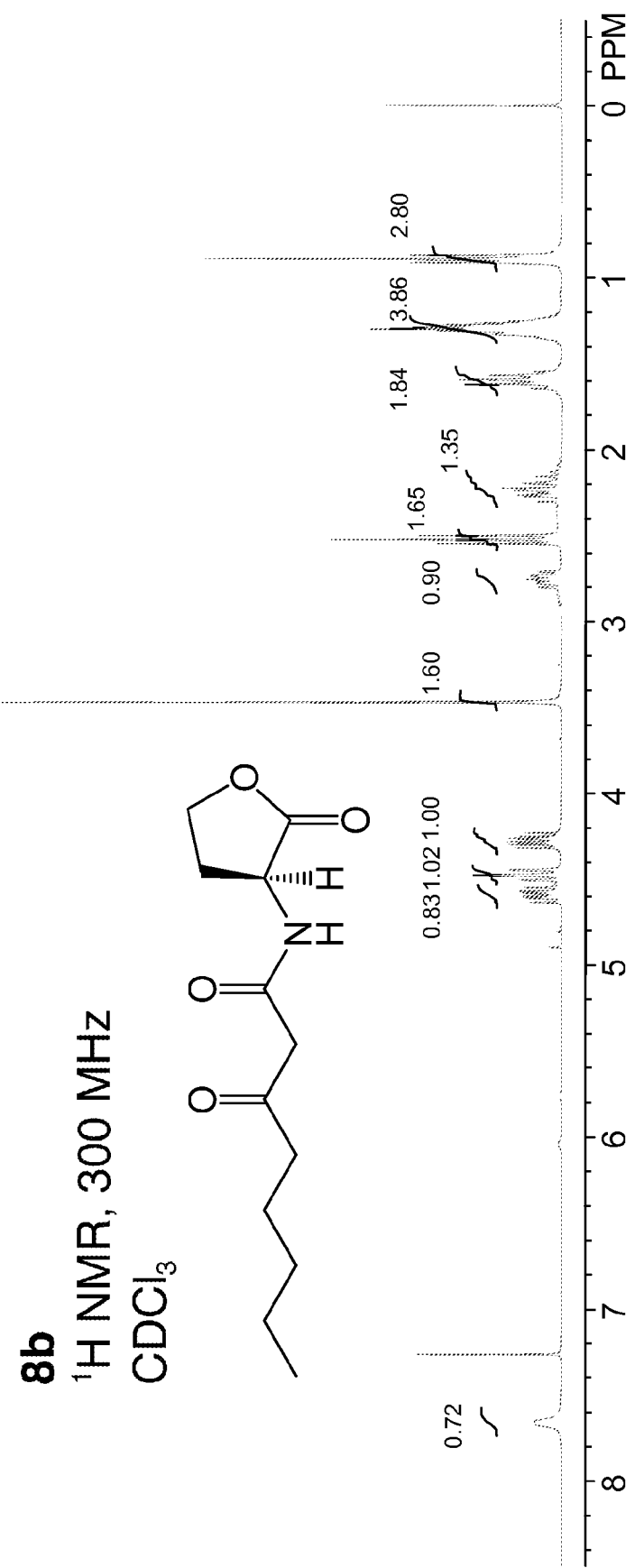
FIG. 21 shows an NMR spectrum for N-(3-oxo-octanoyl)-L-homoserine lactone (8b) produced by the scheme shown in FIG. 1A.

N-(3-oxo-octanoyl)-L-homoserine lactone (8b) was synthesized by the method described in Example 9. FIG. 21 is the NMR spectrum (inset shows the chemical structure) where: $^1$H NMR (300 MHz, CDCl$_3$) δ=7.95 (s, 1H, NH), 4.67 (ddd, 1H, J=6.7 Hz, CH-lac), 4.53 (td, 1H, J=1.3 Hz, CH-lac), 4.34 (ddd, 1H, J=6.1 Hz, CH-lac), 3.52 (s, 2H, CH$_2$), 2.81 (dddd, 1H, J=1.2 Hz, CH-lac), 2.57 (t, 2H, J=7.2 Hz, CH$_2$) 2.34 (ddd, 1H, J=2.4 Hz, CH-lac), 1.64 (p, 2H, J=7.2 Hz, CH$_2$), 1.43 (m, 4H, J=6.4 Hz, (CH$_2$)$_4$), 0.91 (t, 3H, J=6.5 Hz, CH$_3$); $^{13}$C NMR (75 MHz, CDCl$_3$) δ=206.7, 175.0, 166.7, 66.3, 66.1, 49.3, 48.4, 44.0, 31.3, 30.0, 23.2, 22.6, 14.1; MS(ESI): expected m/z=241, observed [M+Na]=264; [α$_D$]=+16.9 (c=2.7 mg/mL; CHCl$_3$); IR (cm$^{-1}$): 3684, 3020, 2401, 1783, 1712, 1674, 1527, 1216.

Example 31

N-(3-oxo-decanoyl)-L-homoserine lactone (8c)

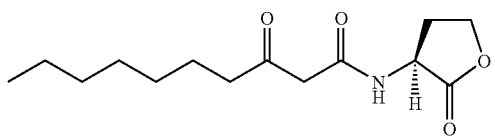

Figure 22:
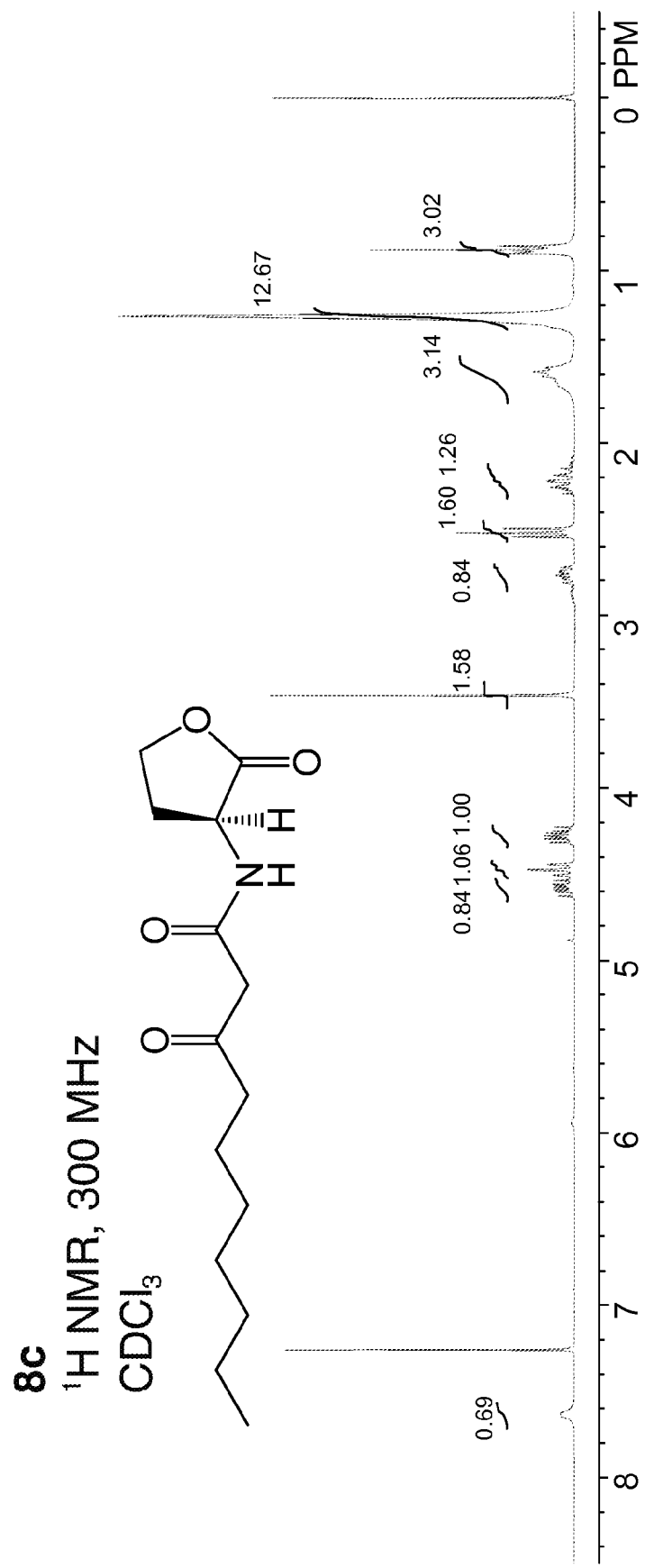
FIG. 22 shows an NMR spectrum for N-(3-oxo-decanoyl)-L-homoserine lactone (8c) produced by the scheme shown in FIG. 1A.

N-(3-oxo-decanoyl)-L-homoserine lactone (8c) was synthesized by the method described in Example 9. FIG. 22 shows the NMR spectrum (inset shows the chemical structure) where: $^1$H NMR (300 MHz, CDCl$_3$) 7.68 (d, 1H, J=4.9 Hz, NH), 4.65 (ddd, 1H, J=9.2 Hz, CH-lac), 4.53 (t, 1H, J=8.9 Hz, CH-lac), 4.32 (ddd, 1H, J=6.2 Hz, CH-lac), 3.47 (s, 2H, CH$_2$), 2.79 (dddd, 1H, J=1.3 Hz, CH-lac), 2.55 (t, 2H, J=7.3 Hz, CH$_2$), 2.32 (ddd, 1H, J=2.4 Hz, CH-lac), 1.61 (m, 2H, CH$_2$), 1.28 (m, 8H, (CH$_2$)$_4$), 0.89 (t, 3H, J=5.4 Hz, CH$_3$); $^{13}$C NMR (75 MHz, CDCl$_3$) δ=206.7, 175.1, 166.6, 66.3, 66.1, 49.2, 48.4, 44.1, 31.8, 29.9, 29.2, 29.1, 23.6, 22.8, 14.2; MS(ESI): expected m/z=269, observed [M+Na]=292; [α$_D$]=+16.7 (c=3.4 mg/mL; CHCl$_3$); IR (cm$^{-1}$): 3295, 2923, 2851, 1775, 1716, 1645, 1547, 1176.

Example 32

N-(3-oxo-dodecanoyl)-L-homoserine lactone (8d)

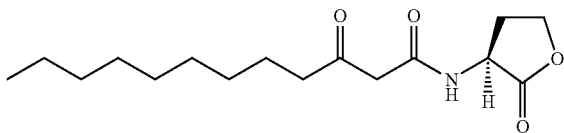

Figure 23:
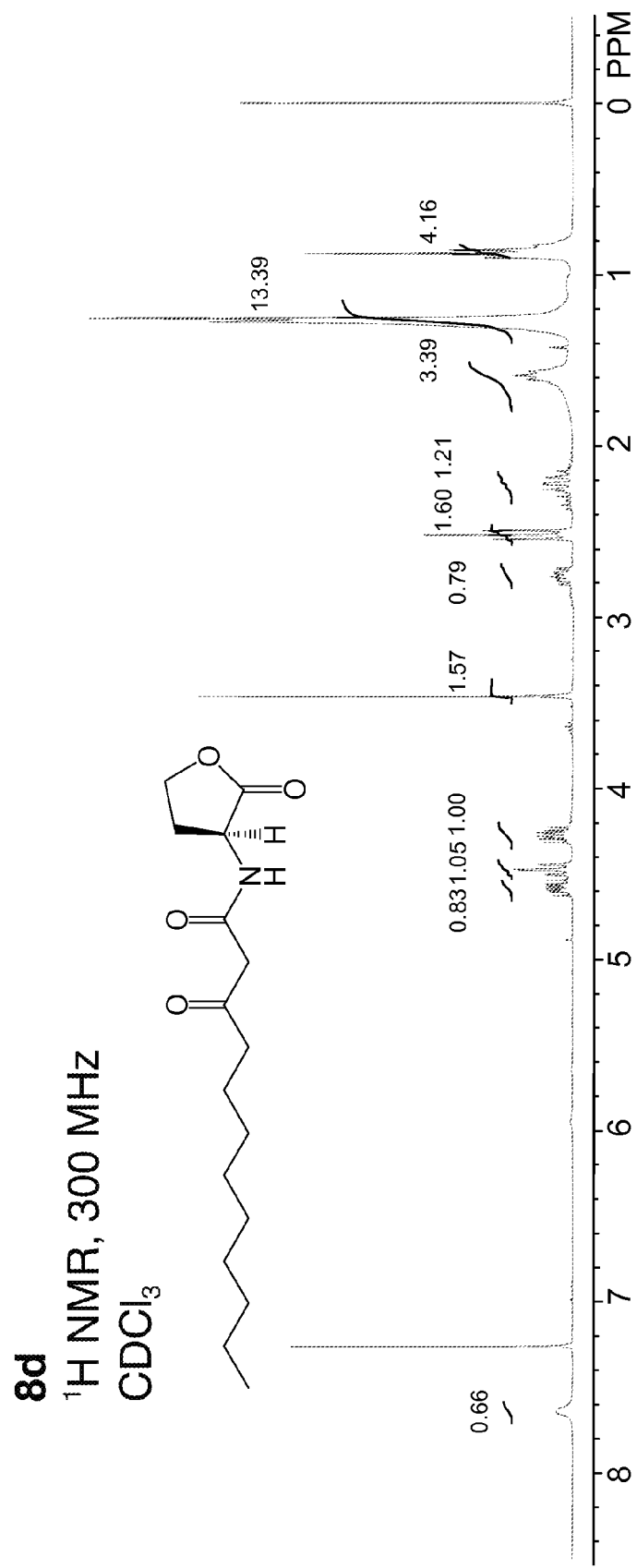
FIG. 23 shows an NMR spectrum for N-(3-oxo-dodecanoyl)-L-homoserine lactone (8d) produced by the scheme shown in FIG. 1A.

N-(3-oxo-dodecanoyl)-L-homoserine lactone (8d) was synthesized by the method described in Example 9. FIG. 23 is the NMR spectrum (inset shows the chemical structure) where: $^1$H NMR (300 MHz, CDCl$_3$) 7.68 (d, 1H, J=6.0 Hz, NH), 4.65 (ddd, 1H, J=5.9 Hz, CH-lac), 4.50 (td, 1H, J=1.1 Hz, CH-lac), 4.32 (ddd, 1H, J=6.1 Hz, CH-lac), 3.47 (s, 2H, CH$_2$), 2.79 (ddd, 1H, J=7.0 Hz, CH-lac), 2.55 (t, 2H, J=7.3 Hz, CH$_2$), 2.29 (ddd, 1H, J=2.2 Hz, CH-lac), 1.60 (m, 2H, CH$_2$), 1.26 (m, 12H, (CH$_2$)$_6$), 0.89 (t, 3H, J=6.1 Hz, CH$_3$); $^{13}$C NMR (75 MHz, CDCl$_3$) δ=206.7, 175.1, 174.1, 166.7, 66.3, 66.1, 49.4, 49.2, 48.9, 48.4, 44.1, 36.4, 32.0, 30.7, 29.9, 29.6, 29.5, 29.5, 29.4, 29.2, 25.7; MS(ESI): expected m/z=297, observed [M+Na]=320; [α$_D$]=+11.8 (c=3.6 mg/mL; CHCl$_3$); IR (cm$^{-1}$): 3295, 2922, 2851, 1775, 1716, 1644, 1547, 1171, 1016.

Example 33

N-(3-oxo-tetradecanoyl)-L-homoserine lactone (8e)

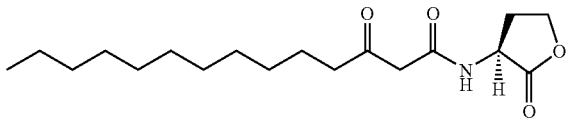

Figure 24:
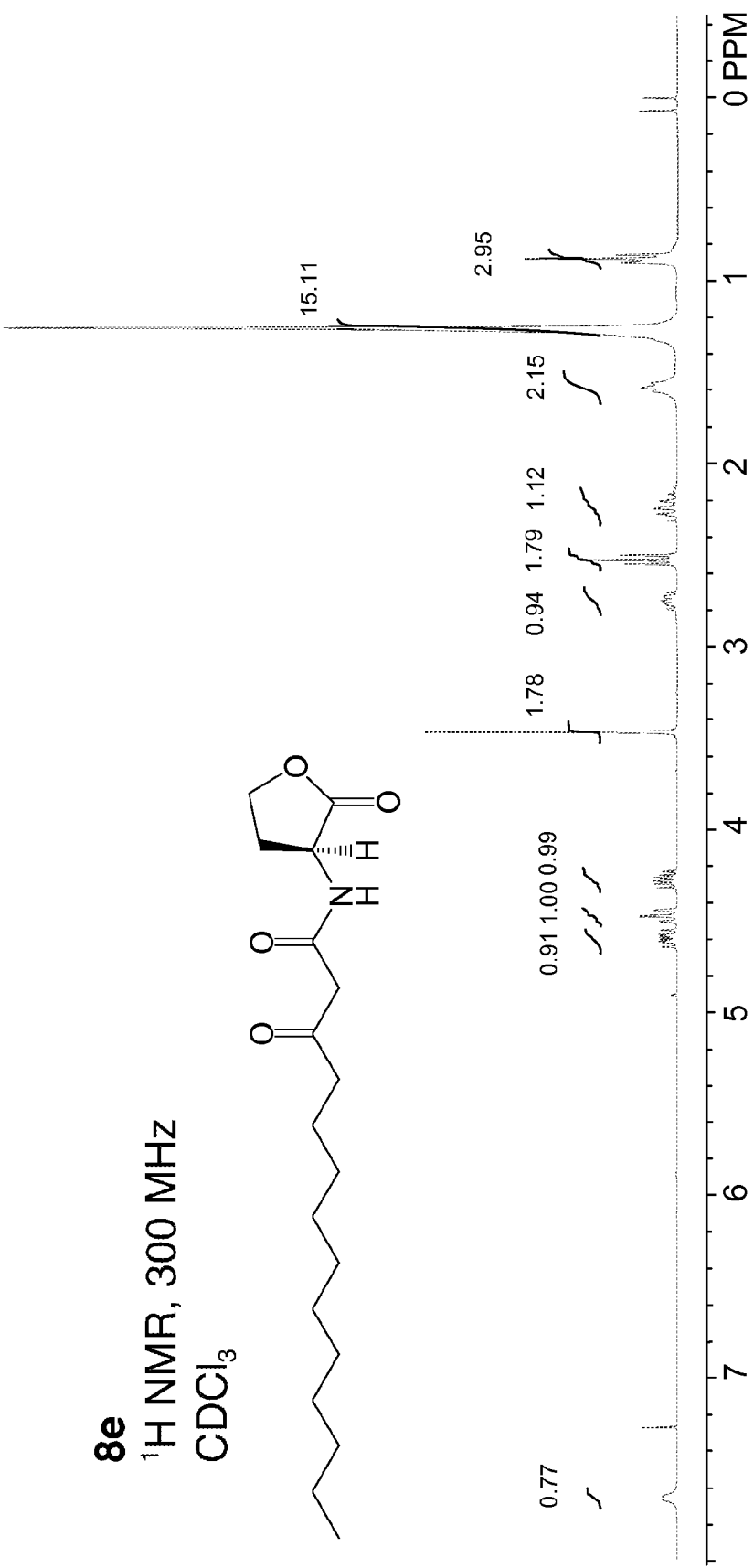
FIG. 24 shows an NMR spectrum for N-(3-oxo-tetradecanoyl)-L-homoserine lactone (8e) produced by the scheme shown in FIG. 1A.

N-(3-oxo-tetradecanoyl)-L-homoserine lactone (8e) was synthesized by the method described in Example 9. FIG. 24 is the NMR spectrum (inset shows the chemical structure) where: $^1$H NMR (300 MHz, CDCl$_3$) 7.68 (d, 1H, J=6.0 Hz, NH), 4.66 (ddd, 1H, J=5.9 Hz, CH-lac), 4.56 (td, 1H, J=1.1 Hz, CH-lac), 4.34 (ddd, 1H, J=6.1 Hz, CH-lac), 3.50 (s, 2H, CH$_2$), 2.86 (ddd, 1H, J=7.0 Hz, CH-lac), 2.30 (t, 2H, J=7.3 Hz, CH$_2$), 2.28 (ddd, 1H, J=2.2 Hz, CH-lac), 1.60 (in, 2H, CH$_2$), 1.26 (m, 12H, (CH$_2$)$_6$), 0.89 (t, 3H, J=6.1 Hz, CH$_3$); $^{13}$C NMR (75 MHz, CDCl$_3$) δ=175.0, 166.7, 66.3, 66.0, 49.5, 36.1, 32.1, 30.7, 29.8, 29.6, 29.5, 29.5, 29.4, 29.2, 25.7; MS(ESI): expected m/z=325, observed [M+Na]=348; [α$_D$]=+14.0 (c=2.5 mg/mL; CHCl$_3$); IR (cm$^{-1}$): 3921, 3315, 2852, 1777, 1716, 1645, 1548, 1174, 1014.

Example 34

N-(3-oxo-4-phenylbutanoyl)-L-homoserine lactone (8f)

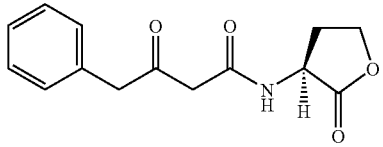

Figure 25:
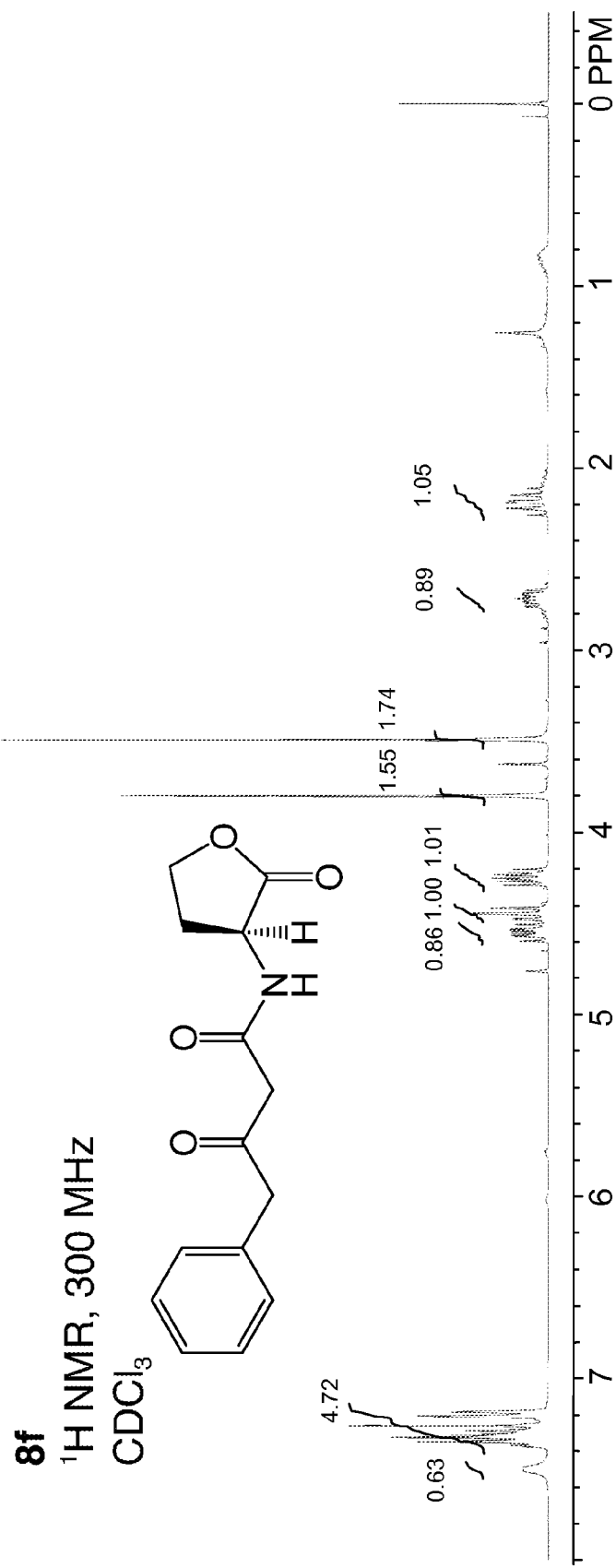
FIG. 25 shows an NMR spectrum for N-(3-oxo-4-phenylbutanoyl)-L-homoserine lactone (8f) produced by the scheme shown in FIG. 1A.

N-(3-oxo-4-phenylbutanoyl)-L-homoserine lactone (8f) was synthesized by the method described in EXAMPLE 9. FIG. 25 is the NMR spectrum (inset shows the chemical structure) where: $^1$H NMR (300 MHz, CDCl$_3$) δ=7.66 (s, 1H, NH), 7.64 (m, 3H, CH—Ar), 7.20 (d, 2H, CH—Ar), 4.60 (ddd, 1H, J=2.0 Hz, CH-lac), 4.47 (td, 1H, J=1.4 Hz, CH-lac), 4.28 (ddd, 1H, J=3.2 Hz, CH-lac), 3.80 (s, 2H, CH$_2$), 3.53 (s, 2H, CH$_2$), 2.70 (ddd, 1H, J=1.1 Hz, CH-lac), 2.23 (ddd, 1H, J=8.9 Hz, CH-lac); $^{13}$C NMR (75 MHz, CDCl$_3$) δ=204.0, 175.1, 167.0, 132.9, 129.8, 129.6, 129.2, 127.8, 66.2, 50.8, 49.3, 47.6, 15 29.7; MS(ESI): expected m/z=261, observed [M+Na]=284; [α$_D$]=+14.6 (c=3.4 mg/mL; CHCl$_3$); IR (cm$^{-1}$): 3335, 3054, 2916, 1176, 1772, 1663, 1538, 1179, 1022.

Example 35

N-(3-oxo-4-phenylbutanoyl)-D-homoserine lactone (8g)

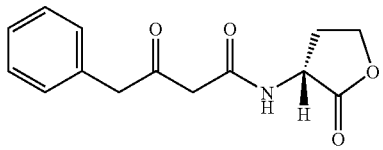

Figure 26:
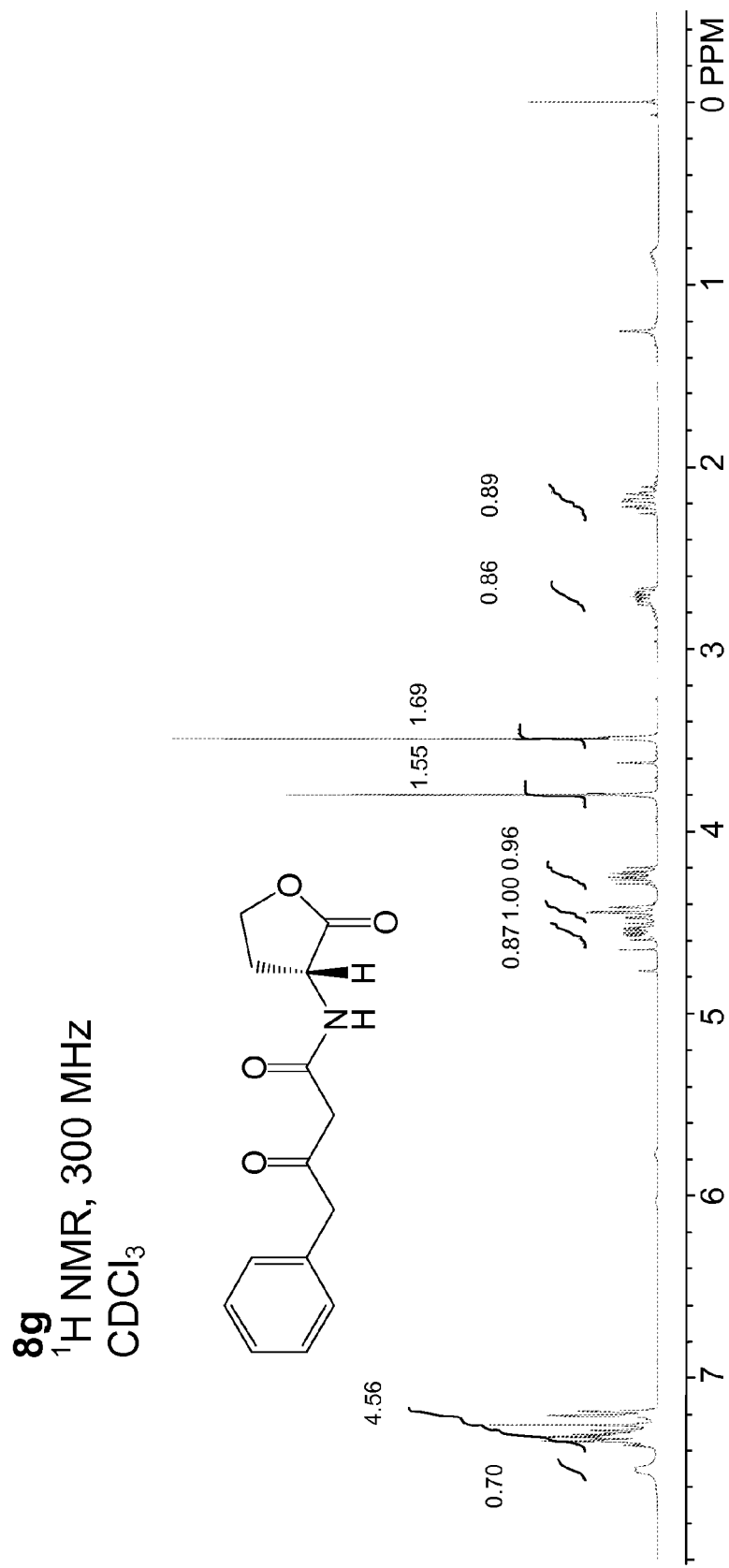
FIG. 26 shows an NMR spectrum for N-(3-oxo-4-phenylbutanoyl)-D-homoserine lactone (8g) produced by the scheme shown in FIG. 1A.

N-(3-oxo-4-phenylbutanoyl)-D-homoserine lactone (8g) was synthesized by the method described in EXAMPLE 9. FIG. 26 is NMR spectrum (inset shows the chemical structure) where: 1H NMR (300 MHz, CDCl$_3$) δ=7.70 (s, 1H, NH), 7.69 (m, 3H, CH—Ar), 7.21 (d, 2H, CH—Ar), 4.59 (ddd, 1H, J=2.0 Hz, CH-lac), 4.49 (td, 1H, J=1.2 Hz, CH-lac), 4.30 (ddd, 1H, J=2.1 Hz, CH-lac), 3.80 (s, 2H, CH$_2$), 3.53 (s, 2H, CH$_2$), 2.74 (ddd, 1H, J=1.0 Hz, CH-lac), 2.23 (ddd, 1H, J=9.0 Hz, CH-lac); $^{13}$C NMR (75 MHz, CDCl$_3$) δ=204.1, 174.9, 167.1, 132.7, 129.7, 129.6, 129.2, 128.8, 127.8, 66.2, 50.9, 49.4, 47.3, 29.8; MS(ESI): expected m/z=261, observed [M+Na]=284; [α$_D$]=−6.2 (c=1.5 mg/mL; CHCl$_3$); IR (cm$^{-1}$): 3335, 3054, 2916, 1176, 1772, 1663, 1538, 1179, 1022.

Example 36

N-(3-oxo-octanoyl)-D-homoserine lactone (8h)

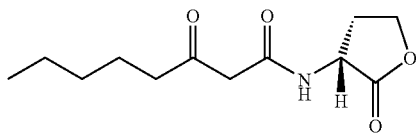

Figure 27:
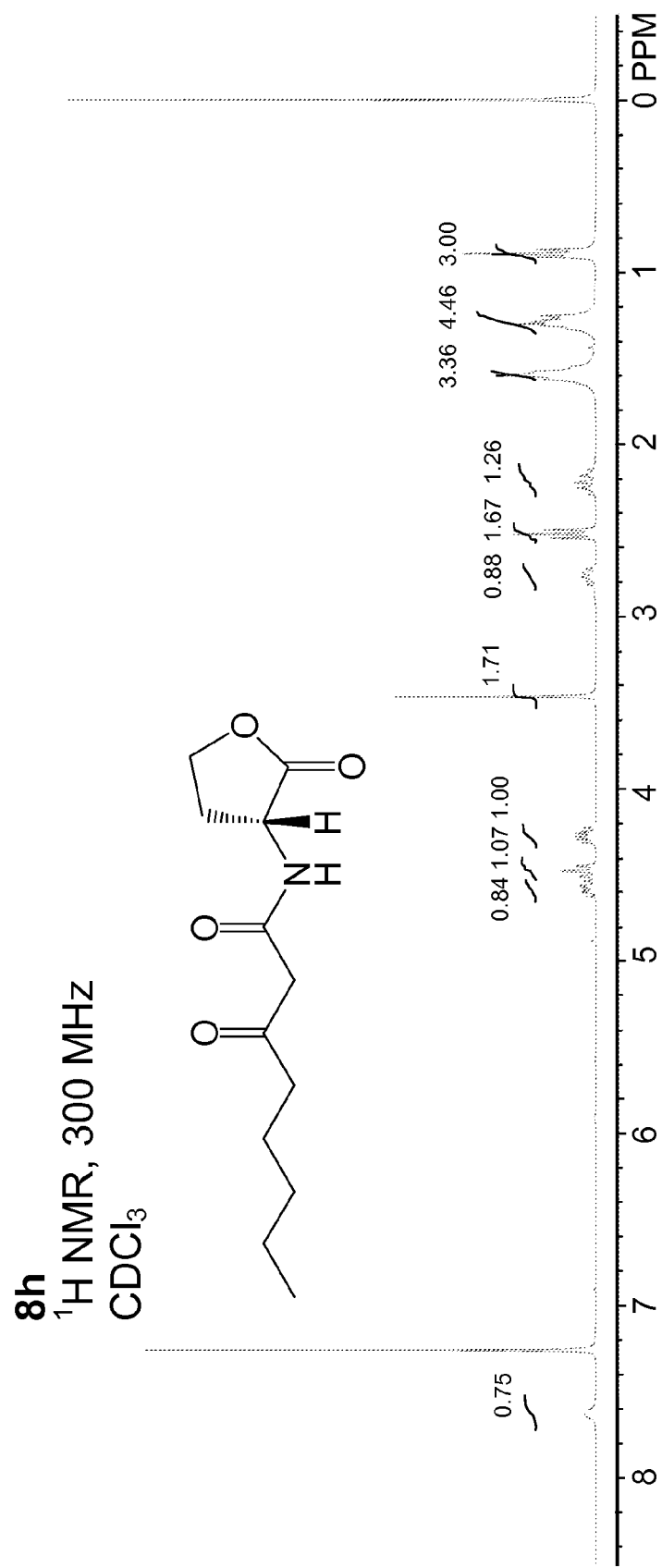
FIG. 27 shows an NMR spectrum for N-(3-oxo-octanoyl)-D-homoserine lactone (8h) produced by the scheme shown in FIG. 1A.

N-(3-oxo-octanoyl)-D-homoserine lactone (8h) was synthesized by the method described in Example 9. FIG. 27 shows the NMR spectrum (inset shows the chemical structure) where: $^1$H NMR (300 MHz, CDCl$_3$) δ=7.95 (s, 1H, NH), 4.67 (ddd, 1H, J=6.7 Hz, CH-lac), 4.53 (td, 1H, J=1.3 Hz, CH-lac), 4.34 (ddd, 1H, J=6.1 Hz, CH-lac), 3.52 (s, 2H, CH$_2$), 2.81 (dddd, 1H, J=1.2 Hz, CH-lac), 2.57 (t, 2H, J=7.2 Hz, CH$_2$) 2.34 (ddd, 1H, J=2.4 Hz, CH-lac), 1.64 (p, 2H, J=7.2 Hz, CH$_2$), 1.43 (m, 4H, J=6.4 Hz, (CH$_2$)$_4$), 0.91 (t, 3H, J=6.5 Hz, CH$_3$); $^{13}$C NMR (75 MHz, CDCl$_3$) δ=206.7, 175.0, 166.7, 66.3, 66.1, 49.3, 48.4, 44.0, 31.3, 30.0, 23.2, 22.6, 14.1; MS(ESI): expected m/z=241, observed [M+Na]=264; [α$_D$]=−19.6 (c=2.7 mg/mL; CHCl$_3$); IR (cm$^{-1}$): 3684, 3020, 2401, 1783, 1712, 1674, 1527, 1216.

Example 37

Evaluation of AHL Mosher Amides

Figure 28A:
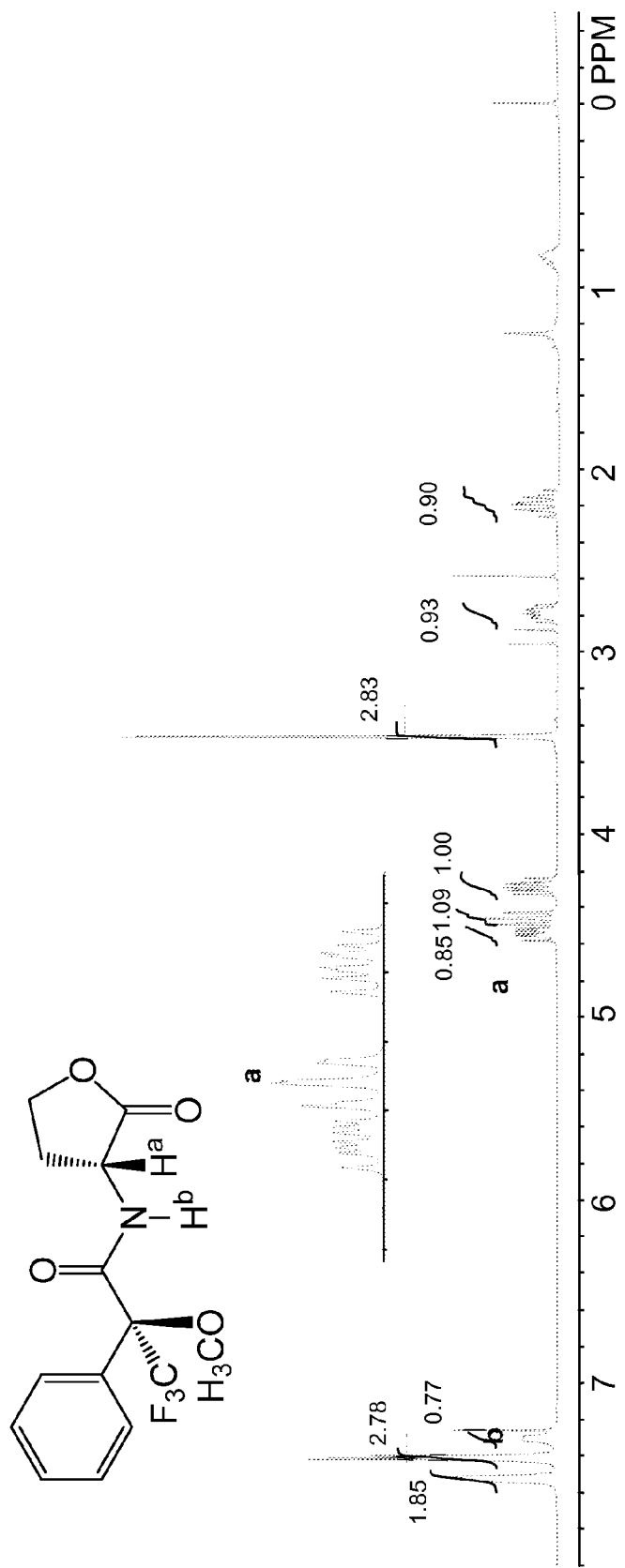
FIGS. 28A-B show an NMR spectrum for R-Mosher amide AHL derivatives (300 MHz, CDCl$_3$) produced by the scheme shown in FIG. 1A.
Figure 28B:
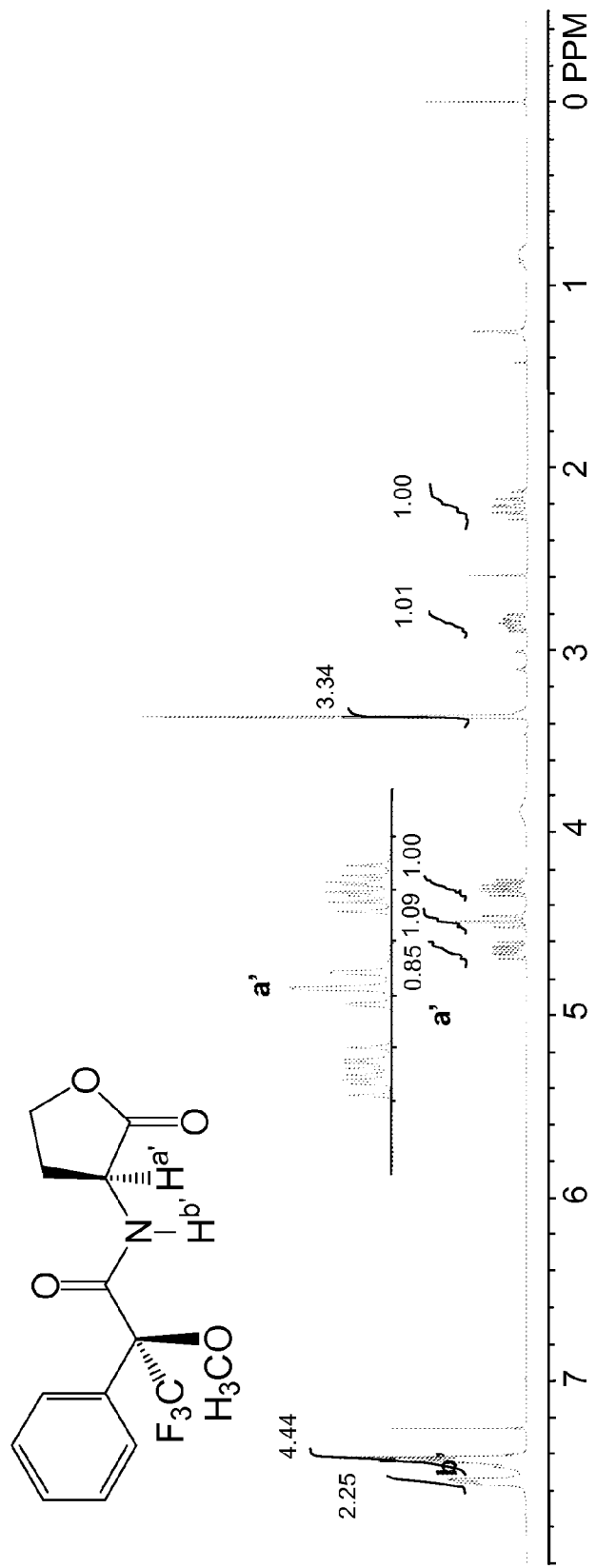

The enantiopurity of the AHLs synthesized via SCHEME I was assessed through the characterization of AHL Mosher amide derivatives. This solid-phase route was used to synthesize R-Mosher amide diastereomers starting from both the L- and D-methionine loaded resins (3). Analysis of the $^1$H NMR (300 MHz, CDCl$_3$) spectrum of the diastereomers indicated that the AHL de was >95% (as calculated from 100(a-a') or 100(b-b') where a, a', b, b' are the fractional yields based on the integration of respective peaks in the NMR spectrum). FIGS. 28A and 28B show the $^1$H NMR spectrum of the D and L homoserine enantiomers, respectively.

Biological Screenings

Compound Handling & Reagents: Stock solutions of synthetic compounds (10 mM and 100 mM) were prepared in either ethyl acetate or CHCl$_3$ and stored at −20° C. in sealed vials. The solutions were allowed to come to room temperature prior to use in assays. Solvent resistant polypropylene (Corning Costar cat. no. 3790) or polystyrene (Corning Costar cat. no. 3997) 96-well plates were used when appropriate.

All biological reagents were purchased from Fisher and used according to enclosed instructions. AB Minimal media was prepared containing 1.0 g/L NH$_4$Cl, 0.3 g/L MgSO$_4$.7H$_2$O, 0.15 g/L KCl, 0.01 g/L CaCl$_2$, 2.5 mg/L FeSO$_4$.7H$_2$O, 5.0 g/L glucose, 1.0 g/L NaH$_2$PO$_4$, and 3.0 g/L K$_2$HPO$_4$, pH=6.8. M9 media used in biofilm assays was prepared as described (De Kievit, T. R.; Gillis, R.; Marx, S.; Brown, C.; Iglewski, B. H. *Appl. Environ. Microbiol.* 2001, 67, 1865-1873). Buffers and solutions for Miller absorbance assays were prepared as described (Miller, J. H. *Experiments in Molecular Genetics*; Cold Spring, 1972).

Control Compounds: Compounds 7g (Zhu, J.; Beaber, J. W.; More, M. I.; Fuqua, C.; Eberhard, A.; Winans, S. C. *J. Bacteria* 1998, 180, 5398-5405) and 8h (Reverchon, S.; Chantegrel, B.; Deshayes, C.; Doutheau, A.; Cotte-Pattat, N. *Bioorg. Med. Chem. Lett.* 2002, 12, 1153-1157) were prepared according to the solid-phase methods described above. Compound 9 was synthesized using a modified solution-phase procedure (Smith, K. M.; Bu, Y.; Suga, H. *Chem. Biol.* 2003, 10, 563-571) as follows: β-keto acid 5d (483 mg, 1.87 mmol) and 2-aminophenol (204 mg, 1.87 mmol) were dissolved in 10 mL DMF, after which 1-(3-dimethylaminopropyl)-3-ethylcarbodiimide hydrochloride (EDC, 456 mg, 2.38 mmol), 4-dimethylaminopyridine (DMAP, 228 mg, 1.87 mmol), and N,N-diisopropylethylamine (DIPEA, 500 μL, 2.87 mmol) were added. The reaction mixture was stirred at room temperature until TLC indicated completion (12 h). The reaction mixture was diluted with 30 mL of diethyl ether and washed 2× with 30 mL 10% citric acid, 2×30 mL saturated NaHCO$_3$, and 1×15 mL saturated NaCl. The ether layer was separated, dried with magnesium sulfate, and the solvent removed in vacuo. The resulting solid was immediately subjected to 95% TFA/H$_2$O (30 minutes) to affect ketal deprotection. Extraction of the reaction mixture (3×15 mL) with CHCl$_3$, drying over MgSO$_4$, and removal of CHCl$_3$ in vacuo gave a yellow-brown solid. Purification by flash silica gel chromatography (1:1 EtOAc/hexane) yielded 9 as a white solid. 228 mg, 40% overall yield. Compounds 7g, 8h, and 9 were stored at −20° C. until required for use.

Instrumentation: Absorbance and fluorescence assay results were obtained using a PerkinElmer Wallac 2100 EnVision™ (PerkinElmer, Wellsley, Mass.) multilabel plate reader using Wallac Manager v1.03 software. A filter of 600 nm was used for reading bacterial cell density. Filters of 420 nm and 550 nm were used for Miller-type absorbance assays (Griffith, K. L.; Wolf, R. E., Jr. *Biochem. Biophys. Res. Commun.* 2002, 290, 397-402). Filters of 485 nm for excitation and 535 nm for emission were used for evaluating the production of green fluorescent protein (GFP) in fluorescence assays. Biofilms were visualized with a Bio-Rad MRC-1024 laser scanning confocal microscope using Lasersharp v3.2 software. Biofilm visualization data was manipulated using Confocal Assistant v4.02 software (Available to the public from nephrology.iupui.edu/imaging/software.htm).

Example 38

Screening of Synthetic AHL Library

The AHL library constructed by the schema described above, was screened in two bacterial reporter strains for antagonism of quorum sensing: 1) *P. aeruginosa* PAO-JP2 (plasI-LVAgfp), (De Kievit, T. R.; Gillis, R.; Marx, S.; Brown, C.; Iglewski, B. H. *Appl. Environ. Microbiol.* 2001, 67, 1865-1873) and 2) *A. tumefaciens* WCF47 (pCF372). Examination of these two strains was valuable for two reasons: 1) the direct clinical relevance of *P. aeruginosa*, and 2), the extensive body of biochemical and structural data for TraR in *A. tumefaciens*. Both of these reporter strains lack their native AHL synthases, yet retain active LuxR-type receptors (LasR and TraR proteins, respectively); exogenous ligand is required for receptor activation, which can be measured by fluorescence (green fluorescent protein (GFP) for LasR) or absorbance (via β-galactosidase activity for TraR) measurements.

Figure 29:
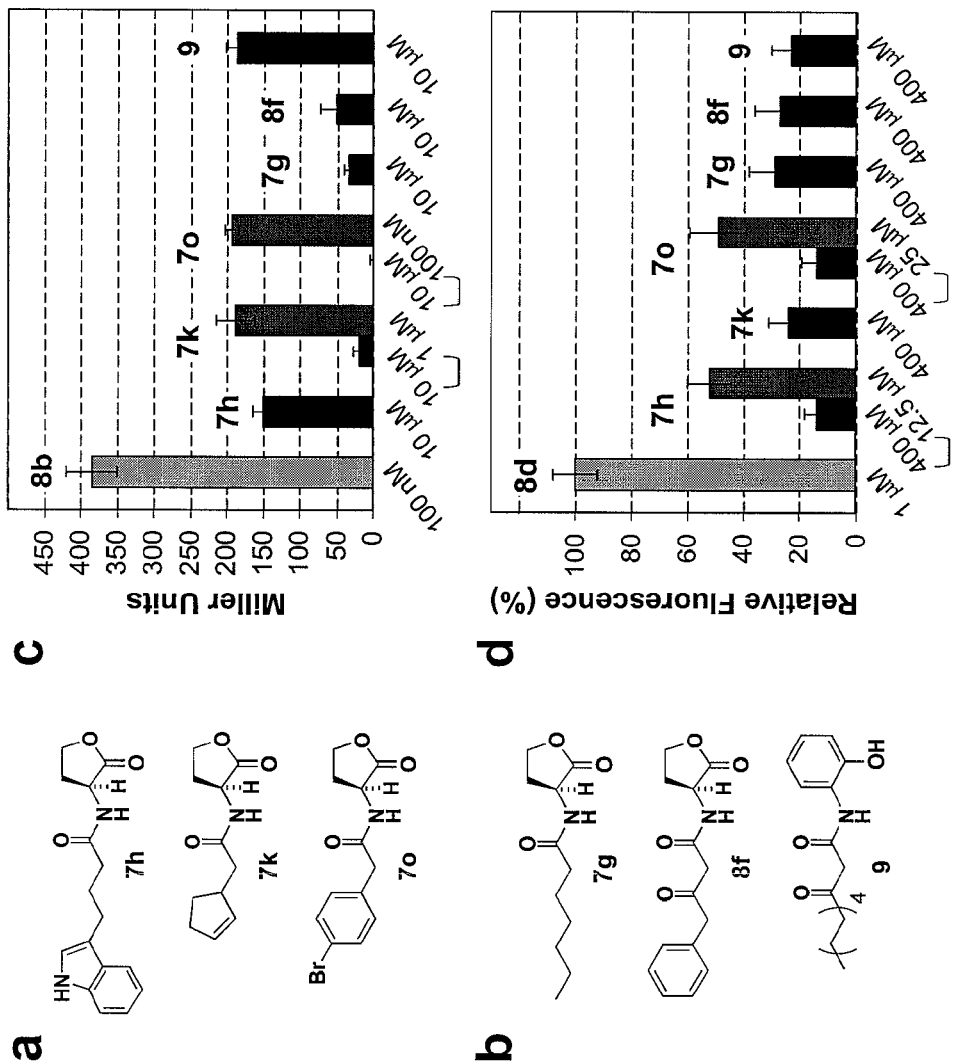
FIGS. 29A-29D show the results of antagonism screens for (FIG. 29A) quorum sensing antagonists identified by the methods of the present invention and (FIG. 29B) known quorum sensing antagonists and quorum sensing antagonism activity of both sets of compounds in (FIG. 29C) *A. tumefaciens* and (FIG. 29D) *P. aeruginosa* reporter strains.

The antagonism screens revealed a suite of new quorum sensing inhibitors. In these experiments, illustrated in FIG. 29, the strains were treated with non-native AHL in the presence of native AHL ligand (8b or 8d), and a reduction in absorbance or fluorescence signal indicated that the non-native AHL was able to antagonize LuxR-type protein activity. Three compounds (7h, 7k and 7o) showed significant activity against TraR in *A. tumefaciens* and were one to two orders of magnitude more active than the previously reported LuxR-type protein antagonists examined as controls (7g, 8f, and 9 at 10 µM in FIGS. 29a & 29c). Impressively, bromophenyl AHL 7o displayed 50% inhibition at an equimolar concentration of 8b (100 nM). Interestingly, the same three ligands were also identified as antagonists against LasR in *P. aeruginosa* (FIG. 29d). Here indol AHL 7h and bromo-phenyl AHL 7o were twice as active as the three controls (at 400 µM), with indol AHL 7h displaying 50% inhibition at a 12.5:1 ratio with native ligand 8d. Notably, all three ligands contain bulky, hydrophobic acyl groups. This structural similarity, coupled with their cross activity, suggests that the ligands could be interacting with the TraR and LasR receptors in analogous manners; efforts to characterize these interactions are currently underway.

Further, the cross reactivity of ligands 7h, 7k and 7o illustrated that methods illustrated to construct the AHL combinatorial library are sufficient to create synthetic ligands for use in screening all bacteria having AHL-like ligand-receptors. Further, characterization of the synthetic ligands was made using reporter gene assays to determine agonism/antagonism effects of the non-natural ligands compared to naturally occurring ligands.

Investigation of Agonism/Antagonism Effects

Figure 30:
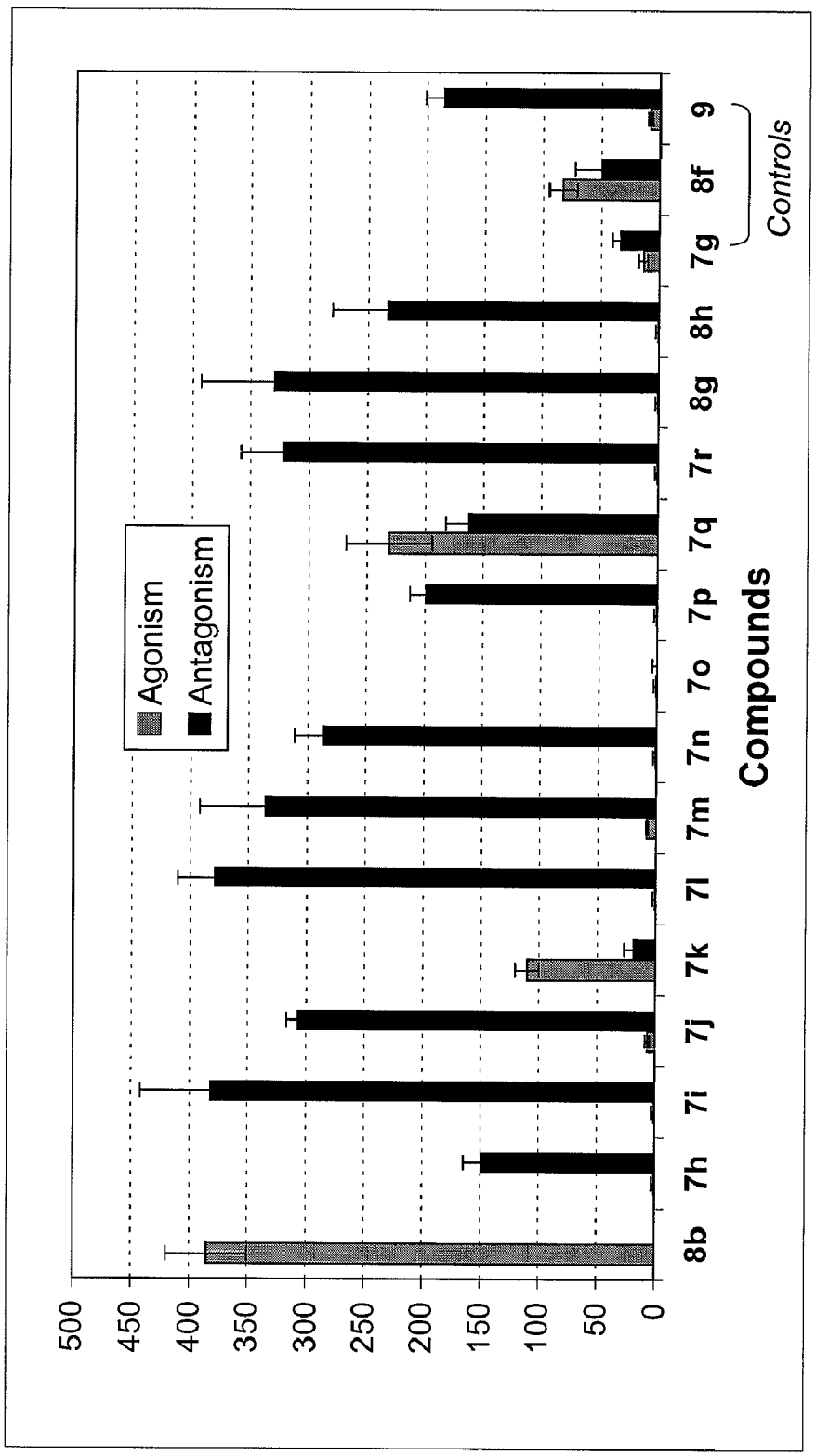
FIG. 30 is a graphical display of the results of *A. tumefaciens* reporter gene screening using AHL derivatives 7h-7r and 8f-8h.
Figure 31A:
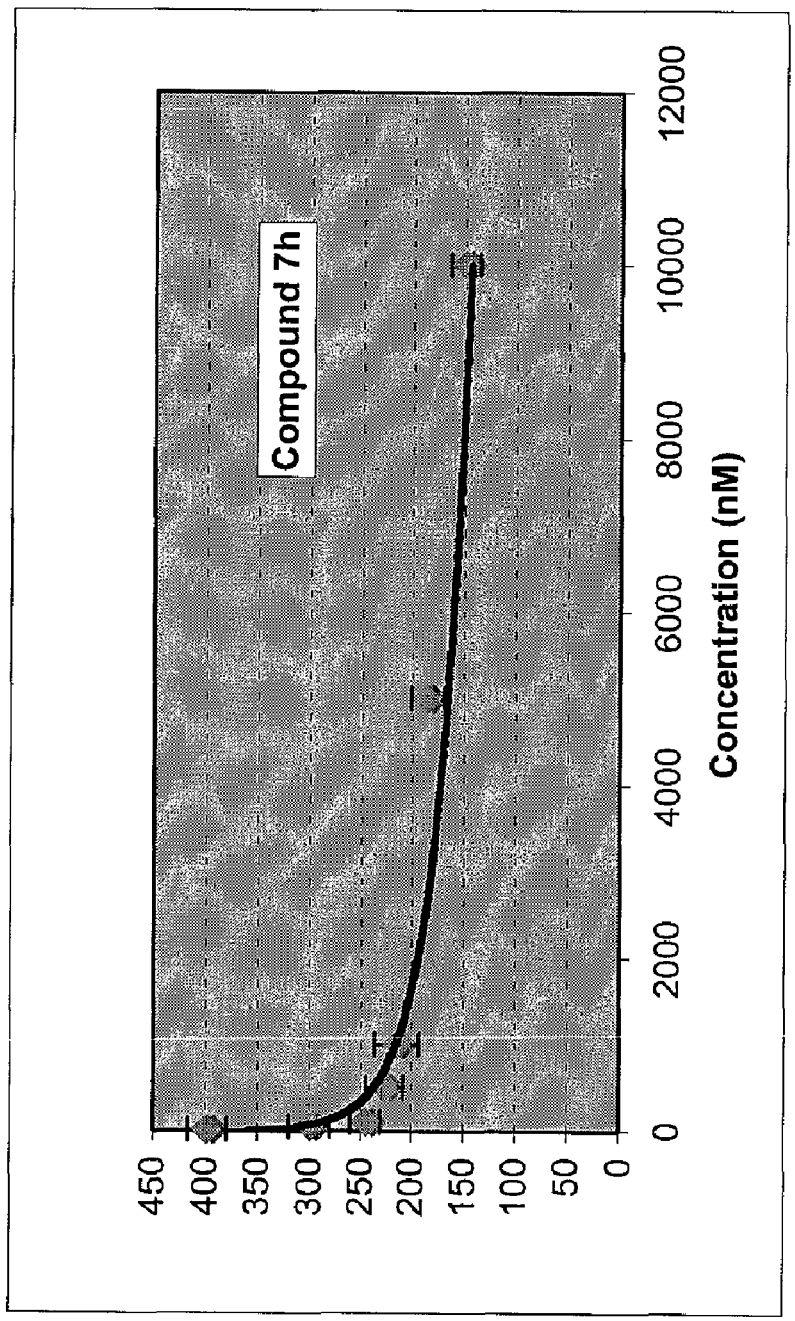
FIGS. 31A-31F are graphical displays of the results of dose response antagonism screening data for AHL derivatives 7h (FIG. 31A), 7k (FIG. 31B) and 7o (FIG. 31C) and control compounds 7g (FIG. 31D), 8f (FIG. 31E) and 9 (FIG. 31F) in an *A. tumefaciens* reporter strain. Reporter strain: WCF47 (pCF372). Miller units report relative beta-galactosidase activity with ONPG as colometric substrate. Compounds screened at various concentrations against 100 nM native ligand 8b (OOHL). Error bars are ±one S.E.M., calculated from at least three replicate screens.
Figure 31B:
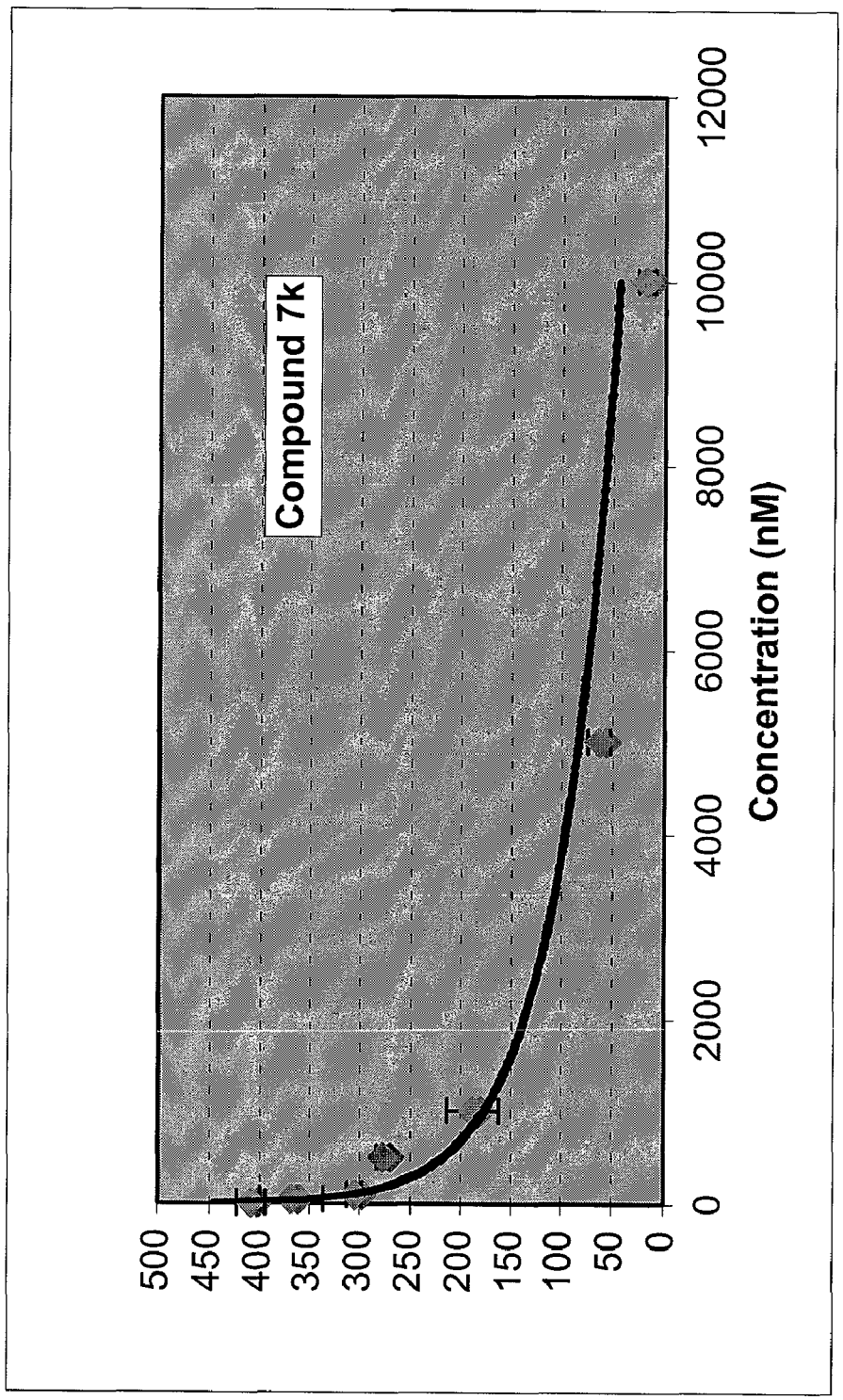
Figure 31C:
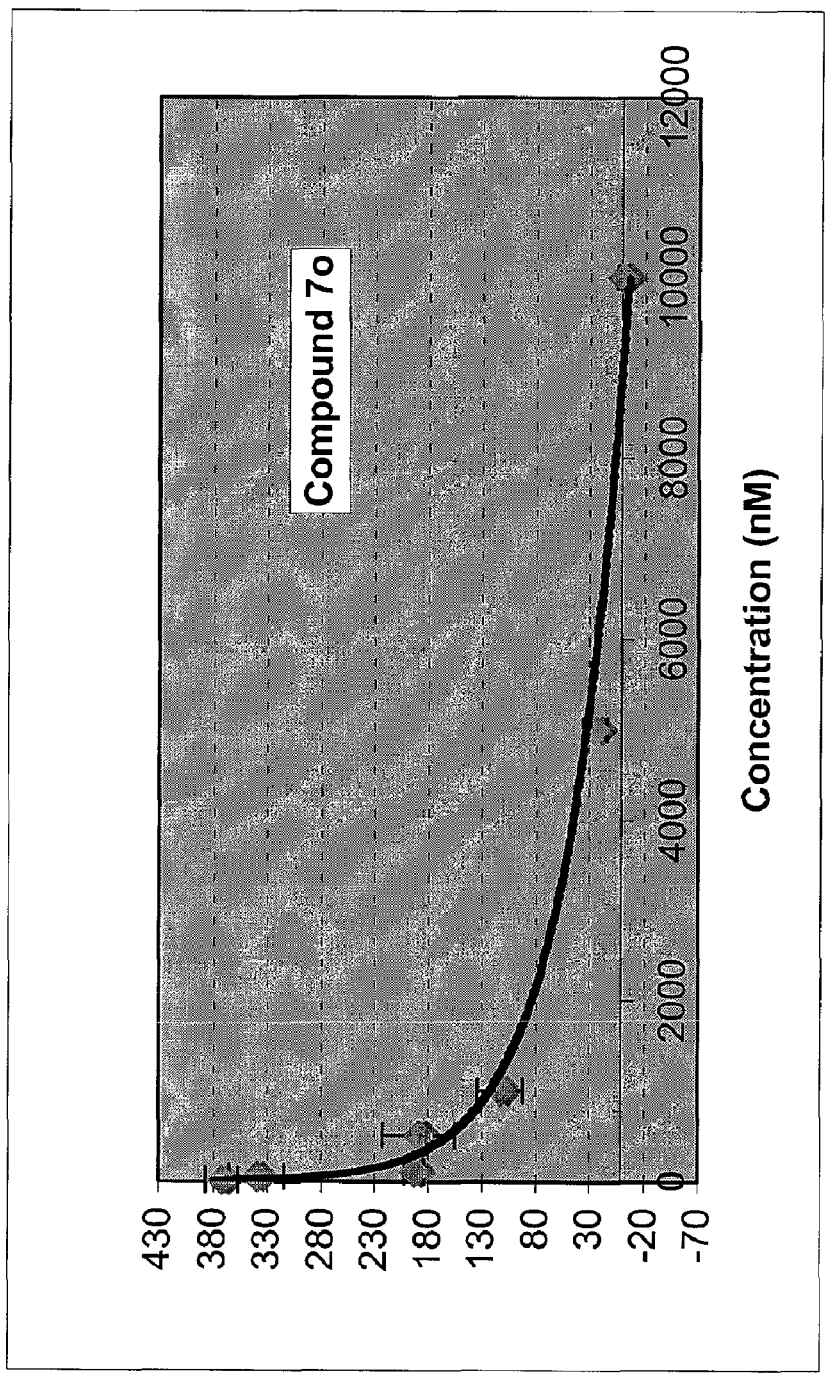
Figure 31D:
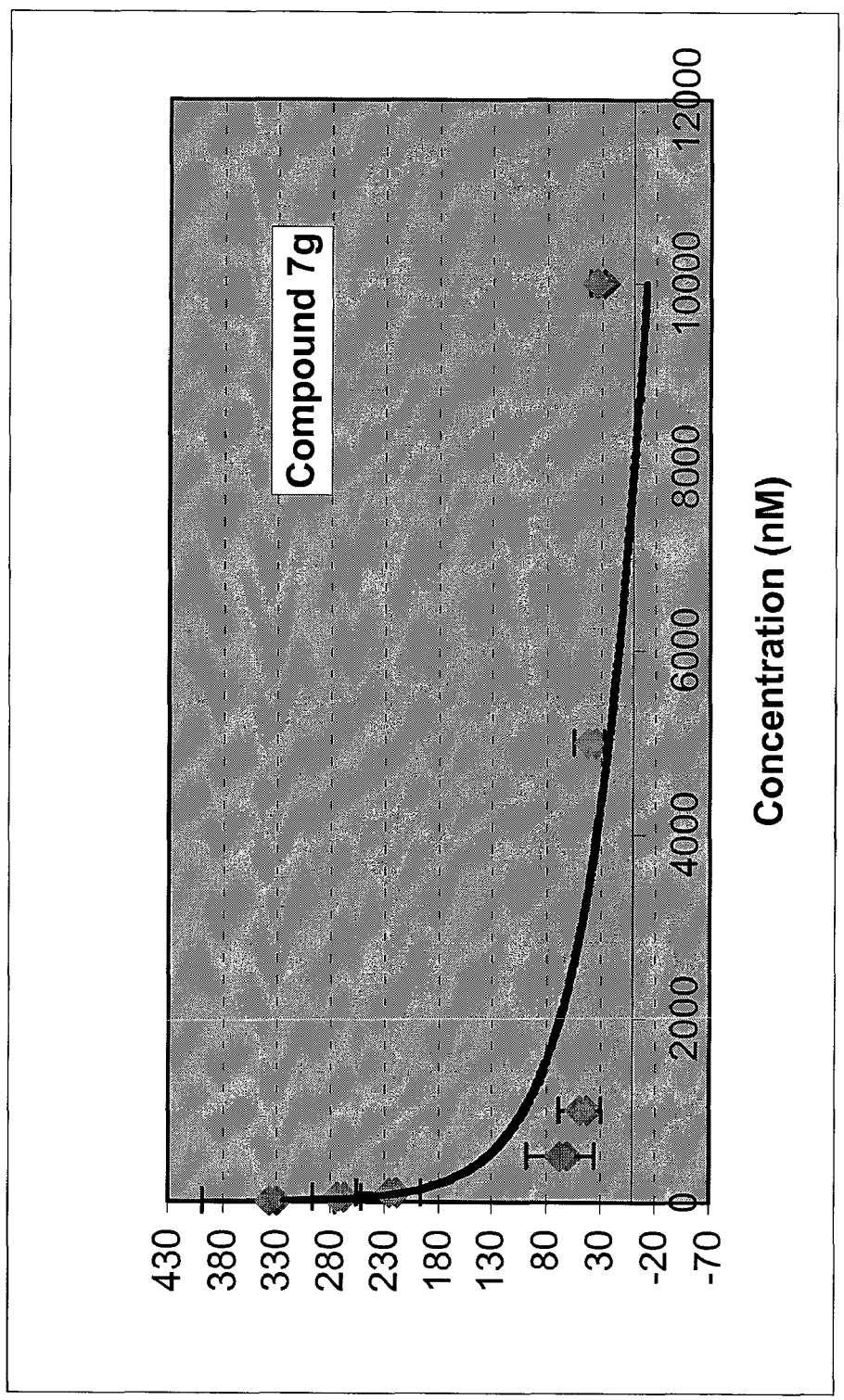
Figure 31E:
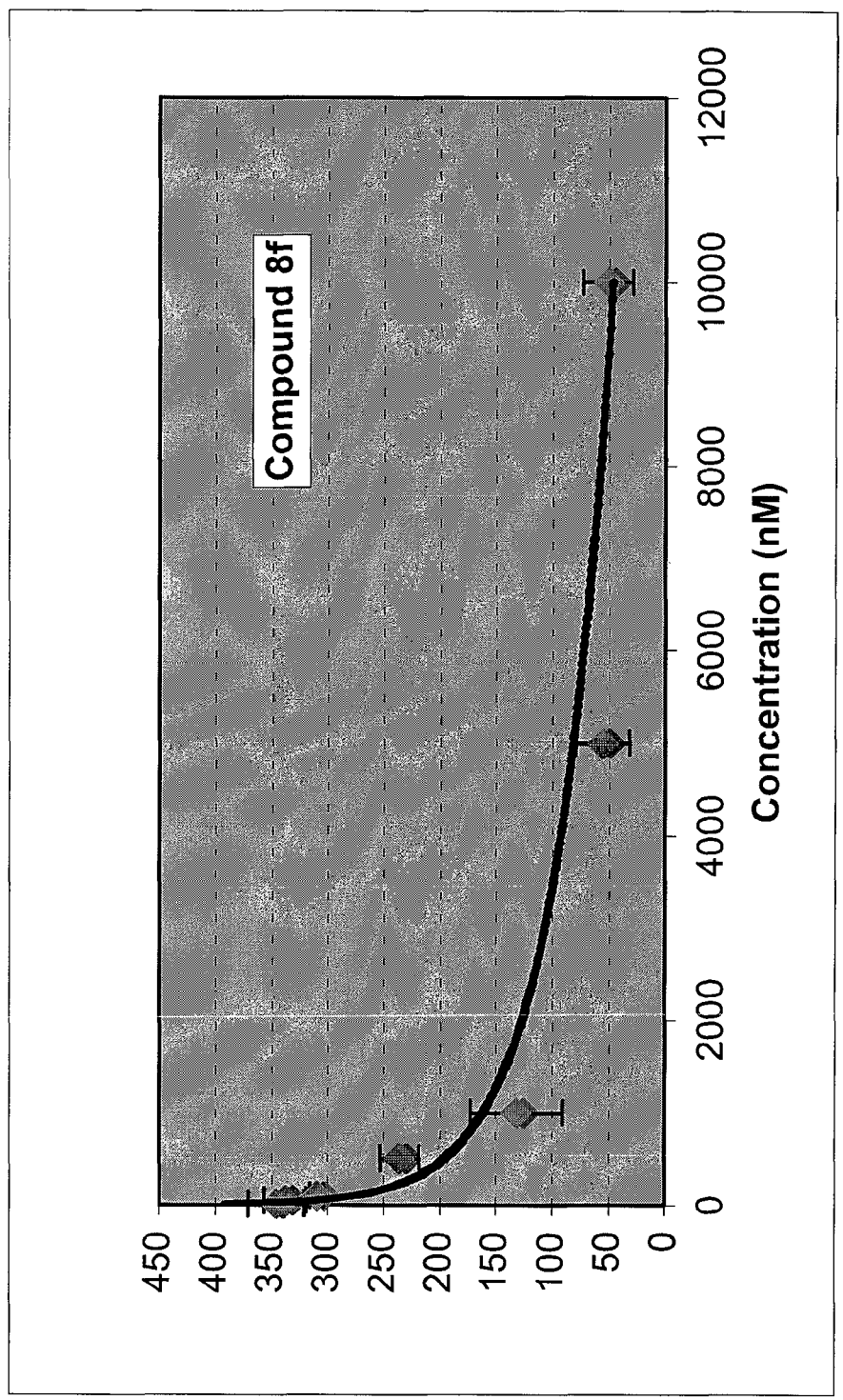
Figure 31F:
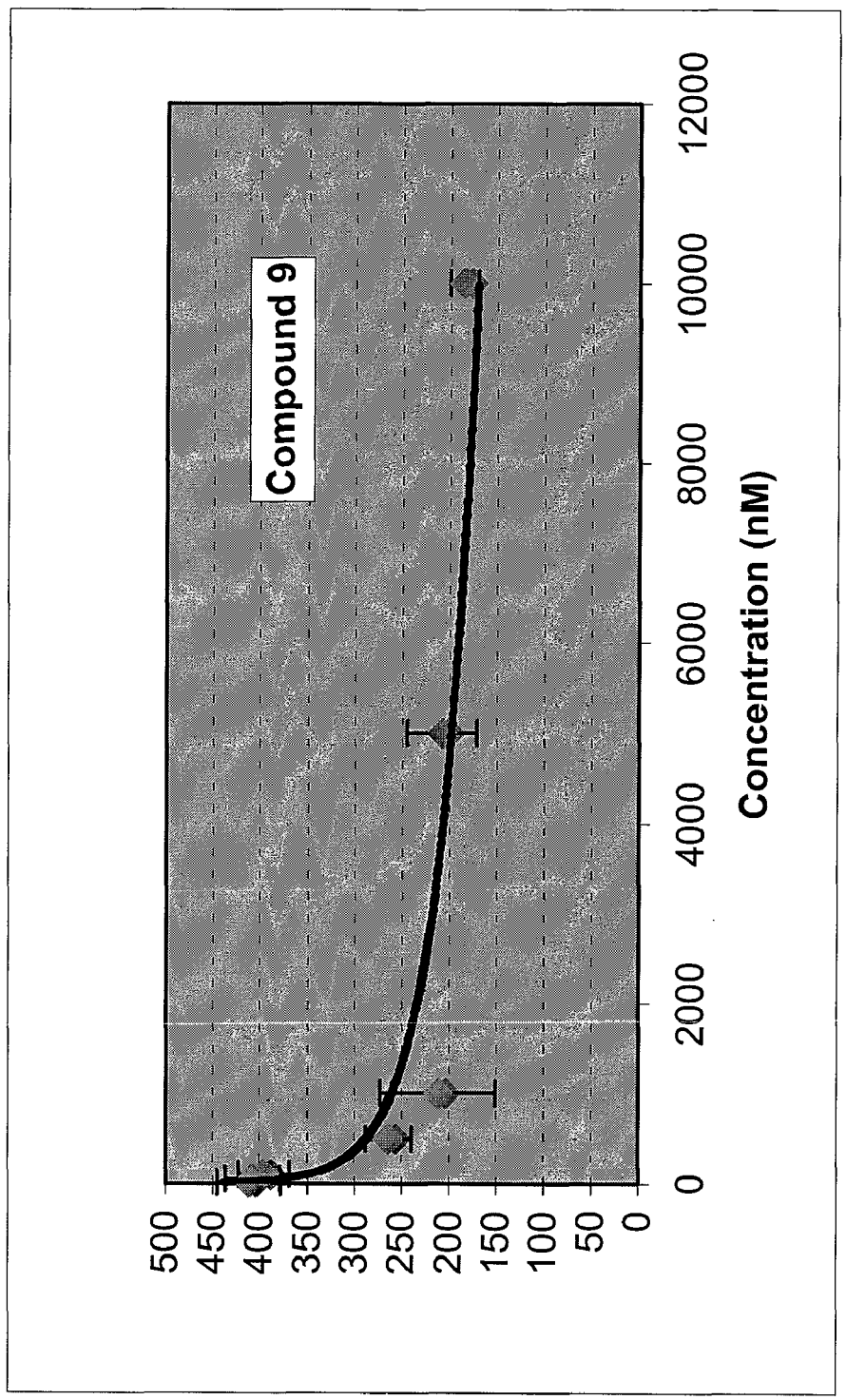
Figure 32:
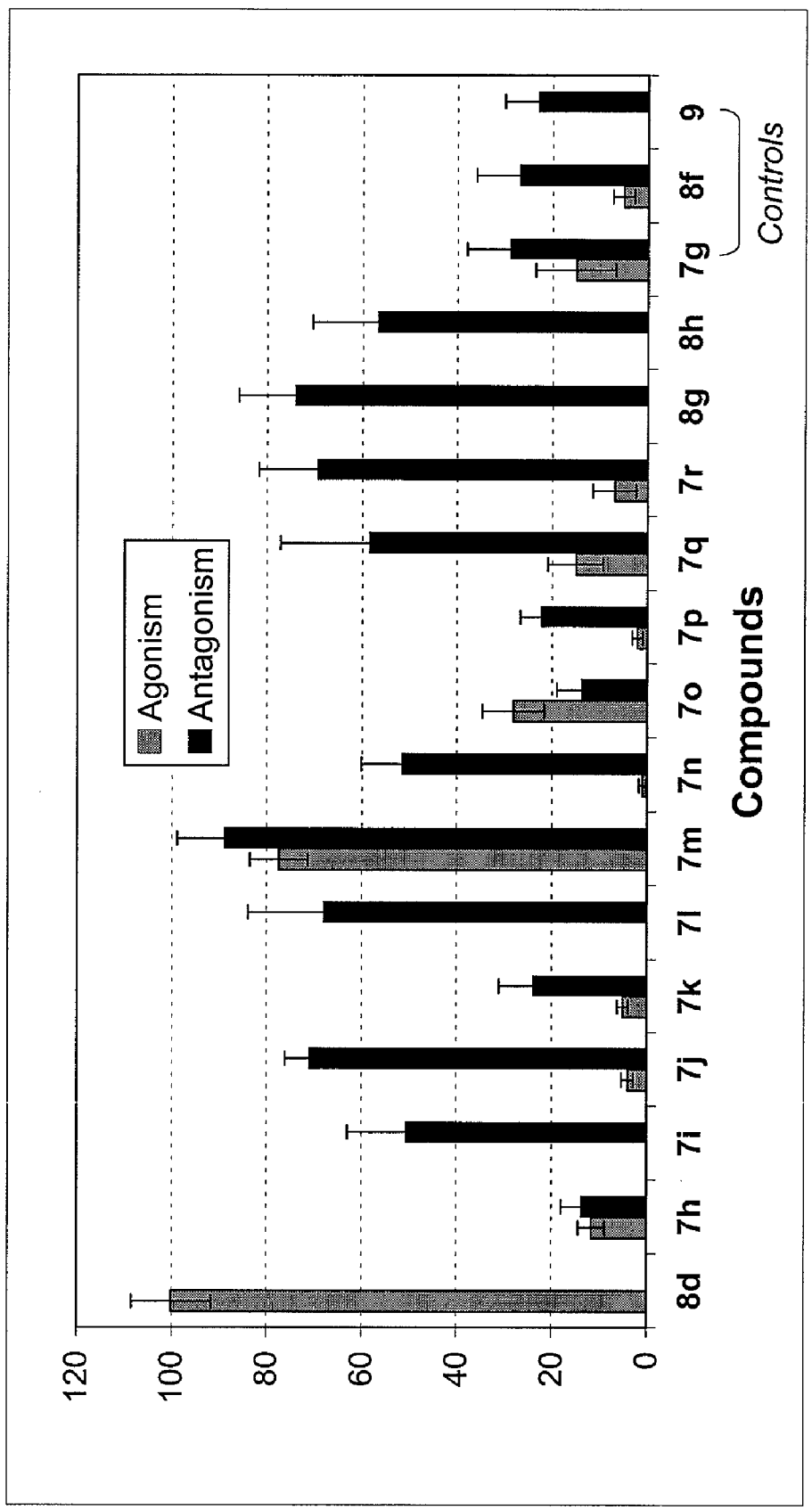
FIG. 32 is a graphical display of the results of *P. aeruginosa* reporter gene screening using AHL derivatives 7h-7r and 8f-8h.
Figure 33A:
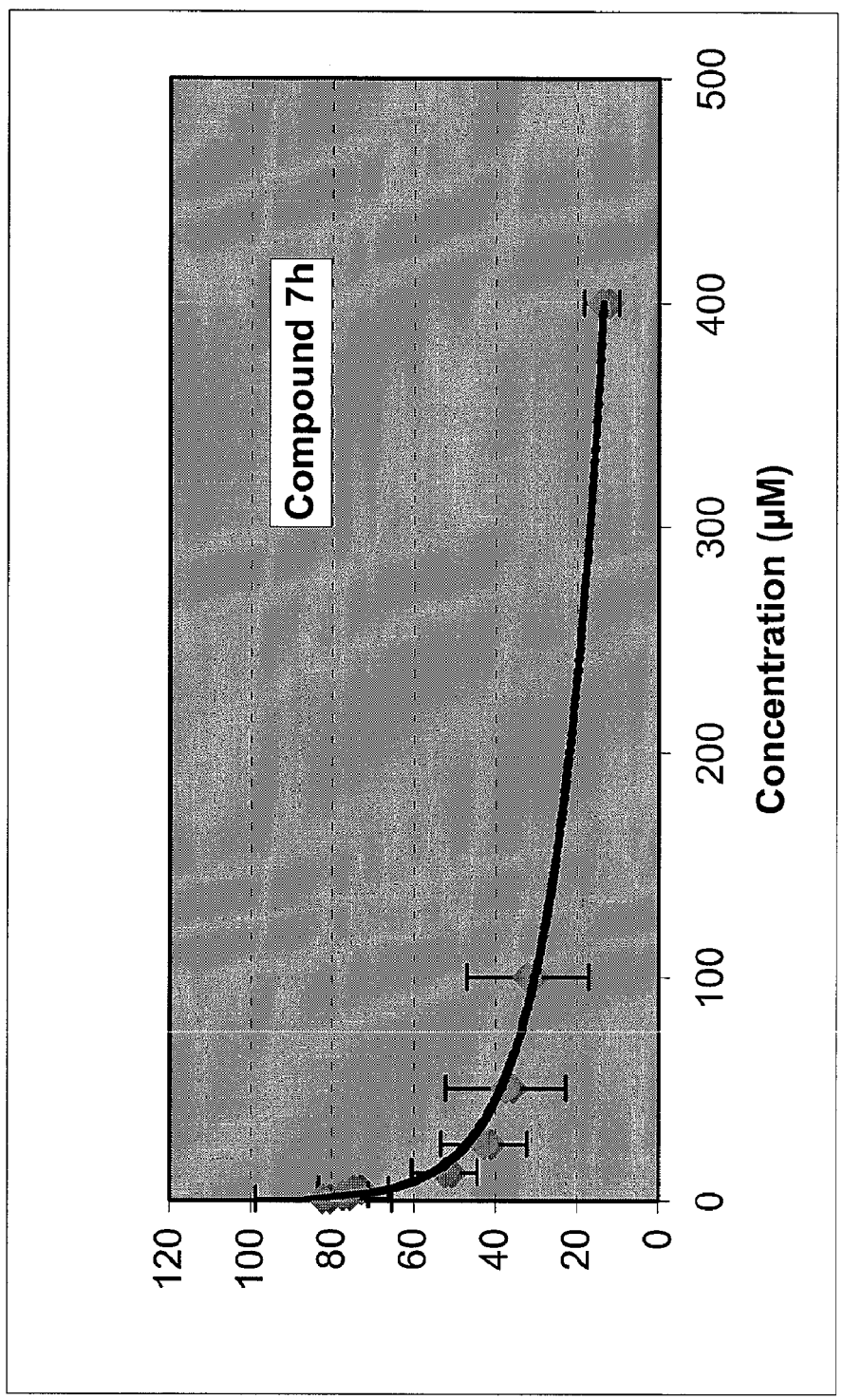
FIGS. 33A-33F are graphical displays of the results of dose response antagonism screening data for AHL derivatives 7h (FIG. 33A), 7k (FIG. 33B) and 7o (FIG. 33C) and control compounds 7g (FIG. 33D), 8f (FIG. 33E) and 9 (FIG. 33F) in a *P. aeruginosa* reporter strain. Reporter strain: PAO-JP2 (plasI-LVAgfp). Fluorescence reported as percentage relative to native ligand 8d (ODHL). Compounds screened at various concentrations against 1 µM native ligand 8d (ODHL). Error bars are ±one S.E.M., calculated from at least three replicate screens.
Figure 33B:
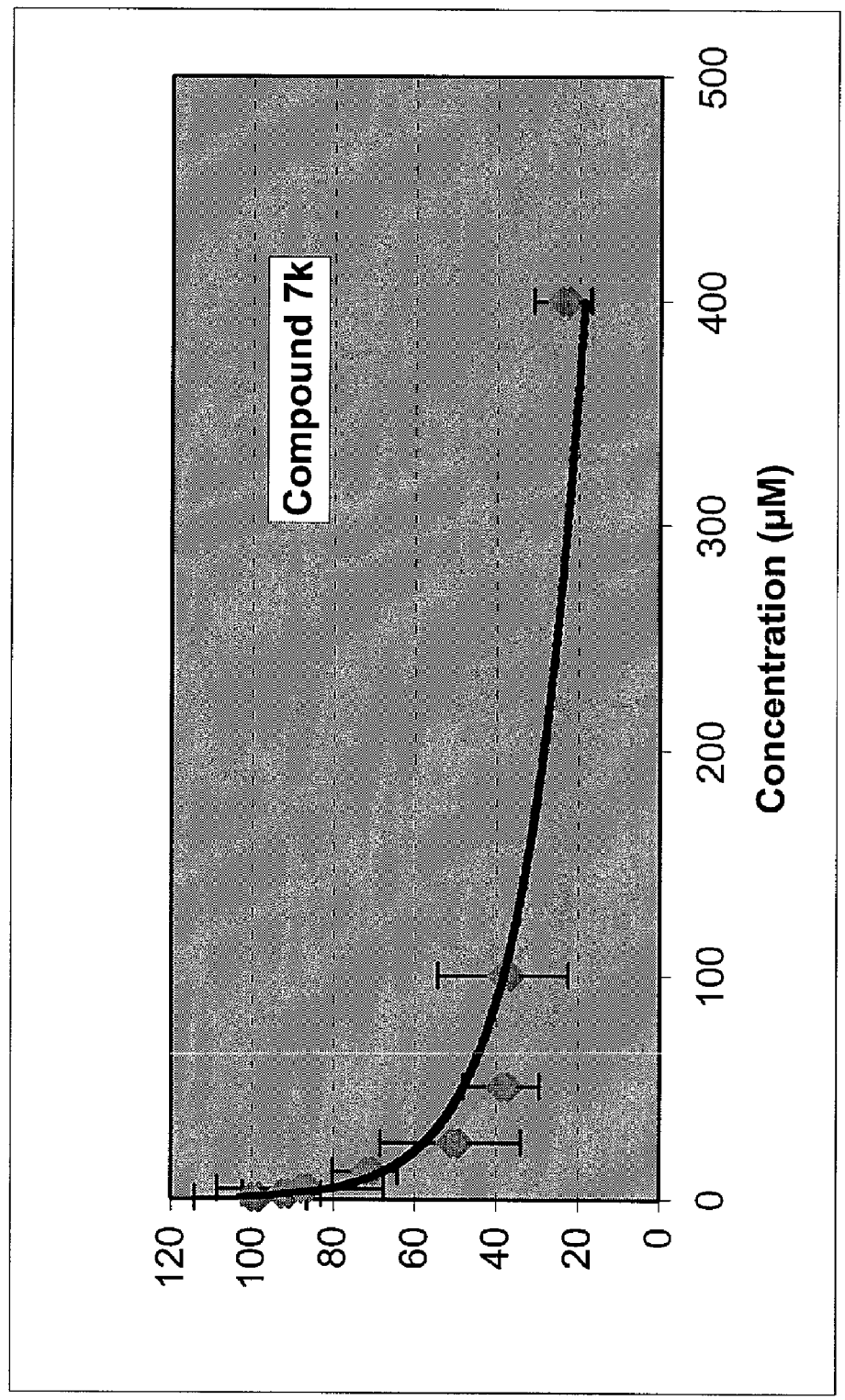
Figure 33C:
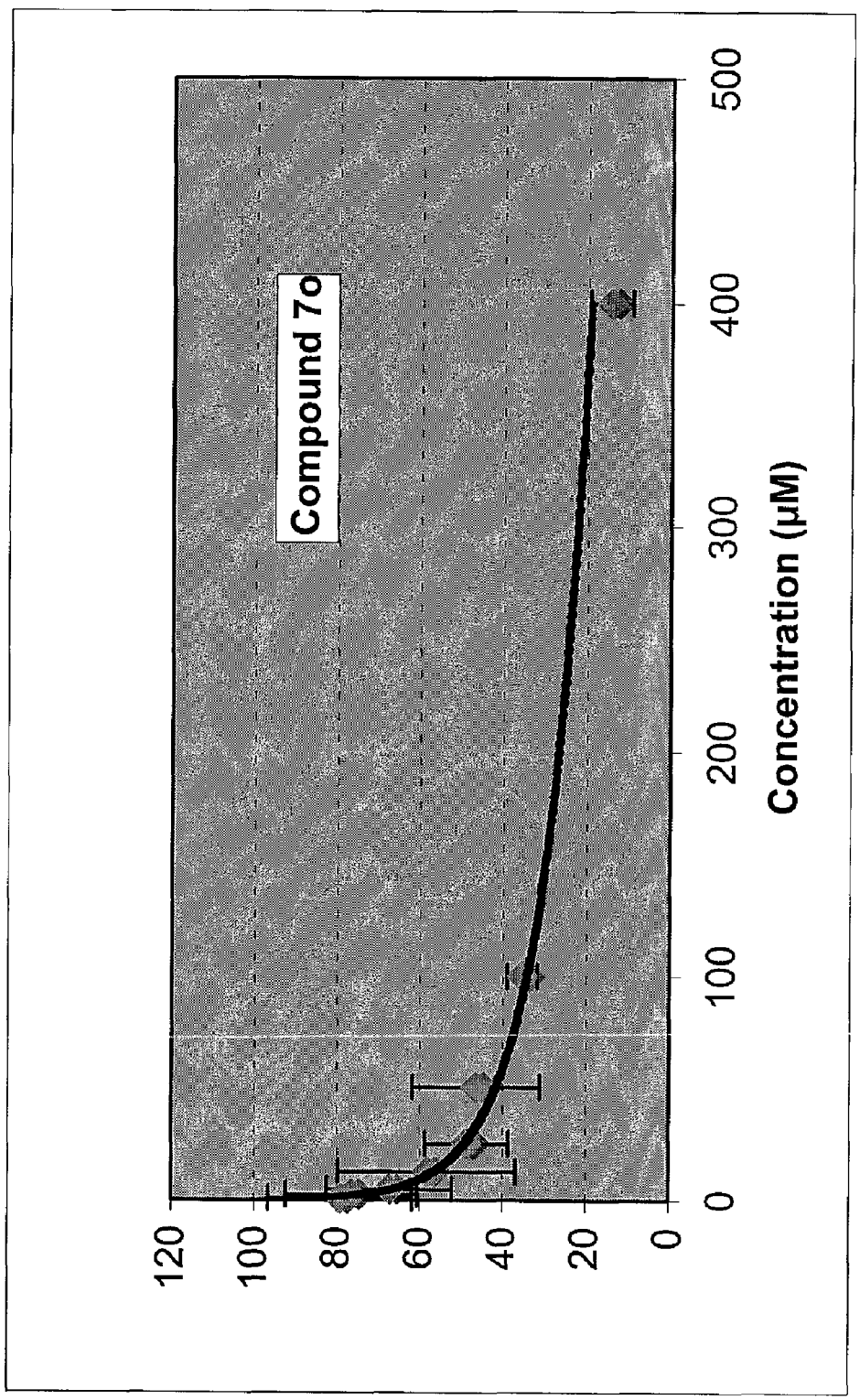
Figure 33D:
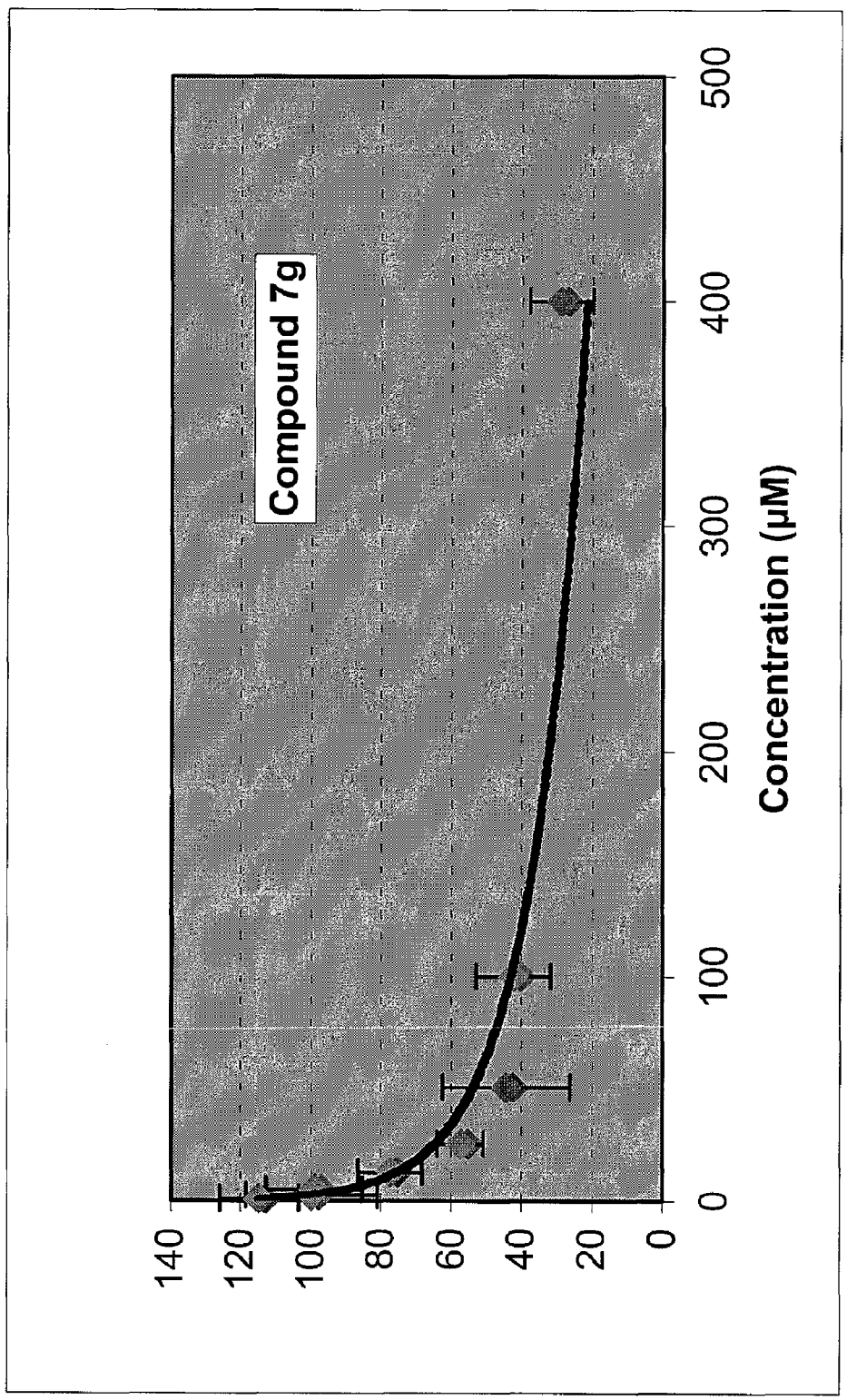
Figure 33E:
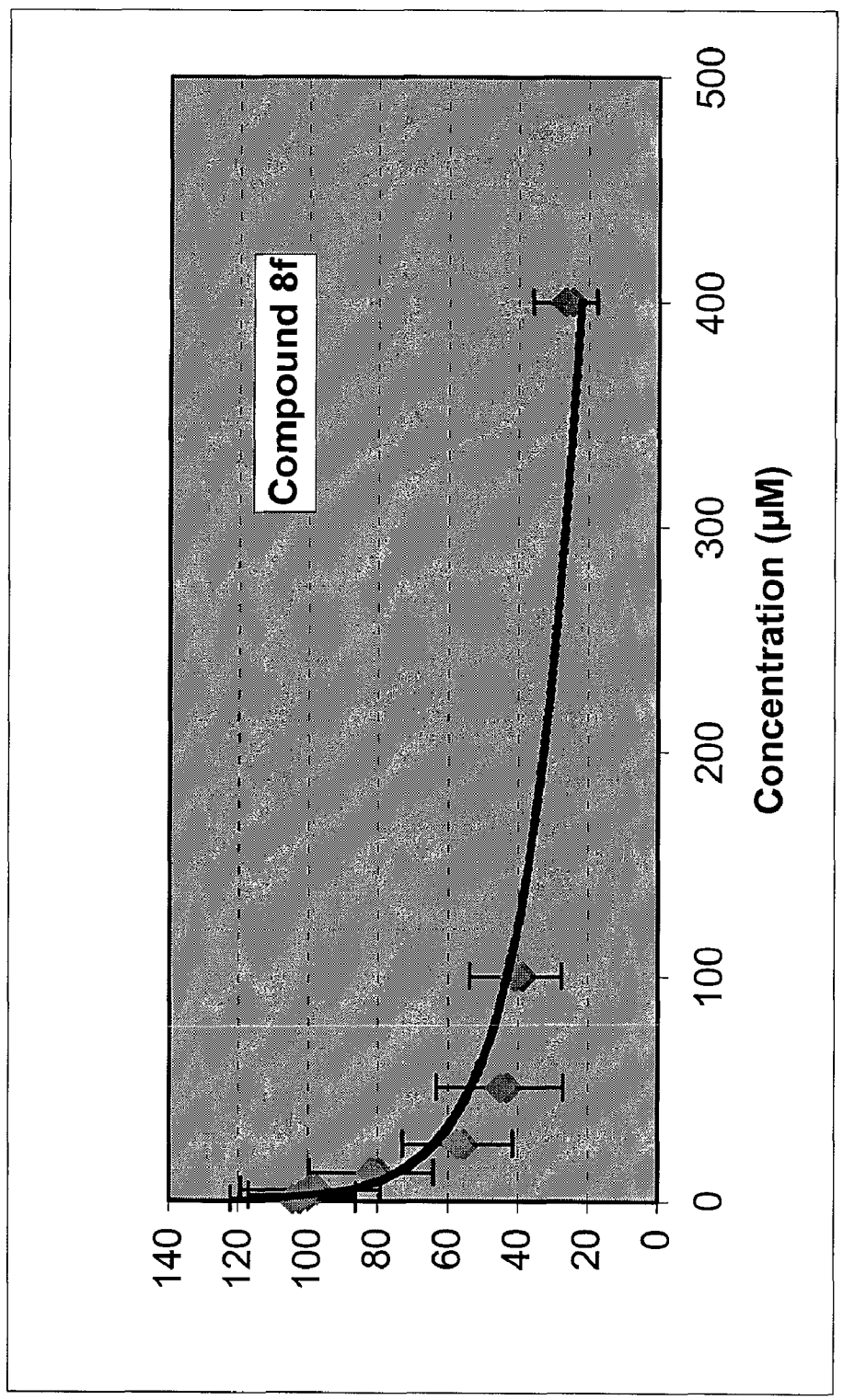
Figure 33F:
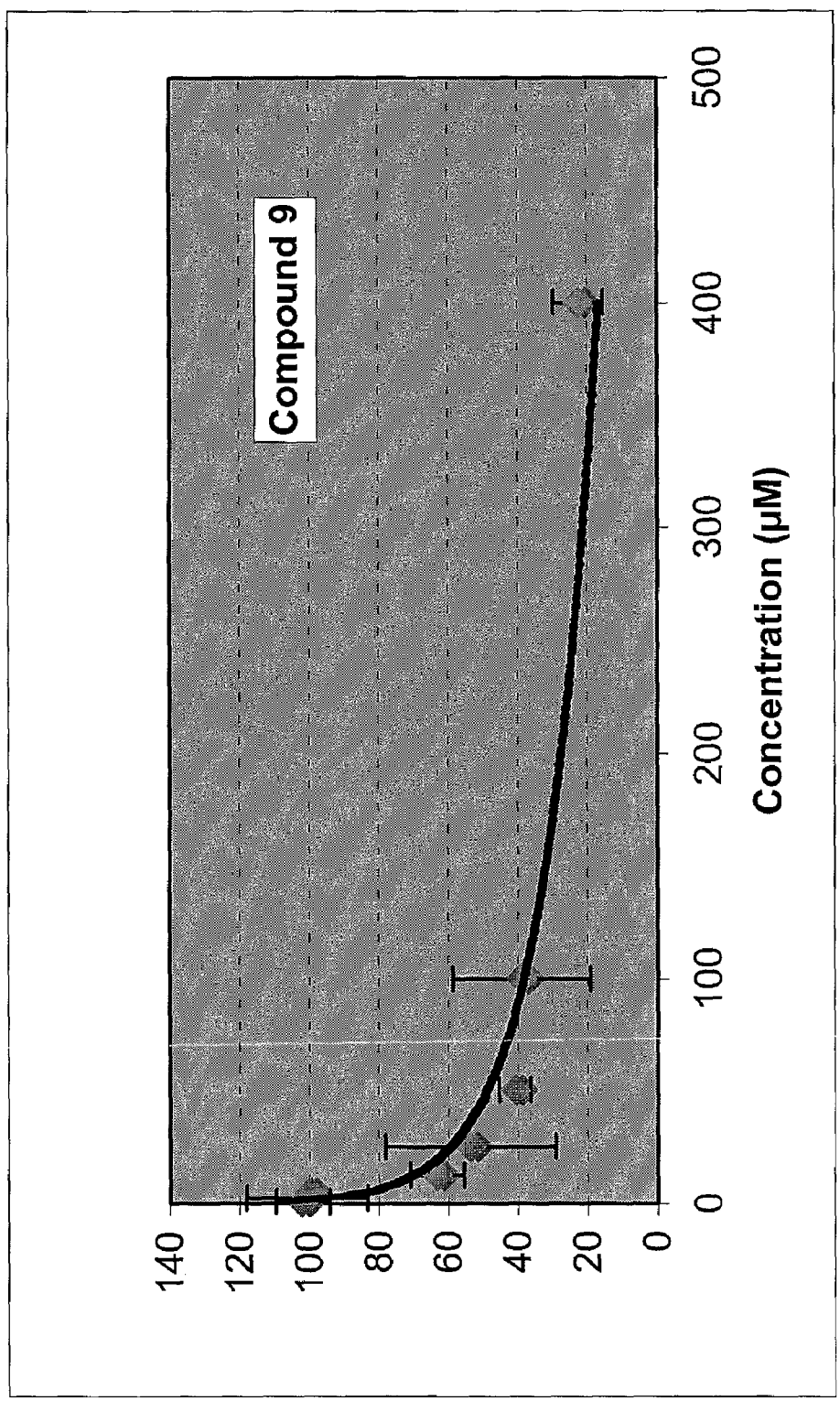

Agonism/antagonism studies were performed for the synthetic analogs identified in Table 2 in both *A. tumefaciens* and *P. aeruginosa* models. The results of these experiments, illustrated in FIGS. 30 and 31, show not only the power of the reporter assay screen, but also the cross reactivity of the respective ligands in different hosts across the genera of quorum-sensing bacteria. Further, antagonism assays shown in FIGS. 32 and 33 illustrated the effectiveness of the AHL analogs across a concentration ranges and indicate that varying the concentration of synthetic ligands can result in an intermediate response, such that at high concentrations there is virtually no signal.

Example 39

*Agrobacterium tumefaciens* Reporter Gene Assay

An appropriate amount of concentrated AHL stock solution, to give a final concentration of 100 nM, was added to an empty culture tube, and the solvent was allowed to evaporate. An overnight culture of *A. tumefaciens* WCF47(pCF372) was diluted to an $OD_{600}$ (optical density) of 0.1 in fresh AB minimal medium containing 400 µg/mL octopine and 50 µg/mL streptomycin. A 1 mL portion of the diluted culture was added to the tubes containing AHLs. Tubes were grown at 28° C. for 12-16 h in a rotary shaking incubator (200 rpm).

The cultures were then assayed for β-galactosidase activity following the Miller assay method. Briefly, 100 µL aliquots of bacteria from each of the tubes were added to wells of a polystyrene 96-well plate and the $OD_{600}$ of each well was recorded. Next, 50 mL aliquots from each well were transferred to a solvent resistant 96-well plate containing 200 µL Z buffer, 8 µL $CHCl_3$ and 4 µL, 0.1% aq. sodium dodecylsulfate (SDS). This suspension was mixed via repetitive pipetting, after which the $CHCl_3$ was allowed to settle. A 100 µL aliquot from each well was transferred to a fresh polystyrene 96-well plate, and 20 µL of substrate, o-nitrophenyl-β-D-galactopyranoside (ONPG, 4 µg/mL in phosphate buffer), was added at time zero. After the development of appropriate yellow color (ca. 15-35 minutes), the reaction was terminated by the addition of 50 µL of 1 M $Na_2CO_3$. Absorbance at 420 nm and 550 nm was measured for each well using a plate reader, and Miller units were calculated according to standard methods.

Similar methods were used for antagonism assays, except the concentration of AHL analog used was $10^4$ nM, and OOHL (8b) stock solution was added to each tube such that its concentration was 100 nM (FIG. 30). Compounds that showed good inhibitory activity at $10^4$ nM were then tested through a range of concentrations against OHHL (8b) at 100 nM, from $10^4$ nM to 1 nM (shown in FIG. 32). All assays were performed in triplicate.

FIG. 30, shows the results for the *A. tumefaciens* reporter gene screening data for AHL derivatives 7h-7r and 8f-8h. Data for control compounds 7g, 8f, and 9 are shown. Reporter strain: WCF47(pCF372). Miller units report relative β-galactosidase activity with ONPG as colorimetric substrate. Compound concentration in agonism assays: 100 nM. Compound concentration in antagonism assays: $10^4$ nM against 100 nM native ligand 8b (OOHL). Error bars are ±one S.E.M., calculated from three replicate screens.

FIG. 31 shows antagonism screening data for AHL derivatives 7k and 7o in an *A. tumefaciens* reporter strain over a concentration range. Reporter strain: WCF47(pCF372). Miller units report relative β-galactosidase activity with ONPG as calorimetric substrate. Compounds screened at various concentrations against 100 nM native ligand 8b (OOHL). FIGS. 31A-31F are graphical displays of the results of dose response antagonism screening data for AHL derivatives 7h (FIG. 31A), 7k (FIG. 31B) and 7o (FIG. 31C) and control compounds 7g (FIG. 31D), 8f (FIG. 31E) and 9 (FIG. 31F) in an *A. tumefaciens* reporter strain. Reporter strain: WCF47(pCF372). Miller units report relative beta-galactosidase activity with ONPG as colometric substrate. Compounds screened at various concentrations against 100 nM native ligand 8b (OOHL). Error bars are ±one S.E.M., calculated from at least three replicate screens.

Example 40

*Pseudomonas aeruginosa* Reporter Gene Assays

An appropriate amount of concentrated stock solution, to give a final concentration of 1 µM, was added to a polypropylene 96-well plate, and the solvent was allowed to evaporate. An overnight culture of *P. aeruginosa* PAO-JP2(plasI-LVAgfp) was diluted to an $OD_{600}$ of 0.1 in fresh LB medium containing 200 µg/mL carbenicillin. 200 µL of the diluted culture was added to each well of the plate and incubated at 37° C. for 6 h in a rotary shaking incubator (200 rpm). Cultures were transferred to a polystyrene 96-well plate, GFP expression was measured using a plate reader, and this value was normalized to cell density. Similar methods were used for antagonism assays, illustrated in FIG. 32, except the concentration of AHL analog used was 400 µM and ODHL (8d) stock solution was added to each well such that its concentration was 1 µM. Compounds that showed good inhibitory activity at 400 µM were then tested through a range of concentrations against ODHL (8d) at 1 µM, from 400 µM to 4 nM (shown in FIG. 33). All assays were performed in triplicate.

FIG. 32, *P. aeruginosa* reporter gene screening data for AHL derivatives 7h-7r and 8f-8h. Data for control compounds 7g, 8f, and 9 are shown. Reporter strain: PAO-JP2 (plasI-LVAgfp). Fluorescence reported as percentage relative to control (8d, ODHL). Compound concentration in agonism assays: 1 µM. Compound concentration in antagonism assays: 400 µM against 1 µM native ligand 8d (ODHL). Error bars are ±one S.E.M., calculated from three replicate screens.

FIGS. 33A-33F are graphical displays of the results of dose response antagonism screening data for AHL derivatives 7h (FIG. 33A), 7k (FIG. 33B) and 7o (FIG. 33C) and control compounds 7g (FIG. 33D), 8f (FIG. 33E) and 9 (FIG. 331F) in an *P. aeruginosa* reporter strain. Reporter strain: PAO-JP2 (plasI-LVAgfp). Fluorescence reported as percentage relative to native ligand 8d (ODHL). Compounds screened at various concentrations against 1 µM native ligand 8d (ODHL). Error bars are ±one S.E.M., calculated from at least three replicate screens.

The data presented in FIGS. 31A-31F and FIGS. 33A-33F were fit to sigmoid dose-response curves to calculate $IC_{50}$ values, which are presented in Table 4, below.

Figure 34A:
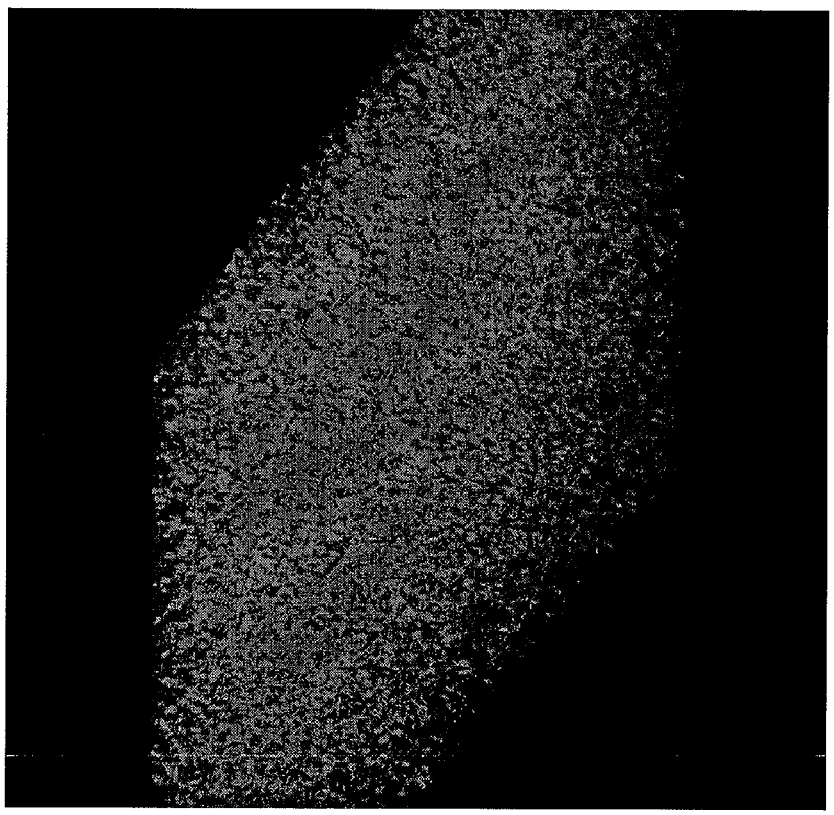
FIGS. 34A-C show composite 3D micrographs of *P. aeruginosa* biofilms grown on glass slides after 48 hours in the presence of synthetic ligands (at 50 µM)
Figure 34B:
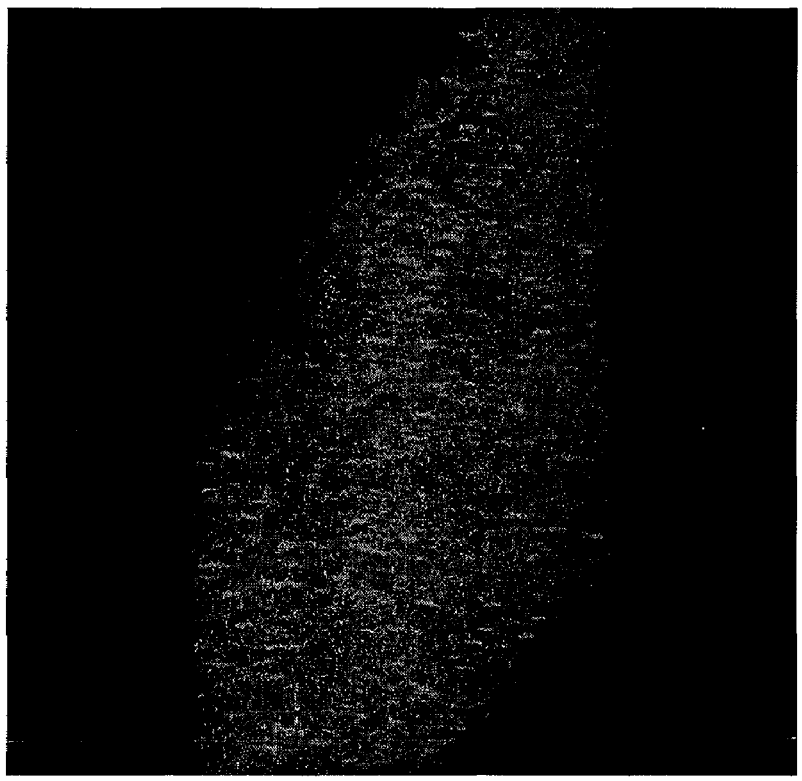
Figure 34C:
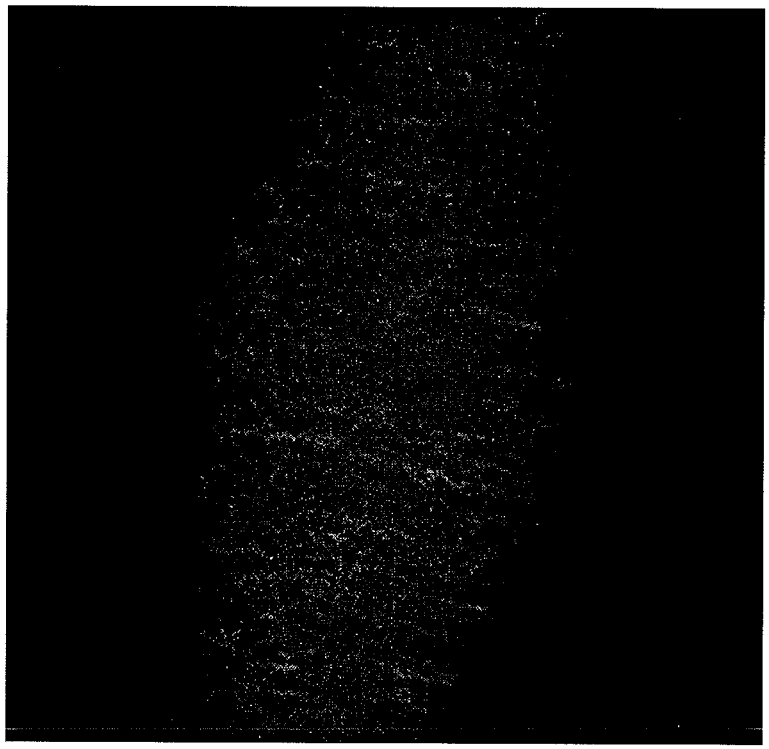

Standard static biofilm assays were performed using a *P. aeruginosa* (PAO1(pLVAgfp)) strain that constitutively produces GFP to facilitate visualization. Biofilms were grown in the absence of ligand (FIG. 34A) and in the presence of 50 µM synthetic ligands 7h (FIG. 34B) or 7o (FIG. 34C), for 48 h and visualized using scanning laser confocal microscopy. The treated biofilms appeared significantly less fluorescent relative to the untreated control, which has been used previously to establish that biofilms have reduced cell densities and are weakly organized. These data indicate that both non-natural quorum sensing compounds 7h and 7o strongly inhibit *P. aeruginosa* biofilm formation.

Example 42

Disruption of Biofilm Formation

Figure 35A:
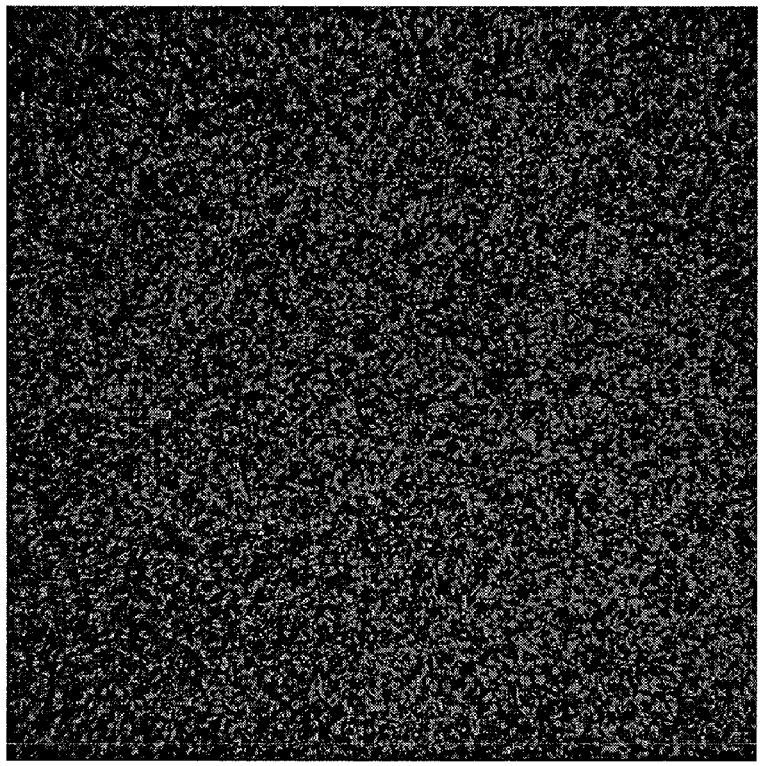
FIGS. 35A-35C show composite stacked scanning confocal laser micrographs of *P. aeruginosa* (PAO1(pLVAgfp)) biofilms grown on glass slides after 48 hours in the presence of synthetic ligands (50 µM). Scale bar=50 µm.
Figure 35B:
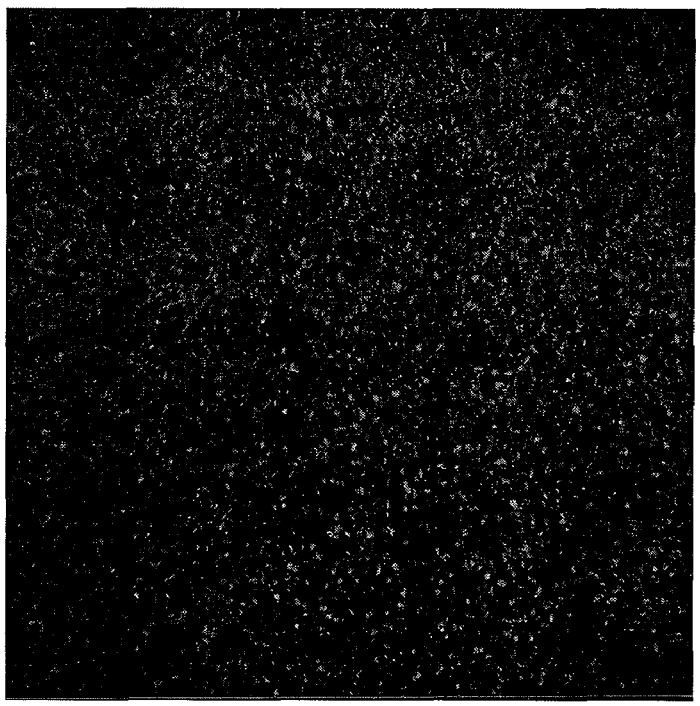

Standard static biofilm assays were performed using a *P. aeruginosa* PAO1(pTdK-GFP). In brief, an overnight culture was diluted to an $OD_{600}$ of 0.1 in fresh M9 medium containing 200 µg/mL carbenicillin. This diluted culture was added to a tube containing 50 µM antagonist. Biofilms were grown in the absence of ligand, FIG. 35A; in the presence synthetic ligand 7h, FIG. 35B; and in the presence of synthetic ligand

TABLE 4

Selected antagonism screening data and $IC_{50}$ inhibition values for AHL derivatives 7h, 7k and 7o and control compounds 7g, 8f, and 9 in *A. tumefaciens* and *P. aeruginosa* reporter strains.[a]

| compound | *A. tumefaciens* β-galactosidase activity [Miller units] | | | *P. aeruginosa* Relative fluorescence [%][b] | | |
|---|---|---|---|---|---|---|
| | $10^4$ nM[c] | 100 nM[c] | IC50 (µM)[c,d] | 400 µM[e] | 12.5 µM[e] | IC50 (µM)[d,e] |
| 8b: OOHL | —[f] | 385 ± 35[g] | — | — | — | — |
| 8d: ODHL | — | — | — | — | 100 ± 8[h] | — |
| 7h | 150 ± 14 | 245 ± 14 | 1.1 | 14 ± 4 | 52 ± 8 | 14.8 |
| 7k | 19 ± 8 | 306 ± 8 | 1.0 | 24 ± 7 | 72 ± 8 | 33.1 |
| 7o | 0 ± 4 | 193 ± 9 | 0.25 | 14 ± 5 | 58 ± 21 | 16.1 |
| 7g | 34 ± 6 | 226 ± 30 | 0.13 | 29 ± 9 | 78 ± 9 | 51.5 |
| 8f | 51 ± 22 | 310 ± 6 | 0.59 | 27 ± 9 | 82 ± 18 | 53.6 |
| 9 | 186 ± 15 | 396 ± 27 | 4.7 | 23 ± 7 | 63 ± 8 | 37.3 |

[a]*A. tumefaciens* strain: WCF47(pCF372); *P. aeruginosa* strain: PAO-JP2(plasI-LVAgfp).
[b]Relative to agonism by 8d at 1 µM; Set to 100%.
[c]Screened against 100 nM 8b.
[d]IC50 calculated from dose response data shown in FIG. S-5 and S-6 using nonlinear regression sigmoidal dose-response curve fit at 95% confidence with GraphPad Prism software (v. 4.00).
[e]Screened against 1 µM 8d.
[f]Not applicable.
[g]Control: Agonism activity at 100 nM 8b.
[h]Control: Relative agonism activity at 1 µM 8d (note: not at 12.5 µM).

The results of the screening methods in both *A. tumafaciens* and *P. aeruginosa*, illustrate the efficacy of the reporter constructs in screening and determining the agonists/antagonist effects of the AHL analogs synthesized by these methods. Further, the cross reactivity of various AHL analogs is indicated by their ability to interact with both the *A. tumafaciens* and *P. aeruginsoa* reporter strains.

Example 41

Disruption of Biofilm Formation

As biofilm formation is largely under the control of LasR in *P. aeruginosa*, the inventors hypothesized that antagonists 7h and 7o could disrupt *P. aeruginosa* biofilm formation. Assays were performed according to standard procedures reported by Iglewski and co-workers.

Figure 35C:
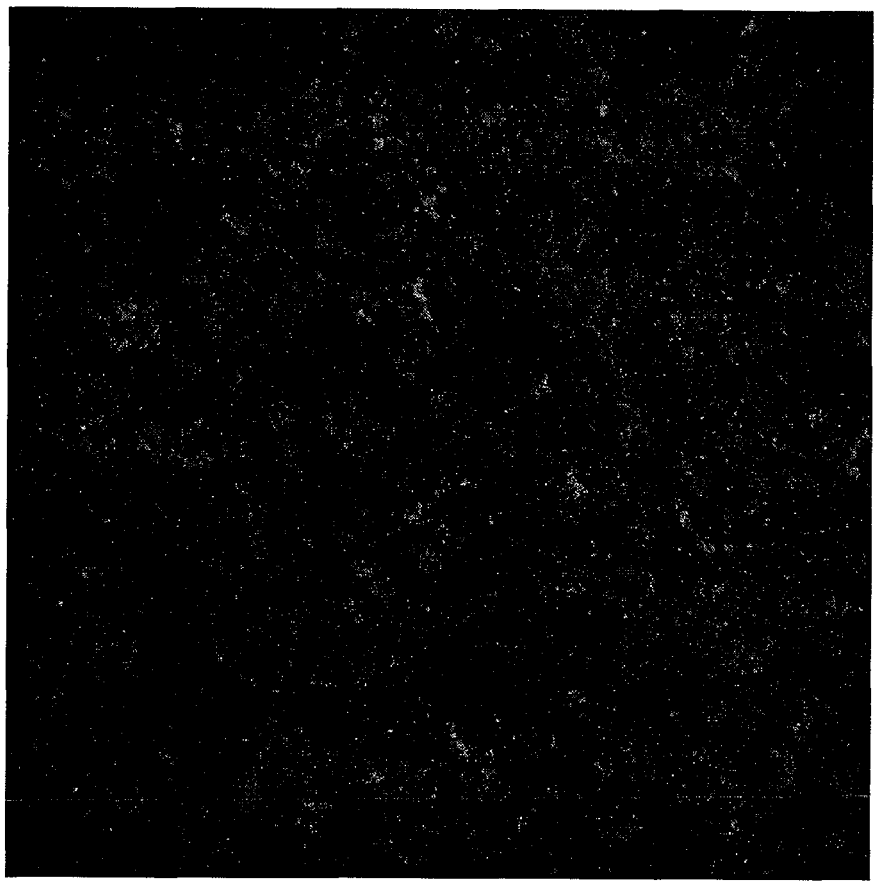

7o, FIG. 35C (both at 50 µM) for 48 h and visualized using scanning laser confocal microscopy. A sterilized glass coverslip was added to each tube, and the culture was incubated at 37° C. for 48 h without shaking. Coverslips were removed, washed with phosphate buffered saline, and examined using scanning laser confocal microscopy methods. Top-down Z series were collected over a distance of ca. 100 µm. Images in FIGS. 35-37 are representative of several experiments performed on separate days.

Example 43

Assay of Dose-Dependent Disruption of *P. aeruginosa* Biofilm: Compound 7o

Figure 36A:
FIGS. 36A-36D show composite stacked scanning confocal laser micrographs of *P. aeruginosa* (PAO1 (pLVAgfp)) biofilms grown on glass slides after 48 hours in the presence of AHL ligand 7o. Scale bar=10 μm.
Figure 36B:
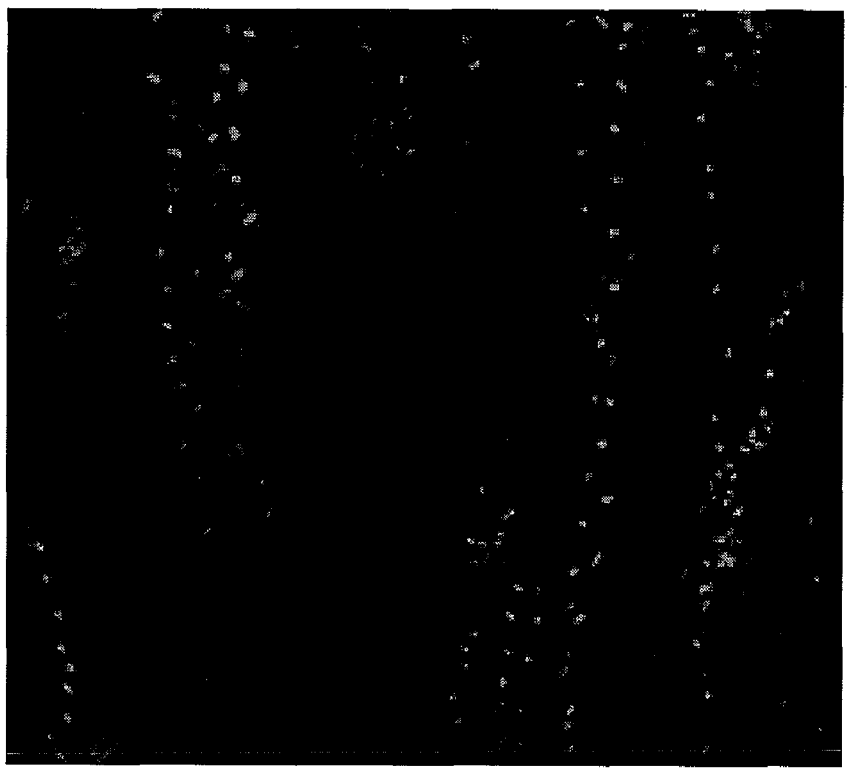
Figure 36C:
Figure 36D:
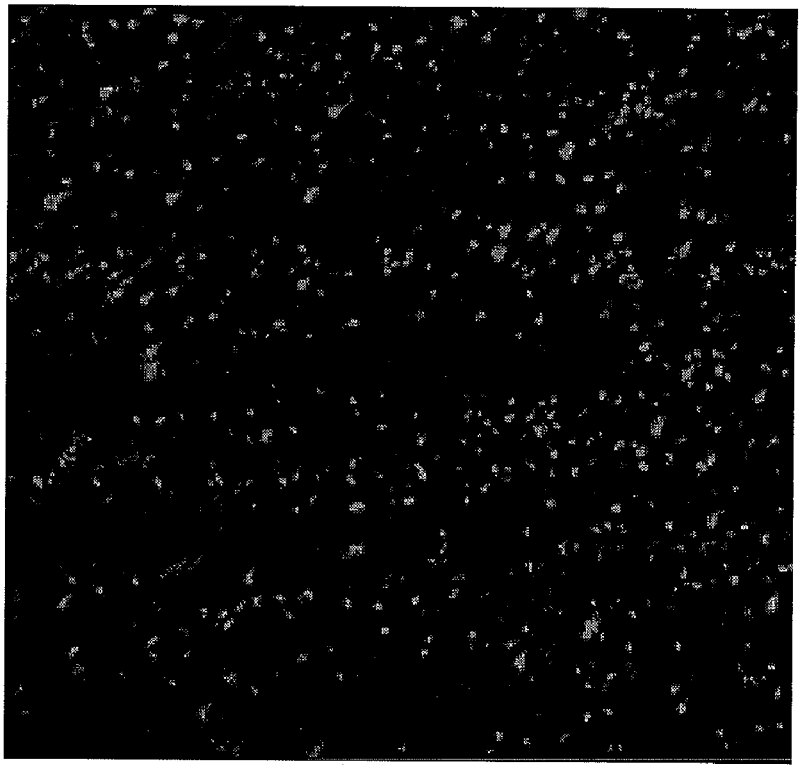

The dose-dependent relationship of synthetic quorum sensing compound 7o was explored using the methods described above but with the treatment groups comprising: untreated (FIG. 36A); 50 μM 7o (FIG. 36B); 25 μM 7o (FIG. 36C) and 12.5 μM 7o (FIG. 36D). Composite stacked scanning confocal laser micrographs of *P. aeruginosa* (PAO1 (pLVAgfp)) clearly indicate a dose-dependent disruption of the biofilm.

Example 44

Assay of Dose-Dependent Disruption of *P. aeruginosa* Biofilm: Compound 7h

Figure 37A:
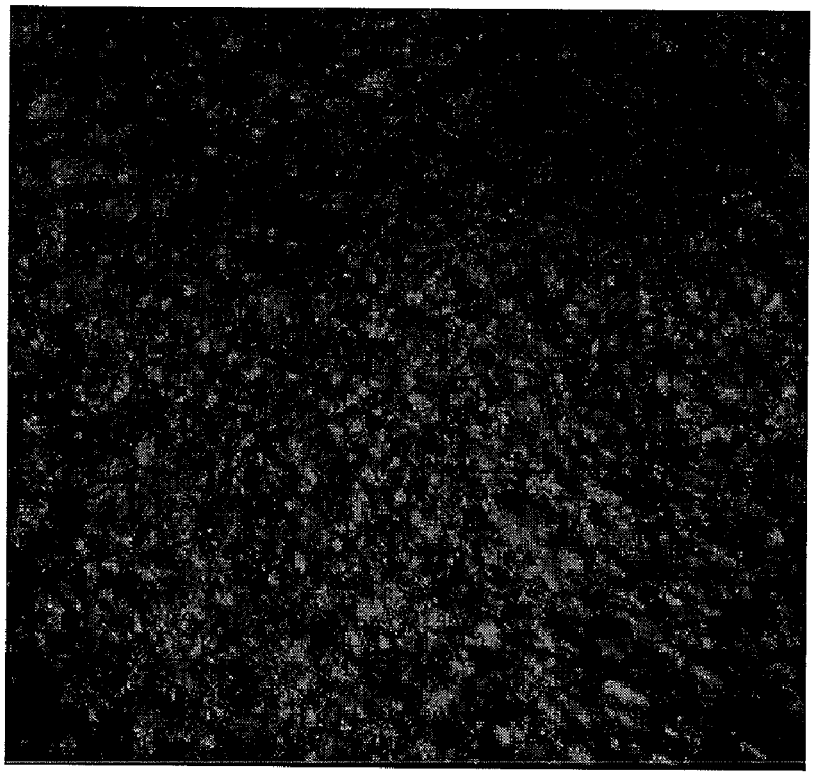
FIGS. 37A-37D show composite stacked scanning confocal laser micrographs of *P. aeruginosa* (PAO1(pLVAgfp)) biofilms grown on glass slides after 48 hours in the presence of AHL ligand 7h. Scale bar=10 μm.
Figure 37B:
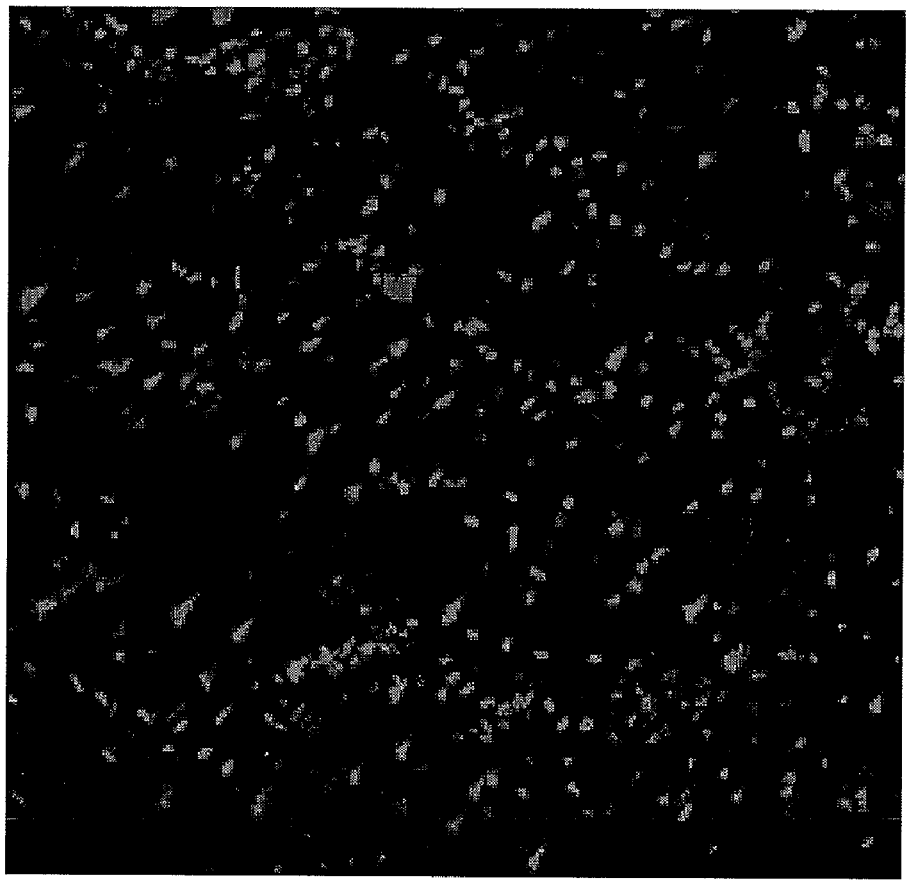
Figure 37C:
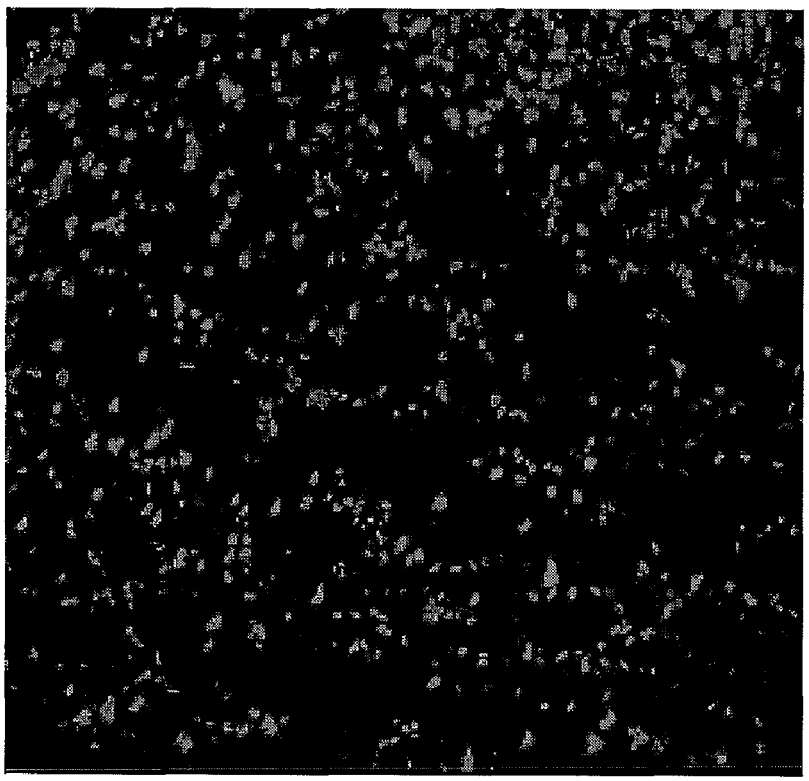
Figure 37D:
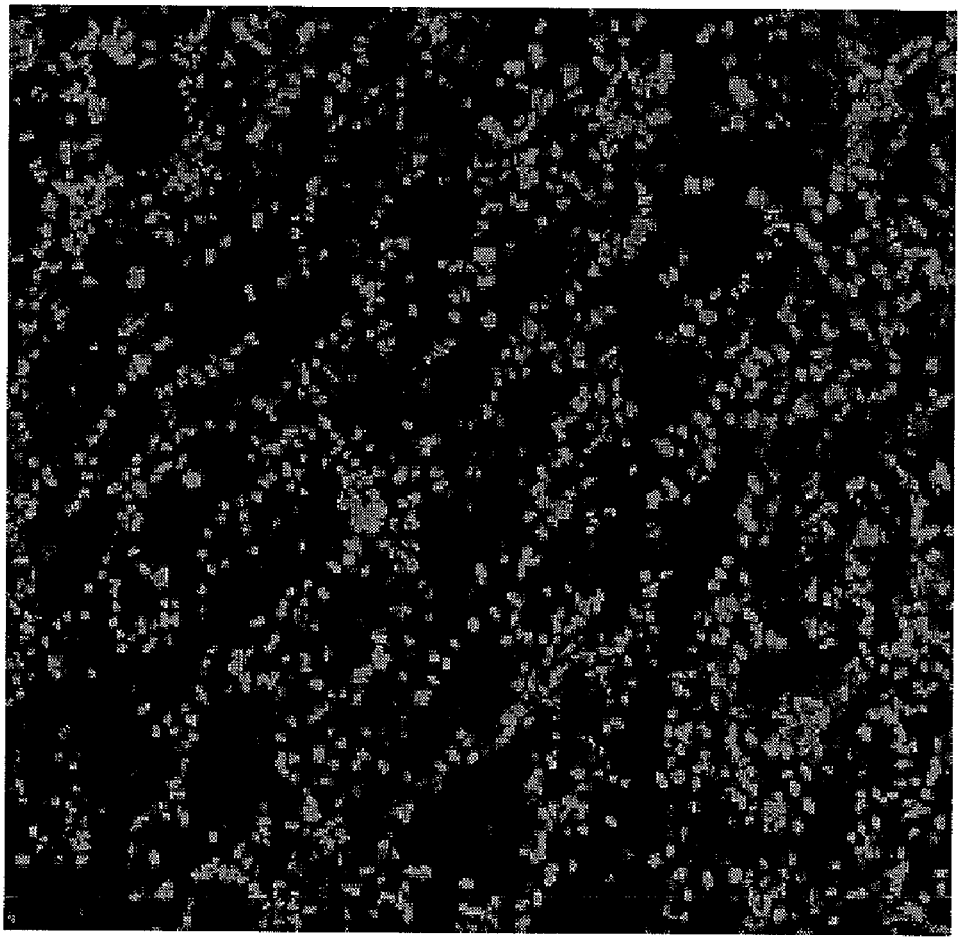

The dose-dependent relationship of synthetic quorum sensing compound 7h was explored using the methods described above but with the treatment groups comprising: untreated (FIG. 37A); 50 μM 7h (FIG. 37B); 25 μM 7h (FIG. 37C); and 12.5 μM 7h (FIG. 37D). Composite stacked scanning confocal laser micrographs of *P. aeruginosa* (PAO1 (pLVAgfp)) clearly indicate a dose-dependent disruption of the biofilm.

The importance of these findings is highlighted by the fact that few inhibitors of bacterial biofilm formation are known. Moreover the effects illustrated in FIGS. 36A-D and FIGS. 37A-D illustrate that there is a dose-dependent effect for these compounds. This indicates intermediate responses are obtainable and that the mechanism of action may be similar for each of the compounds analyzed throughout a broad range of genera of quorum-sensing bacteria.

Quorum sensing compounds such as those herein described, are anticipated to have direct impact in health care and other industries where bacterial contamination is prevalent. The ability of a soluble, diffusible quorum sensing compound to inhibit biofilm formation when introduced or contacted to an environment has direct clinical and public health implications such as those related to bacterial contamination of surgical instruments and food and water resources. Moreover, the discovery of potent inhibitors from the small combinatorial library described herein highlights the potential utility of focused combinatorial methods for the discovery of additional small molecule modulators of quorum sensing.

In summary, the invention provides a robust synthetic route to quorum sensing compounds, including AHL autoinducers, that provides access to both natural and unnatural AHLs in high purity. The synthetic route herein disclosed has been used to identify a set of non-native AHLs that are potent inhibitors of bacterial quorum sensing. Further, the compounds developed by the disclosed methods allows the identification of both agonists and antagonists and provides methods for their rapid characterization and screening. Such compounds may be used to both inhibit cell to cell communication via quorum sensing as well as create miscommunication between such cells via the quorum sensing system. Manipulate the quorum sensing of pathogenic and destructive bacteria allows its use in research, health care, agriculture, food processing and other industries to either inhibit signaling and therefore inhibit the transcription of lethal genes or to prematurely elicit the transcription of such genes so as to short-circuit the associated pathogenesis. In short, the compounds and methods described herein represent powerful new tools to control the growth, virulence and pathogenicity of bacteria.

What is claimed is:

1. A method for modulating or regulating infectivity and pathogenicity of a quorum sensing bacterium which comprises contacting the quorum sensing bacterium with one or more compounds selected from the group consisting of:

(a) a compound having formula:

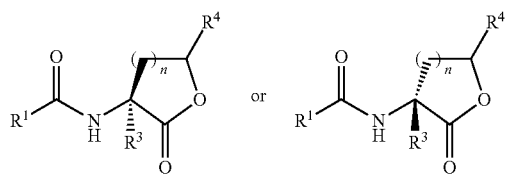

where n is 1, 2 or 3,
$R^4$ is —H, $R^3$ is —H, —CH$_3$ or —CH$_2$—CH$_3$, and
$R^1$ is selected from:

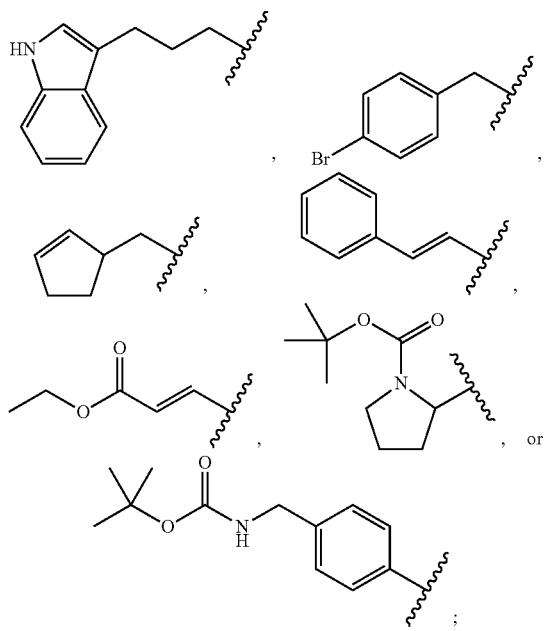

(b) a compound selected from compounds having formulas:

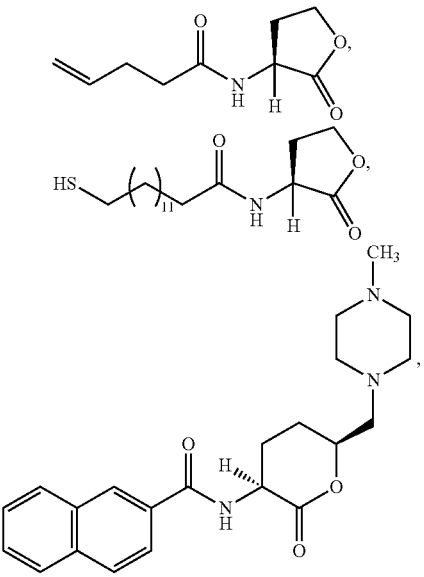

53

-continued

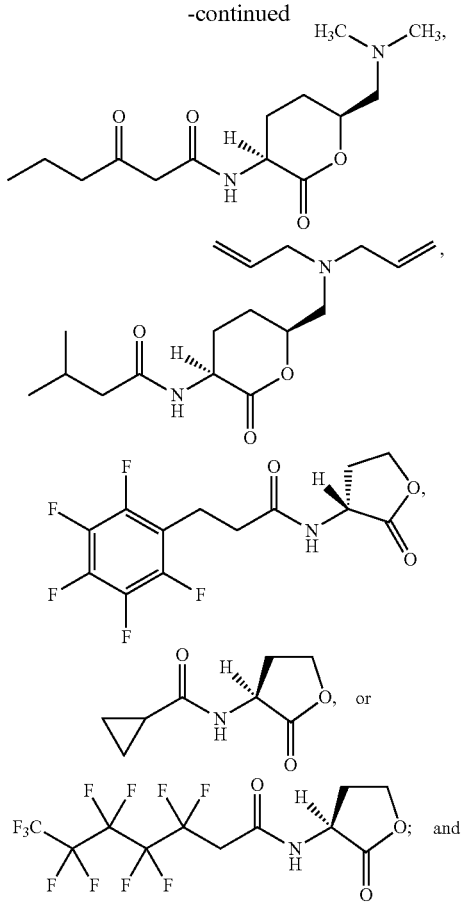

(c) a compound of formula:

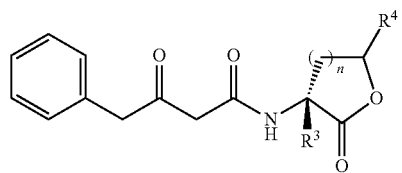

where n is 1, 2 or 3, R³ is selected from —H, —CH₂CH₃, or —CH₃, and R⁴ is selected from —H, or —CH₃.

2. The method of claim 1, wherein the one or more compounds act as agonists of native quorum sensing compounds.

3. The method of claim 1, wherein the one or more compounds act as antagonists of native quorum sensing compounds.

4. The method of claim 1, wherein the quorum sensing bacterium is a Gram negative bacterium.

5. The method of claim 1, wherein modulating or regulating infectivity and pathogenicity of a quorum sensing bacterium includes reducing the bacterial contamination of surfaces prone to bacterial biofilm contamination comprising contacting the surface with one or more of said compounds.

6. The method of claim 5, wherein contacting includes: spraying, painting brushing, applying or treating the surface with a solution containing one or more of said compounds.

7. The method of claim 6, wherein the solution is an aqueous solution which contains a mixture of two or more of said compounds.

54

8. The method of claim 6 wherein modulating or regulating infectivity and pathogenicity of a quorum sensing bacterium includes inhibiting or diminishing biofilm production and the method comprises the step of contacting the bacterial biofilm with a composition comprising one or more of said compounds.

9. The method of claim 8, wherein the step of contacting includes the step of spraying, painting, brushing, applying or treating the bacterial biofilm with the composition.

10. The method of claim 1, wherein the contacting is performed in vitro.

11. The method of claim 1, wherein the contacting is performed in vivo.

12. The method of claim 1 wherein the one or more compounds are selected from:

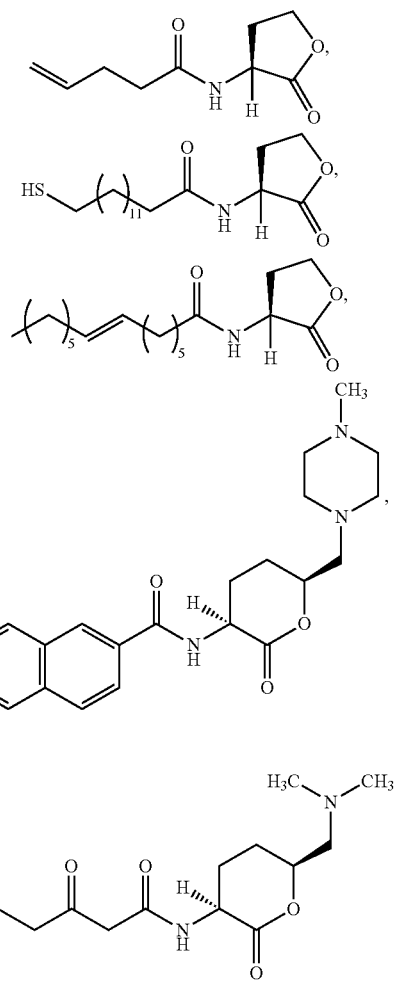

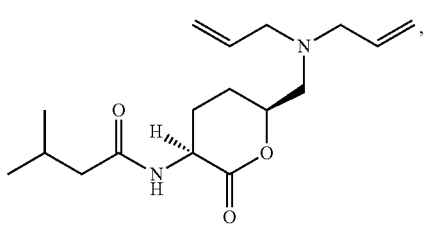

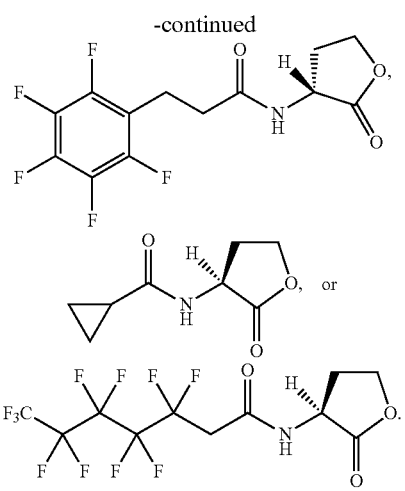

13. The method of claim 12, wherein modulating or regulating infectivity and pathogenicity of quorum sensing bacteria comprises reducing the virulence of quorum sensing bacteria.

14. The method of claim 13, wherein reducing the virulence of a quorum sensing bacteria includes inhibiting or diminishing biofilm production.

15. The method of claim 1 wherein the one or more compounds have formula:

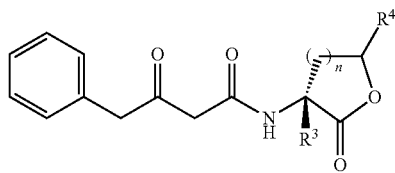

where n is 1, 2 or 3, $R^3$ is selected from —H, —$CH_2CH_3$, or —$CH_3$, and $R^4$ is selected from —H, or —$CH_3$.

16. The method of claim 15, wherein the one or more compounds act as antagonists of native quorum sensing compounds.

17. The method of claim 15, wherein the one or more compounds act as agonists of native quorum sensing compounds.

18. The method of claim 15, wherein the quorum sensing bacterium is a Gram negative bacterium.

19. The method of claim 15, wherein $R^3$ and $R^4$ are —H.

20. The method of claim 15, wherein n is 1.

21. The method of claim 15, wherein n is 1 and $R^3$ and $R^4$ are —H.

* * * * *